United States Patent
Gray et al.

(10) Patent No.: US 10,975,055 B2
(45) Date of Patent: Apr. 13, 2021

(54) INHIBITORS OF INTERLEUKIN-1 RECEPTOR-ASSOCIATED KINASES AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US); John Hatcher, Marlborough, MA (US); Sara Jean Buhrlage, Somerville, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/462,200

(22) PCT Filed: Nov. 22, 2017

(86) PCT No.: PCT/US2017/063139
§ 371 (c)(1),
(2) Date: May 17, 2019

(87) PCT Pub. No.: WO2018/098367
PCT Pub. Date: May 31, 2018

(65) Prior Publication Data
US 2019/0276426 A1    Sep. 12, 2019
US 2020/0299257 A9    Sep. 24, 2020

Related U.S. Application Data

(60) Provisional application No. 62/425,503, filed on Nov. 22, 2016.

(51) Int. Cl.
C07D 401/04    (2006.01)
A61P 35/00     (2006.01)
C07D 213/81    (2006.01)
C07D 401/14    (2006.01)
C07D 413/04    (2006.01)

(52) U.S. Cl.
CPC ............ C07D 401/04 (2013.01); A61P 35/00 (2018.01); C07D 213/81 (2013.01); C07D 401/14 (2013.01); C07D 413/04 (2013.01)

(58) Field of Classification Search
None
See application file for complete search history.

(56) References Cited

U.S. PATENT DOCUMENTS 9,067,933 B2 * 6/2015 Corkey ............... A61K 31/585

FOREIGN PATENT DOCUMENTS

| WO | WO 2014/058691 A1 | 4/2014 |
| WO | WO 2015/106058 A1 | 7/2015 |
| WO | WO 2016/081679 A1 | 5/2016 |

OTHER PUBLICATIONS

International Search Report and Written Opinion for Application No. PCT/US2017/063130 dated Jan. 30, 2018.
International Preliminary Report on Patentability for Application No. PCT/US2017/063139 dated Jun. 6, 2019.

* cited by examiner

*Primary Examiner* — Zinna Northington Davis
(74) *Attorney, Agent, or Firm* — Wolf, Greenfield & Sacks, P.C.

(57) ABSTRACT

The present invention provides novel compounds of Formula (I'), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing proliferative diseases (e.g., cancers (e.g., leukemia, lymphoma)), inflammatory diseases, autoinflammatory diseases, and autoimmune diseases in a subject. Treatment of a subject with a proliferative disease using a compound or composition of the invention may inhibit the aberrant activity of a kinase, such as an interleukin-1 receptor-associated kinase (IRAK) (e.g., IRAKI and/or IRAK4) in the subject.

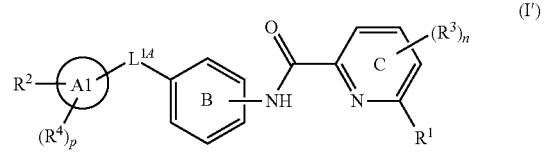

20 Claims, 16 Drawing Sheets

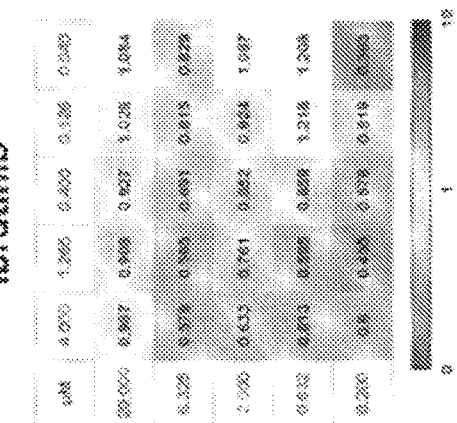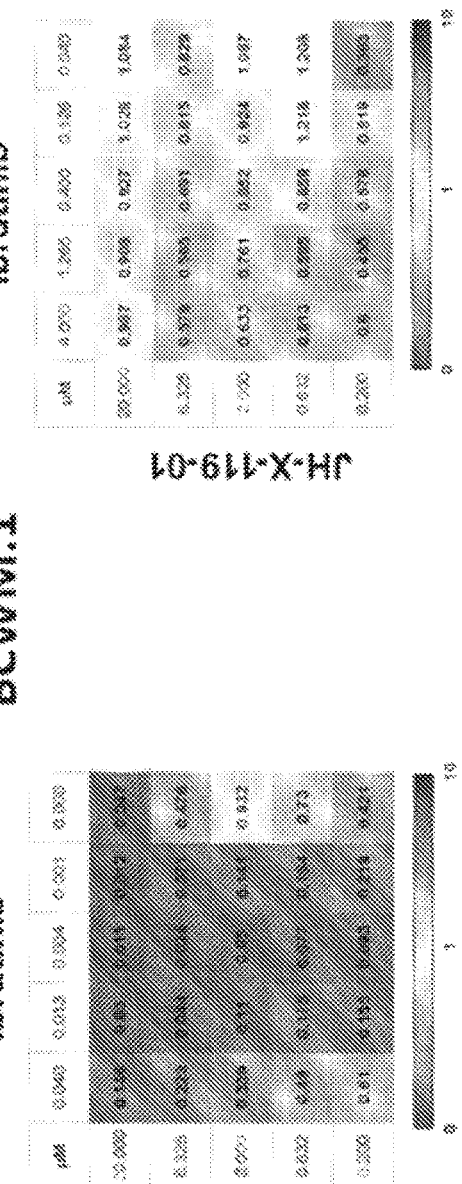
Figure 1C

THZ2-118

IRAK1 IC$_{50}$ = 14.2 nM
IRAK4 IC$_{50}$ > 10,000 nM
JNK1/2/3 IC$_{50}$ = 2/2/1 nM

JH-I-025

IRAK1 IC$_{50}$ = 9 nM
IRAK4 IC$_{50}$ = 17 nM

| Cmpd | IRAK1 IC$_{50}$ (nM) | IRAK4 IC$_{50}$ (nM) | Labelling Site |
|---|---|---|---|
| JH-X-119-01 | 9 | >10,000nM | Cys 302 |
| JH-X-119-02 | 47 | >10,000nM | Cys 307 |
| JH-X-119-03 | 55 | >10,000nM | Cys 302 & Cys 307 (1:1) |
| JH-X-119-04 | 25 | >10,000nM | Cys 302 |
| JH-X-169 | 269 | >10,000nM | N/A |
| JH-X-128 | 52 | >10,000nM | Cys 302 |

Figure 4

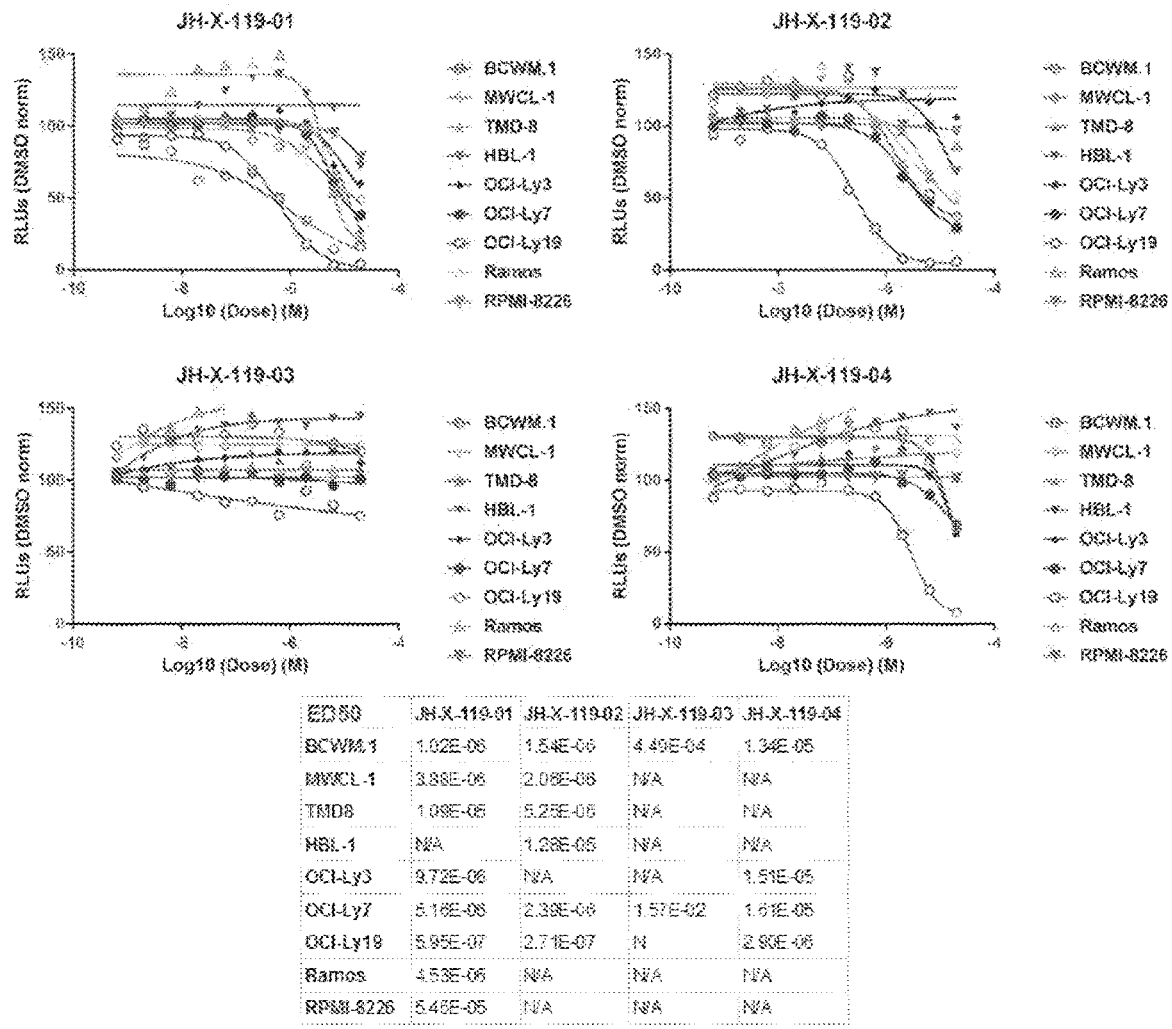
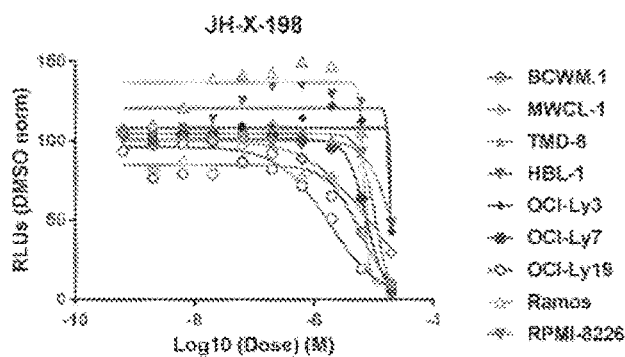
Figure 7

INHIBITORS OF INTERLEUKIN-1 RECEPTOR-ASSOCIATED KINASES AND USES THEREOF

RELATED APPLICATIONS

This application is a national stage filing under 35 U.S.C. § 371 of international PCT application, PCT/US2017/063139, filed Nov. 22, 2017, which claims priority under 35 U.S.C § 119(e) to U.S. provisional application, U.S. Ser. No. 62/425,503, filed Nov. 22, 2016, each of which is incorporated herein by reference.

BACKGROUND OF THE INVENTION

IRAK1 is a serine/threonine kinase that was originally identified in 1994. Altogether there are four IRAK kinases: IRAK1 and IRAK4, which are catalytically active kinases, and IRAK2 and IRAK3, which are believed to be catalytically inactive and are hence classified as 'pseudokinases.' IRAK1 is ubiquitously expressed with its highest expression observed in blood and immune tissues (for example, bone marrow, lymph nodes, thymus and peripheral blood) and hematological malignancies. IRAK signaling contributes to multiple signaling pathways downstream of the Toll-interleukin receptors (TIRs) that ultimately regulate NF-κB and IFN regulatory factors (IRFs). In the case of NF-κB, IRAK1 mediates the downstream signals of TIRs through an interaction with MYD88 which is rapidly recruited to the receptor upon ligand binding to either IL-1R or a TLR. Subsequent phosphorylation on IRAK1 by upstream signals or through autophosphorylation is the key post-translational modification and hallmark of its activation which allows IRAK1 to bind to TRAF6 resulting in release of the IRAK1 homodimer from MYD88 and downstream NF-κB activation.

The participation of IRAK1 in signaling networks of the innate immune response has defined the enzyme as a critical regulator of inflammation, the antiviral response, and the subsequent activation of the adaptive immune response. Consequently, an extensive investigation into physiological and pathological functions of IRAK1 in regulating these processes has been performed. In particular, these studies have implicated IRAK1 inhibition as potential treatment for myocardial contractile dysfunction following burn, autoimmune conditions associated with hyper inflammation, myocardial dysfunction, microbial septic response, human myelodysplastic syndrome (MDS), and acute myeloid leukemia (AML). In Waldenström macroglobulinemia cells, the MYD88 L265P somatic mutation is highly prevalent and responsible for malignant growth through activation of nuclear factor NF-κB. Two downstream signaling branches, one including BTK and one including IRAK1, both regulate NF-κB activation in Myd88L265P expressing WM cell lines. IRAK1 inhibitors should be pursued for the disease since genetic knockdown of either BTK or IRAK1 leads to modest cell killing; and IRAK1 is activated in viable cells isolated from WM patient currently receiving Ibrutinib therapy WM cell lines, and primary patient samples treated with an IRAK1/4 inhibitor and a BTK inhibitor display augmented inhibition of NF-κB signaling and more robust cell killing. Although IRAK1 was identified over twenty years ago, and its critical function in autoimmunity and inflammation has been widely recognized, medicinal chemistry efforts directed at the development of selective inhibitors of IRAK1 have not been reported. Thus, it is important to develop selective inhibitors of IRAK (e.g., IRAK1 and IRAK4) for use as research tools as well as therapeutic agents in the treatment of diseases.

SUMMARY OF THE INVENTION

The present invention provides compounds of Formula (I'), and pharmaceutically acceptable salts, solvates, hydrates, polymorphs, co-crystals, tautomers, stereoisomers, isotopically labeled derivatives, prodrugs, and compositions thereof. The compounds of Formula (I'), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the kinase is an interleukin-1 receptor-associated kinase (IRAK). In certain embodiments, the kinase is IRAK1. In certain embodiments, the kinase is IRAK4. In certain embodiments, the compounds of Formula (I') are selective for IRAK1 compared to other kinases. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., IRAK1) and as therapeutics for the prevention and/or treatment of diseases associated with the overexpression and/or aberrant (e.g., increased or unwanted) activity of a kinase (e.g., IRAK1). In certain embodiments, the inventive compounds are used for the prevention and/or treatment of proliferative diseases (e.g., cancers (e.g., leukemia, lymphoma), inflammatory diseases, autoinflammatory diseases, and autoimmune diseases in a subject.

In one aspect, the present disclosure provides compounds of Formula (I'):

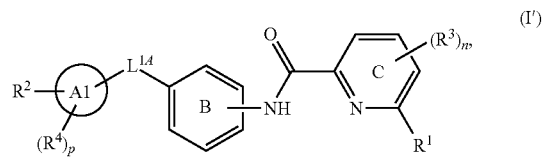

and pharmaceutically acceptable salts, solvates, hydrates, polymorphs, co-crystals, tautomers, stereoisomers, isotopically labeled derivatives, and prodrugs thereof, wherein Ring A1, $R^1$, $R^2$, $R^3$, $R^4$, $L^{1A}$, n, and p are as defined herein.

In one aspect, the present invention provides compounds of Formula (I):

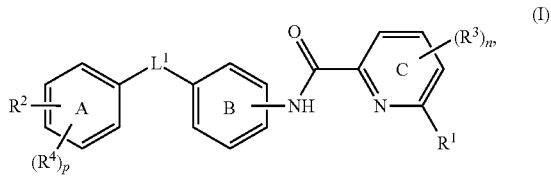

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $L^1$, n, and p are as defined herein.

Exemplary compounds of Formula (I') and (I) include, but are not limited to:

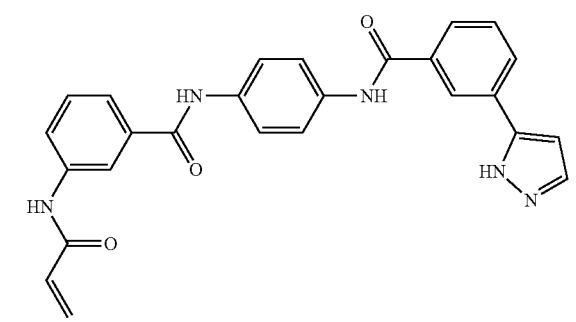
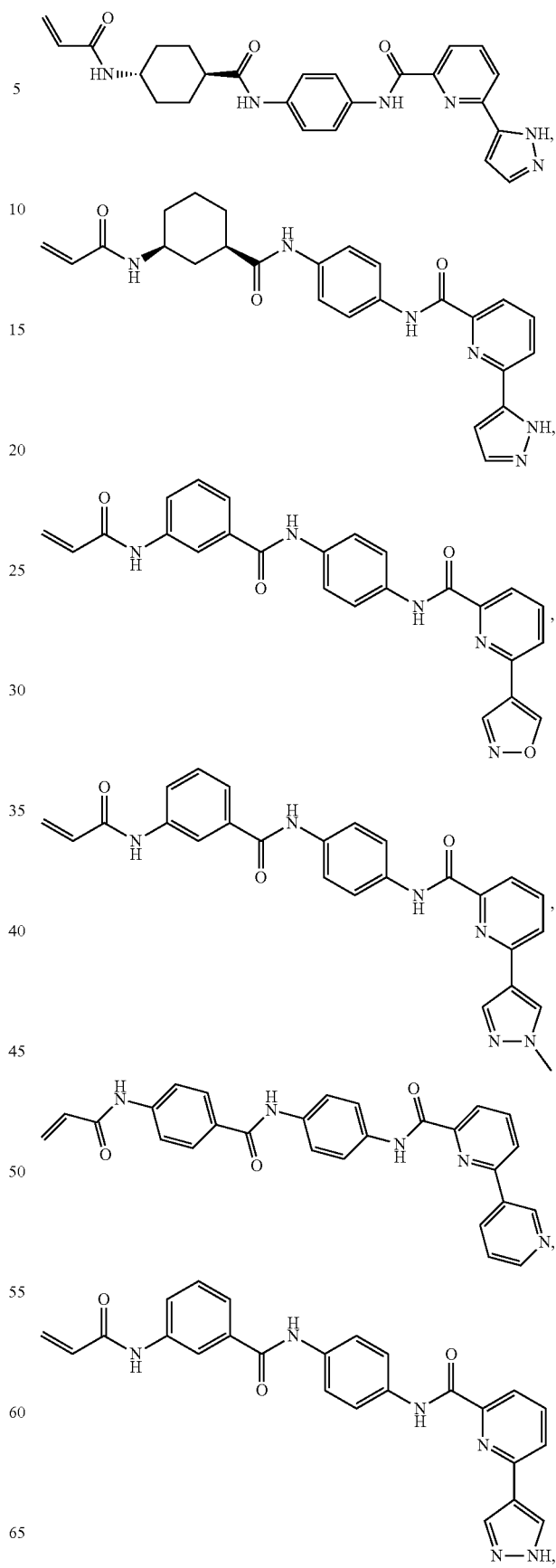
and pharmaceutically acceptable salts, solvates, hydrates, polymorphs, co-crystals, tautomers, stereoisomers, isotopically labeled derivatives, and prodrugs thereof.
Other exemplary compounds of Formula (I') and (I) include, but are not limited to:

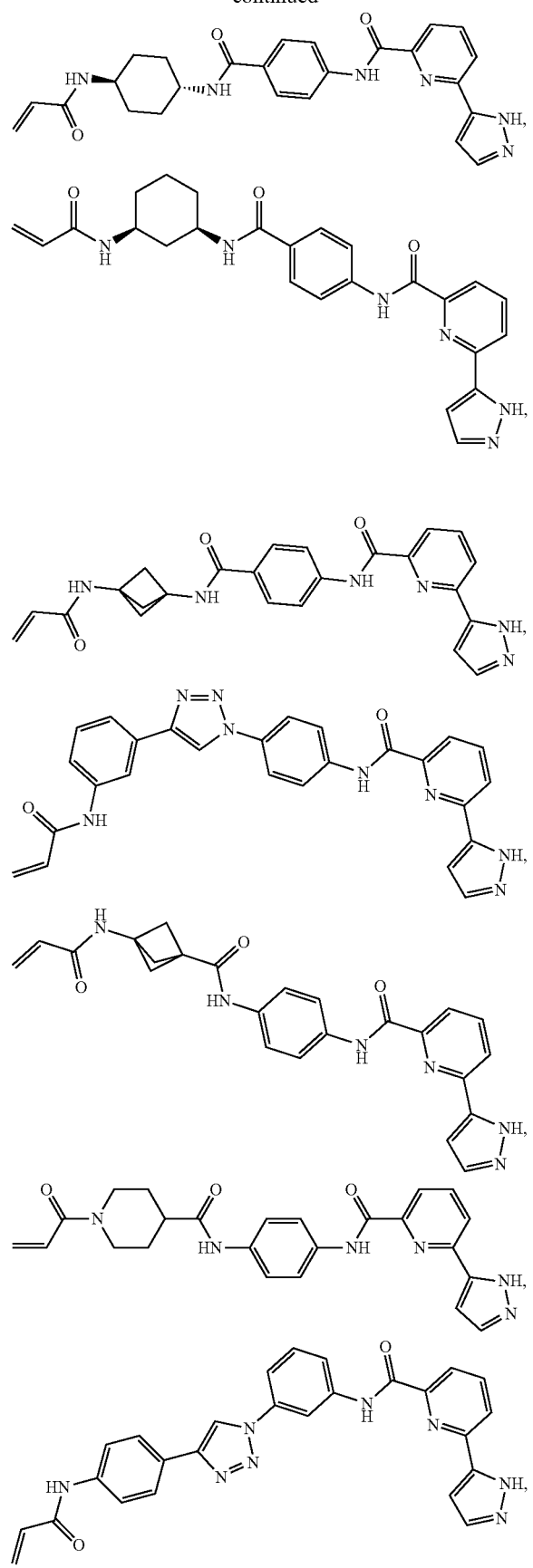
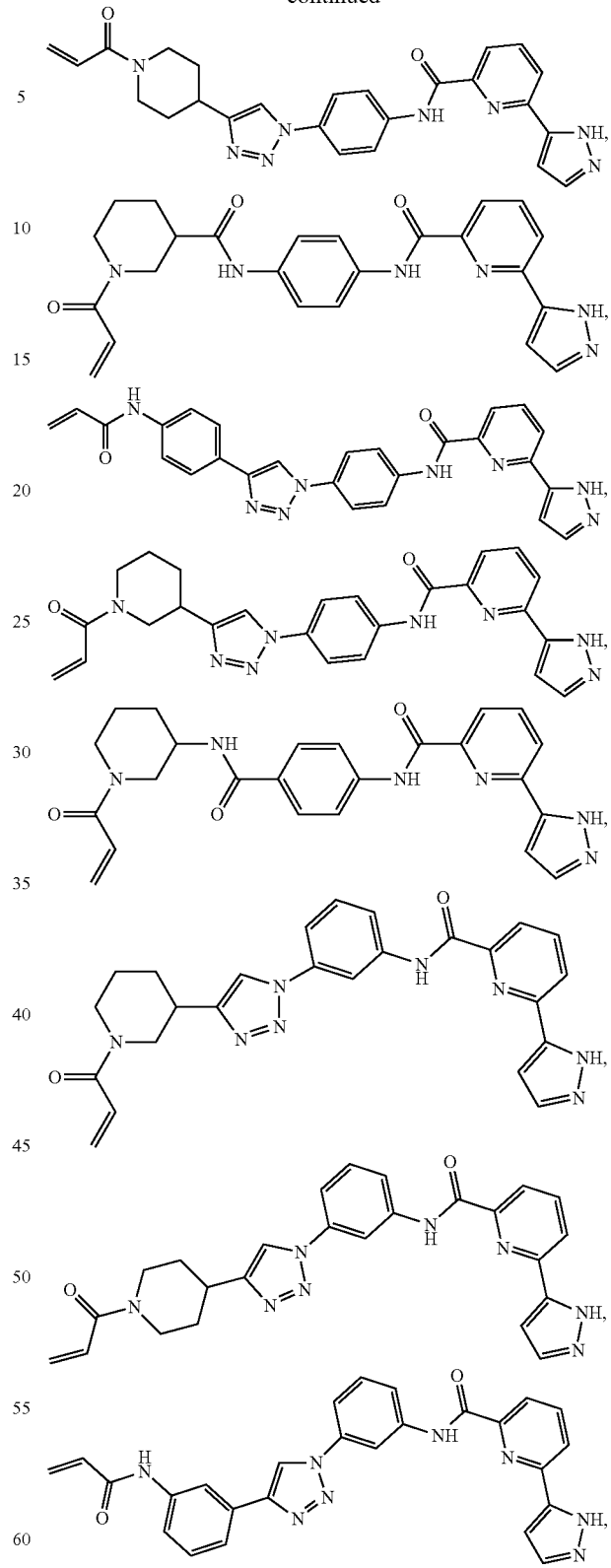
and pharmaceutically acceptable salts, solvates, hydrates, polymorphs, co-crystals, tautomers, stereoisomers, isotopically labeled derivatives, and prodrugs thereof.
In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, or inhibiting the activity of a protein kinase (e.g., IRAK) in a subject, biological sample, tissue, or cell. In certain embodiments, the proliferative disease is cancer (e.g., lymphoma, leukemia, or myelodysplastic syndrome (MDS)). In certain embodiments, the proliferative disease is an inflammatory disease. In certain embodiments, the inflammatory disease is rheumatoid arthritis, Crohn's disease, or fibrosis. In certain embodiments, the proliferative disease is an autoimmune disease.

In another aspect, the present invention provides methods for treating and/or preventing a proliferative disease. Exemplary proliferative diseases which may be treated include diseases associated with the overexpression or increased activity of an interleukin-1 receptor-associated kinase (IRAK), e.g., cancer, benign neoplasms, diseases associated with angiogenesis, inflammatory diseases, autoinflammatory diseases, and autoimmune diseases. In certain embodiments, the cancer is selected from the group consisting of pancreatic cancer, lung cancer (e.g., small cell lung cancer (SCLC), non-small cell lung cancer), prostate cancer, breast cancer, ovarian cancer, kidney cancer, liver cancer, Ewing's sarcoma, myeloma, Waldenström's macroglobulinemia, myelodysplastic syndrome (MDS), osteosarcoma, brain cancer, neuroblastoma, and colorectal cancer.

Another aspect of the invention relates to methods of inhibiting the activity of a kinase (e.g., IRAK (e.g., IRAK1, IRAK4)) using a compound described herein in a biological sample or subject. In certain embodiments, the method involves the selective inhibition of IRAK1. In certain embodiments, the method involves the selective inhibition of IRAK4.

The present invention also provides methods of inhibiting cell growth in a biological sample or subject. In still another aspect, the present invention provides methods of inducing apoptosis of a cell in a biological sample or subject.

The present invention provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent (e.g., an anti-proliferative agent). In certain embodiments, the onal pharmaceutical agent is a kinase inhibitor (e.g., an inhibitor of Bruton's tyrosine kinase (BTK). The methods described herein may further include performing radiotherapy, immunotherapy, and/or transplantation on the subject.

In yet another aspect, the present invention provides compounds of Formula (I'), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease, such as cancer) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and subrange within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^AH(C^BH_2C^CH_3)$— includes only one carbon unit C^A. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH($C_2H_5$)— is a $C_1$ hydrocarbon chain, and

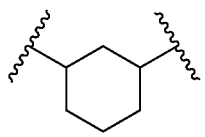 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —($CH_2$)$_4$—). A hydrocarbon chain may also be unsaturated and include one or more C=C and/or C≡C bonds anywhere in the hydrocarbon chain. For instance, —CH=CH($CH_2$)$_2$—, —$CH_2$—C≡$CH_2$, and —C≡C—CH=CH— are all examples of a unsubstituted and unsaturated hydrocarbon chain. In certain embodiments, the hydrocarbon chain is unsubstituted (e.g., —($CH_2$)$_4$—). In certain embodiments, the hydrocarbon chain is substituted (e.g., —CH($C_2H_5$)— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For

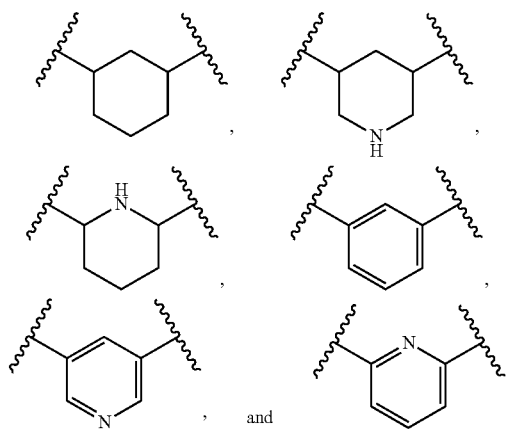

are all examples of a hydrocarbon chain. In contrast, in certain embodiments

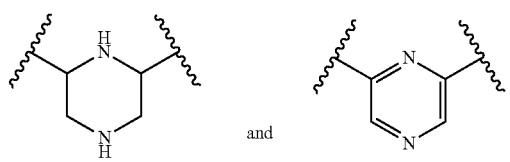 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_2$— alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$— alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_2$— alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-10}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_3$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(=OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PF$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OC(CF$_3$)$_3$)$_4{}^-$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluoroenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})$, —$S(=O)R^{bb}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, gluconate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I') may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2 H$_2$O) and hexahydrates (R.6 H$_2$O)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I'), which have cleavable groups and become by solvolysis or under physiological conditions the compounds of Formula (I') which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I') may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I') refers to an amount sufficient to elicit the desired biological response, i.e., treating the condition. As will be appreciated by those of ordinary skill in this art, the effective amount of a compound of Formula (I') may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I') is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms or causes of the condition, or enhances the therapeutic efficacy of another therapeutic agent.

A "prophylactically effective amount" of a compound of Formula (I') is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLUISLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behcet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as a transgenic oocyte, sperm cell, blastocyst, embryo, fetus, donor cell, or cell nucleus.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain)

and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of phosphate groups to an amino acid residue of a protein. For example, a serine kinase catalyzes the addition of a phosphate group to serine residue in a protein. In certain embodiments, the kinase is a protein kinase. Examples of kinases include, but are not limited to, a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20)), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3α, GSK3β), a CDK-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

The term "IRAK" refers to interleukin-1 receptor-associated kinases. Examples of kinases include, but are not limited to, IRAK1 and IRAK4. IRAK1 and IRAK4 are serine/threonine-protein kinases that play a critical role in initiating innate immune response against foreign pathogens. IRAK1 and IRAK4 are involved in Toll-like receptor (TLR) and IL-1R signaling pathways, and are rapidly recruited by MYD88 to the receptor-signaling complex upon TLR activation.

BRIEF DESCRIPTION OF THE DRAWINGS

The accompanying drawings, which constitute a part of this specification, illustrate several embodiments of the invention and together with the description, serve to explain the principles of the invention.

FIGS. 1A to 1C. Figure JA shows the results of lentiviral transduction studies performed in MYD88 mutated BCWM.1 cells, where it was observed in an inducible model system that knockdown of IRAK1 produced more robust apoptotic effects versus IRAK4. FIG. 1B shows that JH-X-119-01 inhibited IRAK1 biochemically with an IC50 of 9.3 nM, while exhibiting no inhibition of IRAK4 at concentrations up to 10 µM, and showed exceptional kinome selectivity with off-target inhibition of only two kinases, YSK4 and MEK3. FIG. 1C shows the effect of the combination of JH-X-119-01 with Ibrutinib leading to synergistic tumor cell killing in MYD88 mutated Waldenstrom's macroglobulinemia (WM) and ABC-DLBCL cells, and suppression of NF-κB activation.

FIG. 4. In vitro kinase inhibition for IRAK1 inhibitors.

DETAILED DESCRIPTION OF CERTAIN EMBODIMENTS OF THE INVENTION

Figure 1A:
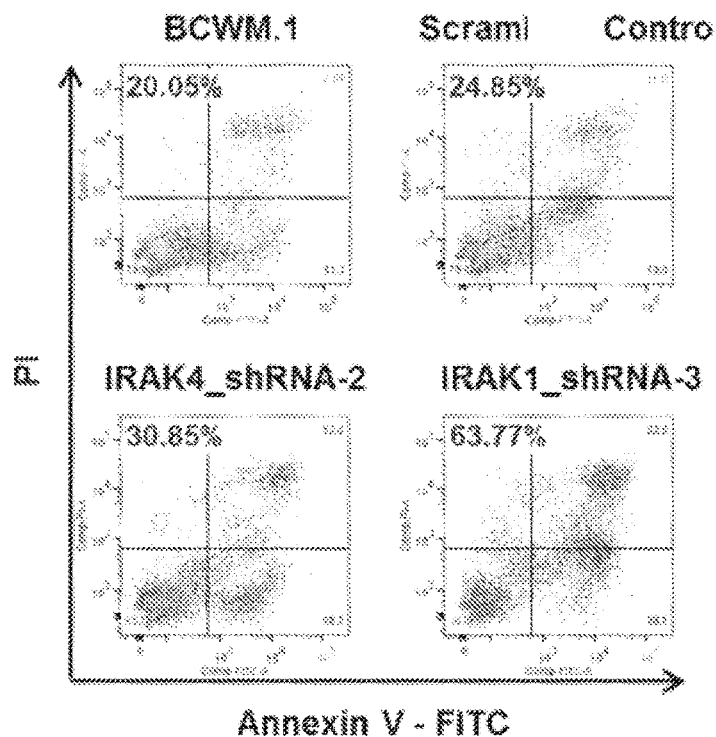

The present invention provides selective IRAK1 and/or IRAK4 inhibitors, which covalently modify a cysteine residue (e.g., Cys302) of IRAK1. Selective covalent inhibitors of these kinases may be useful in the treatment of various proliferative diseases including cancer.

The present invention provides compounds, which inhibit the activity of a kinase (e.g., IRAK), for the prevention and/or treatment of a subject with a proliferative disease. In certain embodiments, the inventive compounds inhibit the activity of an interleukin-1 receptor-associated kinase (IRAK). In certain embodiments, the inventive compounds inhibit the activity of an interleukin-1 receptor-associated kinase 1 (IRAK1). In certain embodiments, the inventive compounds inhibit the activity of an interleukin-1 receptor-associated kinase 4 (IRAK4). In certain embodiments, the inventive compounds covalently modify an interleukin-1 receptor-associated kinase 1 (IRAK1). In certain embodiments, the inventive compounds covalently modify an interleukin-1 receptor-associated kinase 4 (IRAK4). The present invention also provides methods of using the compounds described herein, e.g., as biological probes to study the inhibition of the activity of a kinase (e.g., IRAK (e.g. IRAK1 and/or IRAK4)), and as therapeutics, e.g., in the prevention and/or treatment of diseases associated with the overexpression, increased activity, and/or aberrant activity of a kinase (e.g., IRAK (e.g. IRAK1 and/or IRAK4)). In certain embodiments, the diseases are proliferative diseases. The proliferative diseases that may be treated and/or prevented include, but are not limited to, (e.g., cancers (e.g., leukemia, lymphoma), inflammatory diseases, autoinflammatory diseases, and autoimmune diseases. Also provided by the present disclosure are pharmaceutical compositions, kits, methods, and uses including a compound of Formula (I') as described herein.

Compounds

Aspects of the present disclosure relate to the compounds described herein. The compounds described herein may be useful in treating and/or preventing proliferative diseases in a subject, or inhibiting the activity of a protein kinase (e.g., IRAK) in a subject or biological sample. In certain embodiments, a compound described herein is a compound of any one of Formula (I'), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I'), or a pharmaceutically acceptable salt thereof.

In certain embodiments, a compound described herein is of Formula (I'):

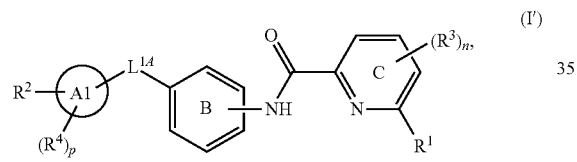
(I')

or a pharmaceutically acceptable salt, solvate, hydrate, tautomer, or stereoisomer thereof, wherein:

$R^1$ is an optionally substituted monocyclic heteroaryl ring;

$R^2$ is a warhead of formula:

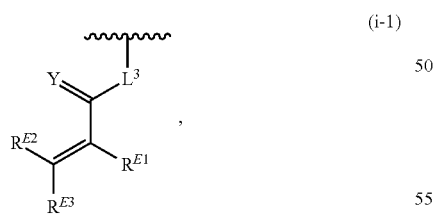
(i-1)

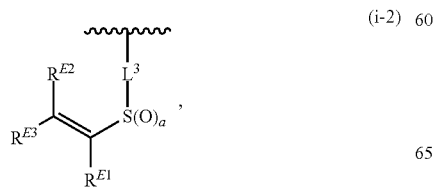
(i-2)

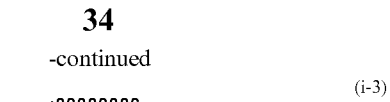
(i-3)

(i-4)

(i-5)

(i-6)

(i-7)

(i-8)

(i-9)

(i-10)

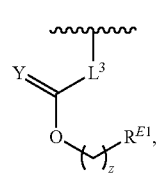 (i-11)
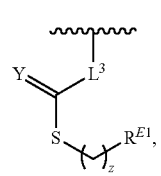 (i-12)
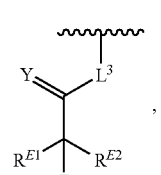 (i-13)
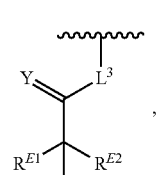 (i-14)
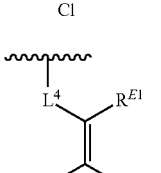 (i-15)
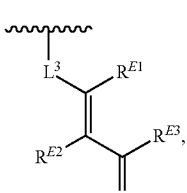 (i-16)
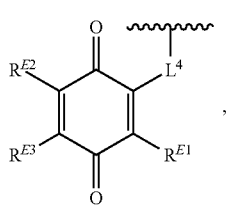 (i-17)
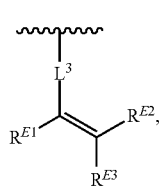 (i-18)
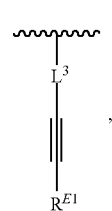 (i-19)
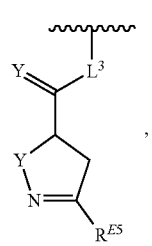 (i-20)
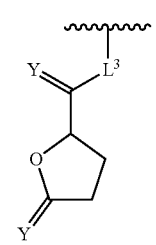 (i-21)
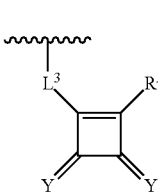 (i-22)
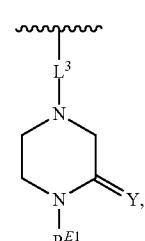 (i-23)
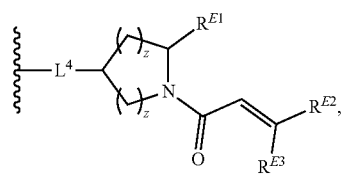 (i-24)
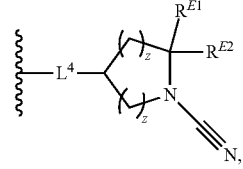 (i-25)

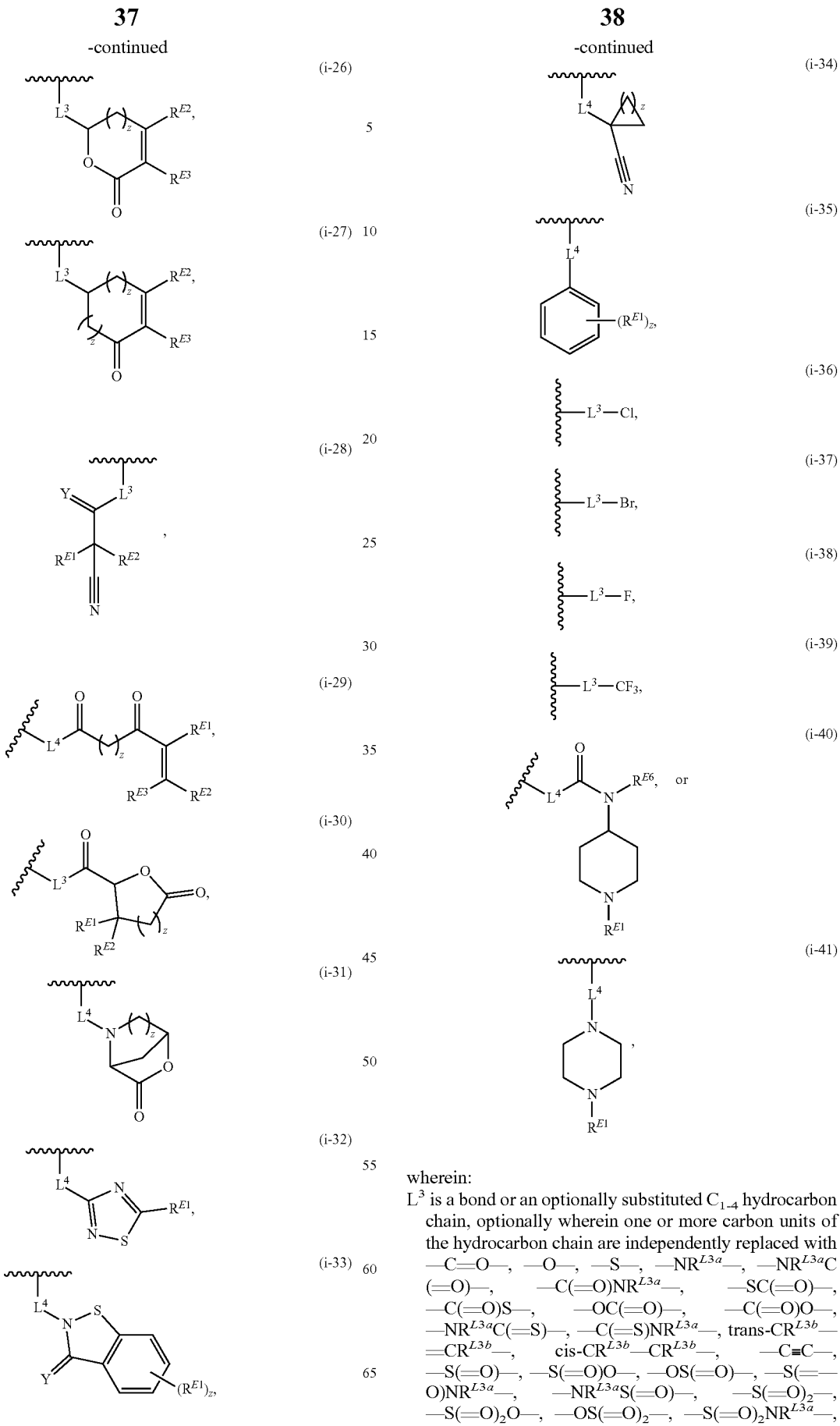

wherein:
L³ is a bond or an optionally substituted C₁₋₄ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)₂—, —S(=O)₂O—, —OS(=O)₂—, —S(=O)₂NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$), —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2;

each instance of z is independently 0, 1, 2, 3, 4, 5, or 6, as valency permits;

L$^{1A}$ is $^{1a}$—NR$^{L1}$C(=O)—$^{1b}$, $^{1a}$—C(=O)NR$^{L1}$-$^{1b}$, or an unsubstituted 5-membered heteroaryl ring; wherein $^{1a}$ indicates the point of attachment is to Ring A; and $^{1b}$ indicates the point of attachment is to Ring B;

each instance of R$^3$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of R$^{D1a}$ are taken together with their intervening atoms to form a substituted or unsubstituted heterocyclic or substituted or unsubstituted heteroaryl ring;

or two R$^3$ groups are joined to form an optionally substituted carbocyclyl, optionally substituted heterocyclyl, optionally substituted aryl, or optionally substituted heteroaryl ring;

each instance of R$^4$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$;

R$^{L1}$ is independently hydrogen, optionally substituted C$_{1-6}$ alkyl, or a nitrogen protecting group;

Ring A1 is optionally substituted carbocyclyl, optionally substituted phenyl, optionally substituted 5-membered heterocyclyl, or optionally substituted 6-membered heterocyclyl;

n is 0, 1, 2, or 3; and p is 0, 1, 2, 3, or 4.

In certain embodiments, the compound of Formula (I') is of Formula (I).

In certain embodiments, a compound described herein is of Formula (I):

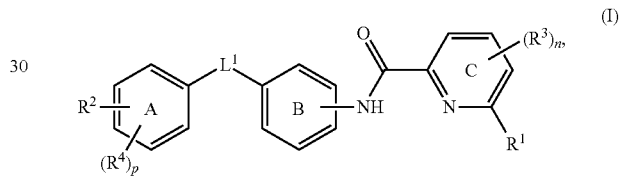

(I)

or a pharmaceutically acceptable salt, solvate, hydrate, tautomer, or stereoisomer thereof, wherein:

R$^1$ is an optionally substituted monocyclic heteroaryl ring;

R$^2$ is a warhead of formula:

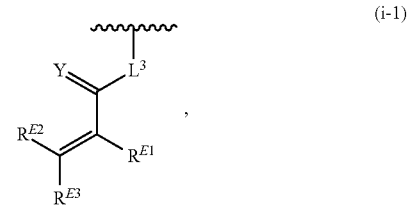

(i-1)

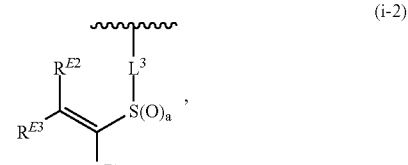

(i-2)

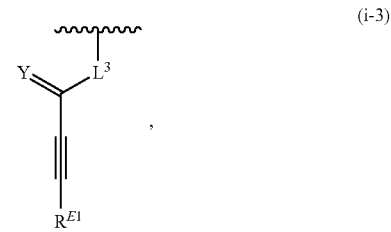

(i-3)

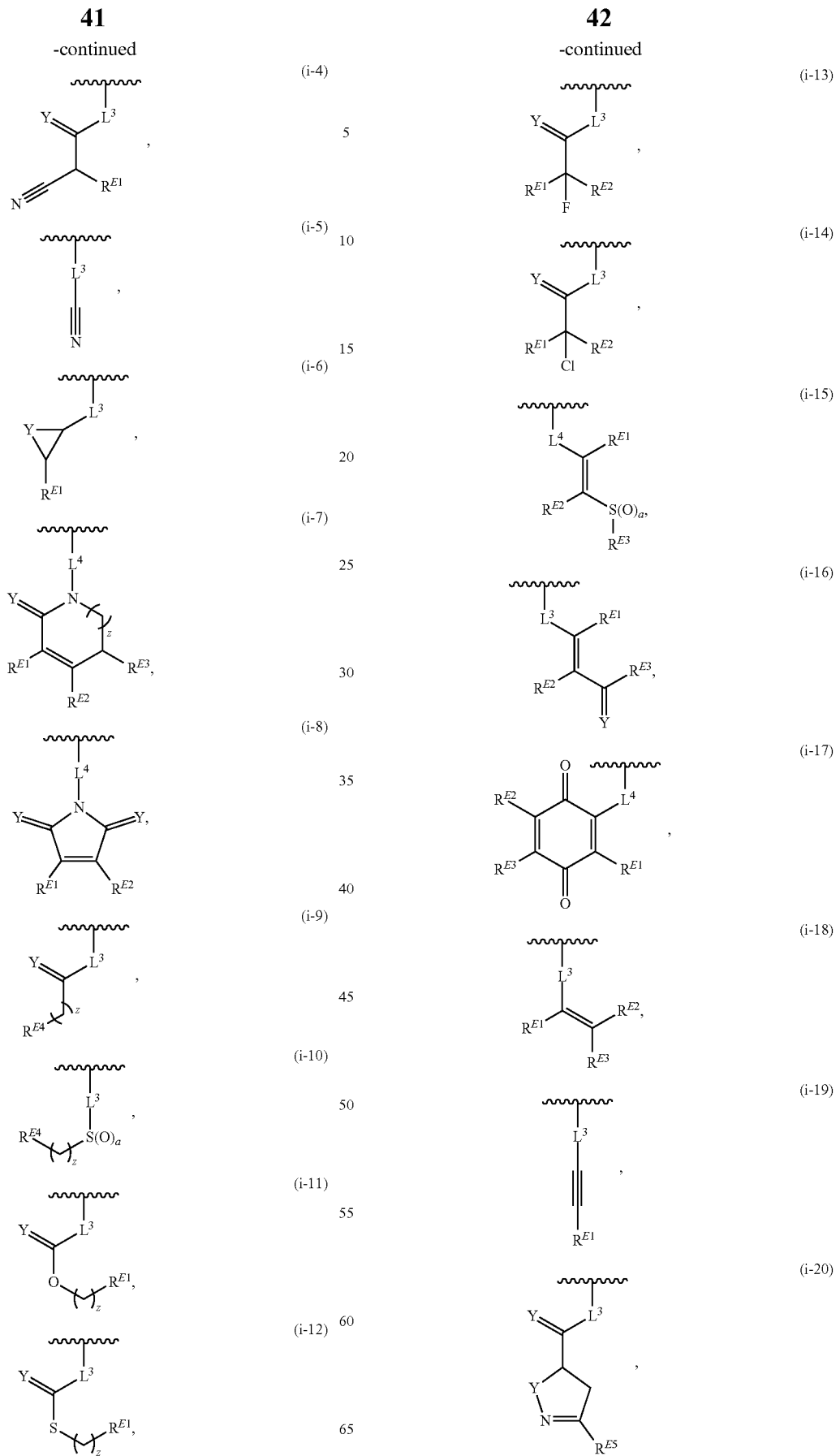

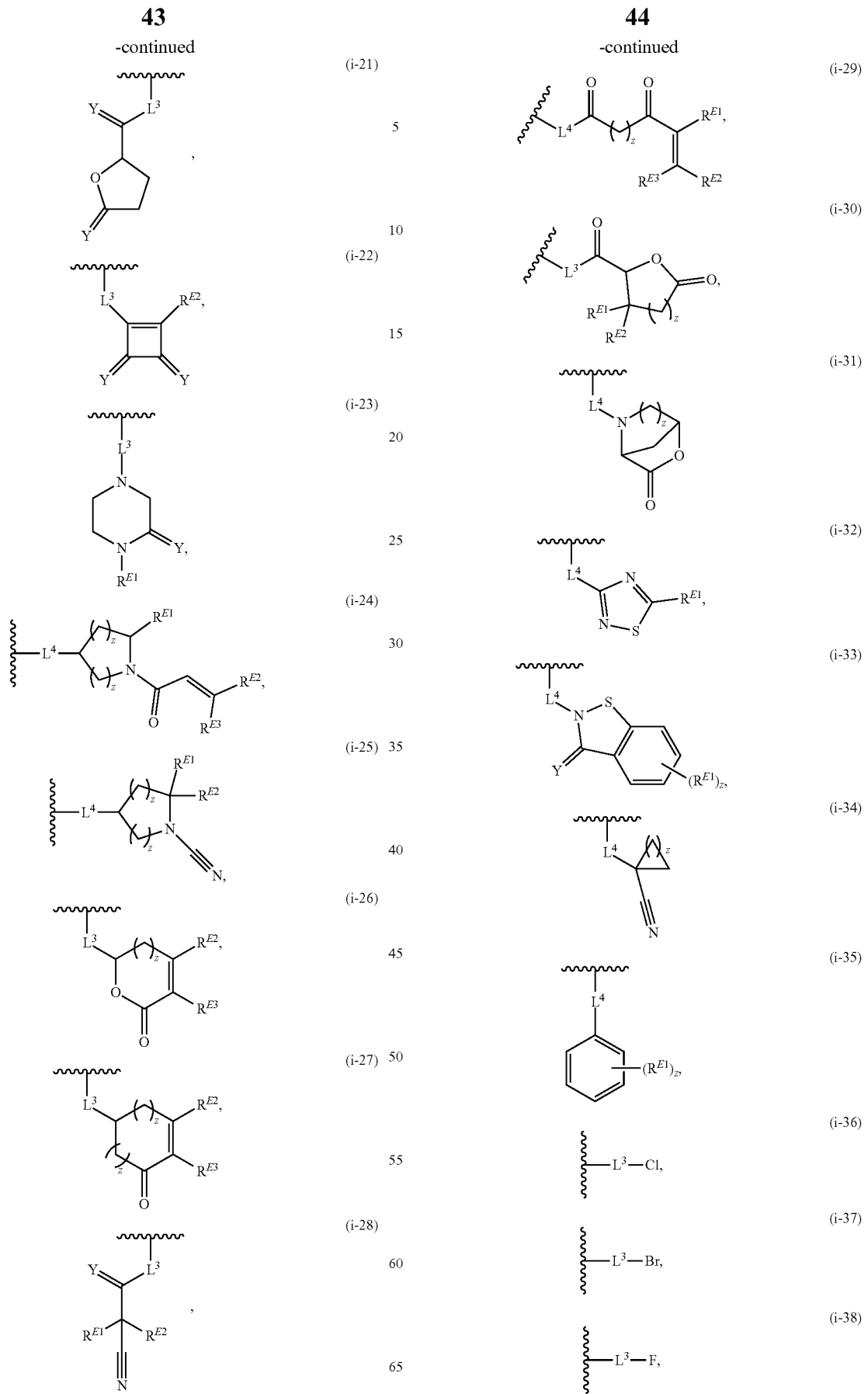

-continued (i-39)

$\mathrm{-L^3-CF_3,}$ (i-40)

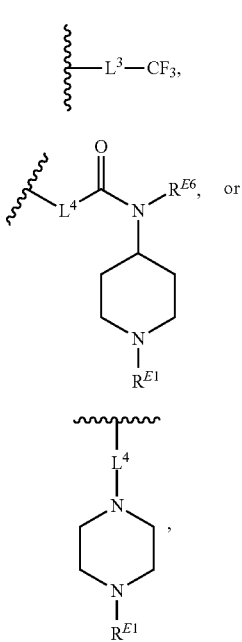

(i-41)

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$), —CH$_2$SR$^{EE}$, —OR$^{EE}$, —N(R$^{EE}$), —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits;

$L^1$ is i-NR$^L$C(=O)—$^{1b}$ or a 5-membered heteroaryl ring; wherein i indicates the point of attachment to Ring A; and $^{1b}$ indicates the point of attachment to Ring B;

each instance of R$^3$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein R$^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, a nitrogen protecting group, or optionally two instances of R$^{D1a}$ are taken together with their intervening atoms to form a substituted or unsubstituted heterocyclic or substituted or unsubstituted heteroaryl ring;

or two R$^3$ groups are joined to form an optionally substituted carbocyclyl, optionally substituted heterocyclyl, optionally substituted aryl, or optionally substituted heteroaryl ring;

each instance of R$^4$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$;

R$^{L1}$ is independently hydrogen, optionally substituted $C_{1-6}$ alkyl, or a nitrogen protecting group;

n is 0, 1, 2, or 3; and p is 0, 1, 2, 3, or 4.

Formulae (I) and (I') include substituent R$^1$. As generally defined herein, R$^1$ is an optionally substituted monocyclic heteroaryl ring. In certain embodiments, R$^1$ is an optionally substituted 5-membered heteroaryl ring. In certain embodiments, R$^1$ is of Formula (ii-5):

(ii-5)

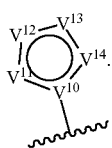

In certain embodiments, $V^{10}$, $V^{11}$, $V^{12}$, $V^{13}$, and $V^{14}$ of $R^1$ may each independently be O, S, N, $NR^{A1}$, C, or $CR^{A2}$, as valency permits. In certain embodiments, only one of $V^{10}$, $V^{11}$, $V^{12}$, $V^{13}$, and $V^{14}$ is selected from the group consisting of O, S, N, and $NR^{A1}$. In certain embodiments, $R^1$ is of formula:

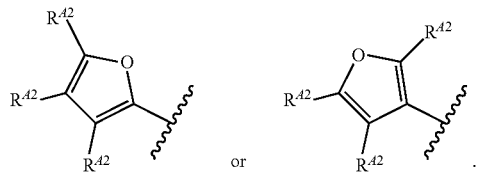

In certain embodiments, $R^1$ is of formula:

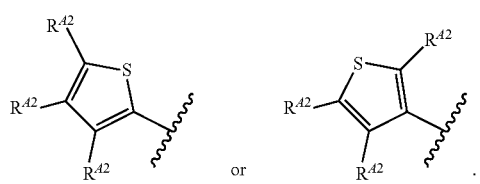

In certain embodiments, $R^1$ is of formula:

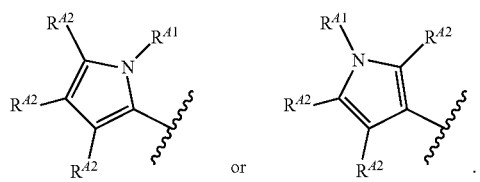

In certain embodiments, only two of $V^{10}$, $V^{11}$, $V^{12}$, $V^{13}$, and $V^{14}$ are each independently selected from the group consisting of O, S, N, and $NR^{A1}$. In certain embodiments, $R^1$ is optionally substituted thiazole. In certain embodiments, $R^1$ is optionally substituted oxazole. In certain embodiments, $R^1$ is optionally substituted imidazole. In certain embodiments, $R^1$ is optionally substituted pyrazole. In certain embodiments, $R^1$ is optionally substituted isoxazole.

In certain embodiments, $R^1$ is of formula:

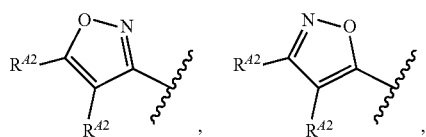

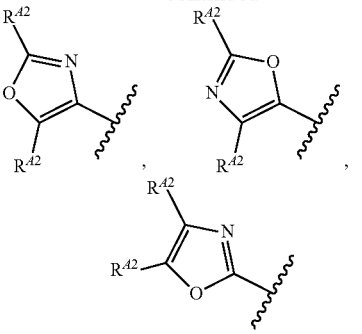

In certain embodiments, $R^1$ is of formula:

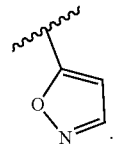

In certain embodiments, $R^1$ is of formula:

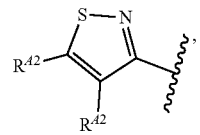

In certain embodiments, $R^1$ is of formula:

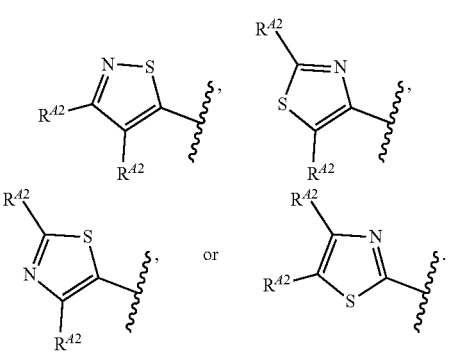

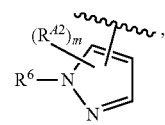

wherein $R^{A2}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A2a}$, —$N(R^{A2b})_2$, —$SR^{A2a}$; each occurrence of $R^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, an oxygen protecting group when attached to an oxygen atom, and a sulfur protecting group when attached to a sulfur atom; each occurrence of $R^{A2b}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, and a nitrogen protecting group; or optionally two instances of $R^{A2b}$ are taken together with their intervening atoms to form a substituted or unsubstituted heterocyclic or substituted or unsubstituted heteroaryl ring; $R^6$ is hydrogen, optionally substituted acyl, optionally substituted alkyl, or a nitrogen protecting group; and m is 0, 1, 2, or 3. In certain embodiments, $R^1$ is of formula:

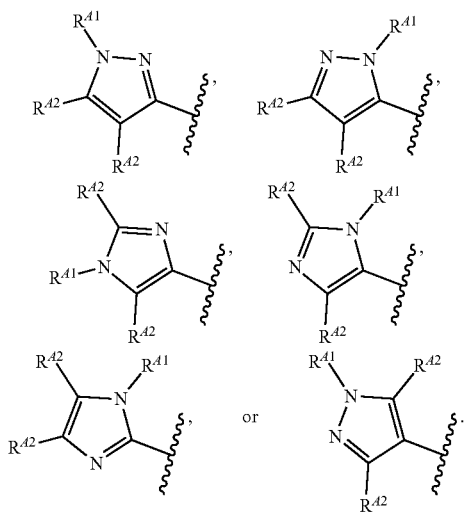

In certain embodiments, $R^{41}$ is $R^6$. In certain embodiments, $R^{41}$ is hydrogen, optionally substituted acyl, optionally substituted alkyl, or a nitrogen protecting group. In certain embodiments, $R^{41}$ is optionally substituted $C_{1-6}$ alkyl. In certain embodiments, $R^{41}$ is optionally substituted methyl. In certain embodiments, $R^{41}$ is unsubstituted methyl. In certain embodiments, $R^{41}$ is substituted methyl. In certain embodiments, $R^1$ is of formula

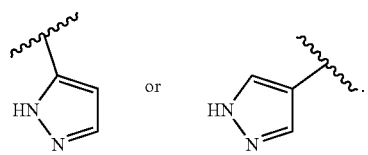 [SMILES: *c1ccn[nH]1 ; *c1cn[nH]c1]

In certain embodiments, $R^1$ is of formula

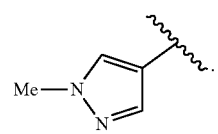 [SMILES: *c1cnn(C)c1]

In certain embodiments, only three of $V^{10}$, $V^{11}$, $V^{12}$, $V^{13}$, and $V^{14}$ are each independently selected from the group consisting of O, S, N, and $NR^{41}$. In certain embodiments, $R^1$ is of formula:

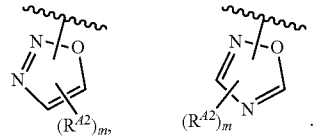

In certain embodiments, $R^1$ is of formula:

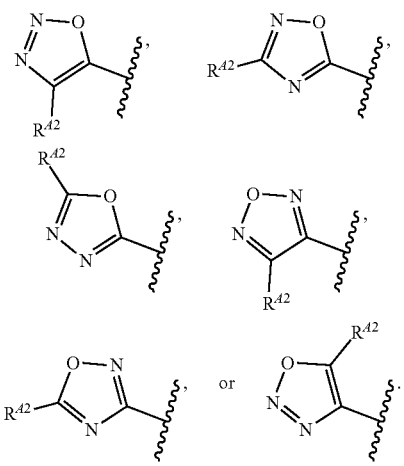

In certain embodiments, $R^1$ is of formula:

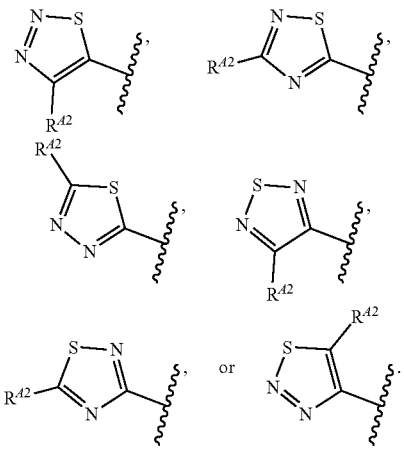

In certain embodiments, $R^1$ is of formula:

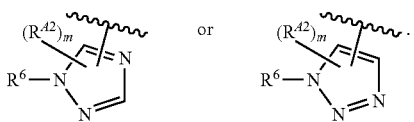

In certain embodiments, $R^1$ is of formula:

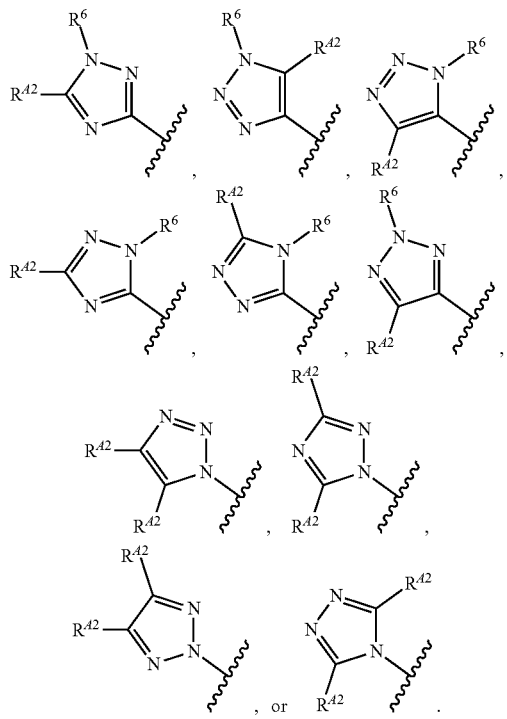

In certain embodiments, $R^6$ is hydrogen. In certain embodiments, $R^6$ is substituted or unsubstituted acyl (e.g., —C(=O)Me). In certain embodiments, $R^6$ is substituted or unsubstituted alkyl (e.g., substituted or unsubstituted $C_{1-6}$ alkyl). In certain embodiments, $R^6$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, $R^1$ is an optionally substituted 6-membered heteroaryl ring. In certain embodiments, $R^1$ is of the formula:

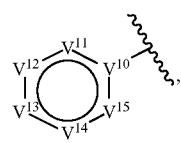

wherein each of $V^{10}$, $V^{11}$, $V^{12}$, $V^{13}$, $V^{14}$, and $V^{15}$ is independently N, C, or $CR^{42}$, as valency permits, wherein $R^{42}$ is as defined herein. In certain embodiments, only one of $V^{10}$, $V^{11}$, $V^{12}$, $V^{13}$, $V^{14}$, and $V^{15}$ is N. In certain embodiments, $R^1$ is of the formula:

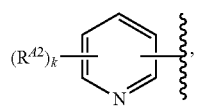

wherein k is 0, 1, 2, 3, or 4, and $R^{42}$ is as defined herein. In certain embodiments, $R^1$ is of the formula:

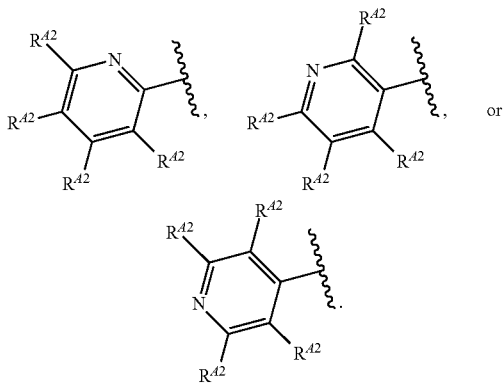

In certain embodiments, $R^1$ is of the formula:

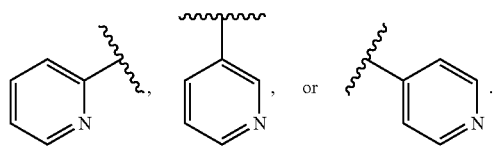 [SMILES: *c1ccccn1 ; *c1cccnc1 ; *c1ccncc1]

In certain embodiments, $R^1$ is of the formula:

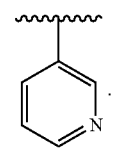

In certain embodiments, only three of $V^{10}$, $V^{11}$, $V^{12}$, $V^{13}$, $V^{14}$, and $V^{15}$ are N. In certain embodiments, $R^1$ is of the formula:

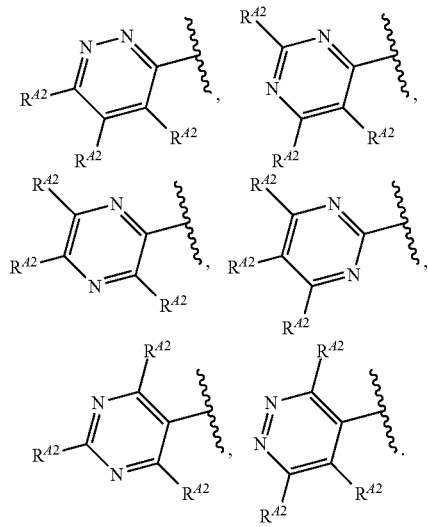

In certain embodiments, only three of $V^{10}$, $V^{11}$, $V^{12}$, $V^{13}$, $V^{14}$, and $V^{15}$ are N. In certain embodiments, $R^1$ is of the formula:

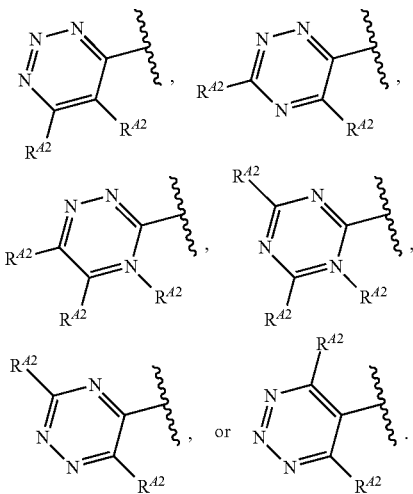

In certain embodiments, only three of $V^{10}$, $V^{11}$, $V^{12}$, $V^{13}$, $V^{14}$, and $V^{15}$ are N. In certain embodiments, $R^1$ is of formula:

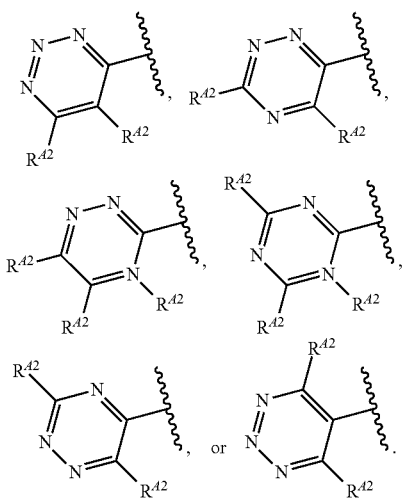

In certain embodiments, $R^1$ is of formula:

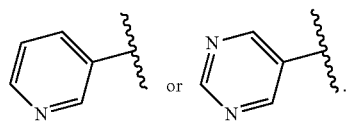 [SMILES: *c1cccnc1 ; *c1cncnc1]

In certain embodiments, $R^1$ includes zero or more instances of $R^{42}$. In certain embodiments, m is 0. In certain embodiments, m is 1. In certain embodiments, m is 2. In certain embodiments, m is 3. In certain embodiments, at least one instance of $R^{42}$ is hydrogen. In certain embodiments, at least one instance of $R^{42}$ is substituted or unsubstituted acyl (e.g., —C(=O)Me). In certain embodiments, at least one instance of $R^{42}$ is halogen (e.g., F, Cl, Br, or I). In certain embodiments, at least one $R^{42}$ is substituted or unsubstituted alkyl (e.g., substituted or unsubstituted $C_{1-6}$ alkyl). In certain embodiments, at least one instance of $R^{42}$ is substituted or unsubstituted methyl. In certain embodiments, at least one instance of $R^{42}$ is substituted or unsubstituted ethyl. In certain embodiments, at least one instance of $R^{42}$ is substituted or unsubstituted propyl. In certain embodiments, at least one instance of $R^{42}$ is substituted or unsubstituted alkenyl (e.g., substituted or unsubstituted $C_{2-6}$ alkenyl). In certain embodiments, at least one instance of $R^{42}$ is substituted or unsubstituted alkynyl (e.g., substituted or unsubstituted $C_{2-6}$ alkynyl). In certain embodiments, at least one instance of $R^{42}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{42}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{42}$ is substituted or unsubstituted aryl (e.g., substituted or unsubstituted, 6- to 10-membered aryl). In certain embodiments, at least one instance of $R^{42}$ is benzyl. In certain embodiments, at least one instance of $R^{42}$ is substituted or unsubstituted phenyl. In certain embodiments, at least one instance of $R^{42}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{42}$ is —$OR^{42a}$ (e.g., —OH or —OMe). In certain embodiments, at least one instance of $R^{42}$ is —$N(R^{42b})_2$ (e.g., —$NMe_2$). In certain embodiments, at least one instance of $R^{42}$ is —$SR^{42a}$ (e.g., —SMe).

In certain embodiments, at least one instance of $R^{42a}$ is hydrogen. In certain embodiments, at least one instance of $R^{42a}$ is substituted or unsubstituted acyl (e.g., —C(=O)Me). In certain embodiments, at least one $R^{42a}$ is substituted or unsubstituted alkyl (e.g., substituted or unsubstituted $C_{1-6}$ alkyl). In certain embodiments, at least one instance of $R^{42a}$ is substituted or unsubstituted methyl. In certain embodiments, at least one instance of $R^{42a}$ is substituted or unsubstituted ethyl. In certain embodiments, at least one instance of $R^{42a}$ is substituted or unsubstituted propyl. In certain embodiments, at least one instance of $R^{42a}$ is substituted or unsubstituted alkenyl (e.g., substituted or unsubstituted $C_{2-6}$ alkenyl). In certain embodiments, at least one instance of $R^{42a}$ is substituted or unsubstituted alkynyl (e.g., substituted or unsubstituted $C_{2-6}$ alkynyl). In certain embodiments, at least one instance of $R^{42a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{42a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{42a}$ is substituted or unsubstituted aryl (e.g., substituted or unsubstituted, 6- to 10-membered aryl). In certain embodiments, at least one instance of $R^{42a}$ is benzyl. In certain embodiments, at least one instance of $R^{4a2}$ is substituted or unsubstituted phenyl. In certain embodiments, at least one instance of $R^{42a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A2a}$ is an oxygen protecting group when attached to an oxygen atom. In certain embodiments, at least one instance of $R^{A2a}$ is a sulfur protecting group when attached to a sulfur atom.

In certain embodiments, at least one instance of $R^{A2b}$ is hydrogen. In certain embodiments, at least one instance of $R^{A2b}$ is substituted or unsubstituted acyl (e.g., —C(=O)Me). In certain embodiments, at least one $R^{A2b}$ is substituted or unsubstituted alkyl (e.g., substituted or unsubstituted $C_{1-6}$ alkyl). In certain embodiments, at least one instance of $R^{A2b}$ is substituted or unsubstituted methyl. In certain embodiments, at least one instance of $R^{A2b}$ is substituted or unsubstituted ethyl. In certain embodiments, at least one instance of $R^{A2b}$ is substituted or unsubstituted propyl. In certain embodiments, at least one instance of $R^{A2b}$ is substituted or unsubstituted alkenyl (e.g., substituted or unsubstituted $C_{2-6}$ alkenyl). In certain embodiments, at least one instance of $R^{A2b}$ is substituted or unsubstituted alkynyl (e.g., substituted or unsubstituted $C_{2-6}$ alkynyl). In certain embodiments, at least one instance of $R^{A2b}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A2b}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A2b}$ is substituted or unsubstituted aryl (e.g., substituted or unsubstituted, 6- to 10-membered aryl). In certain embodiments, at least one instance of $R^{A2b}$ is benzyl. In certain embodiments, at least one instance of $R^{A2b}$ is substituted or unsubstituted phenyl. In certain embodiments, at least one instance of $R^{A2b}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A2b}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, orp-toluenesulfonamide (Ts)). In certain embodiments, two instances of $R^{A2b}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

As generally defined herein, Formulae (I') and (I) include substituent $R^2$, wherein $R^2$ is a warhead of formula:

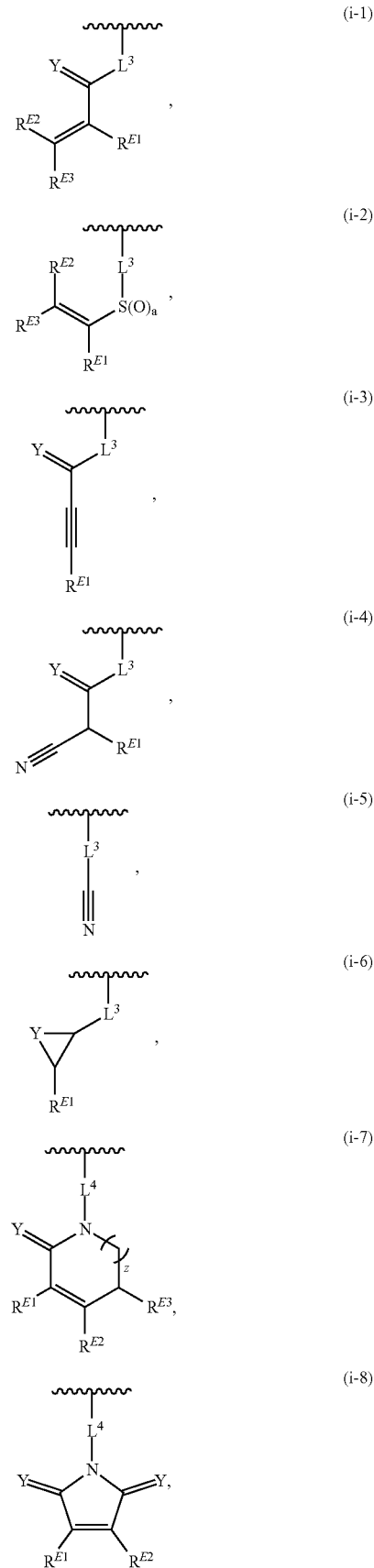

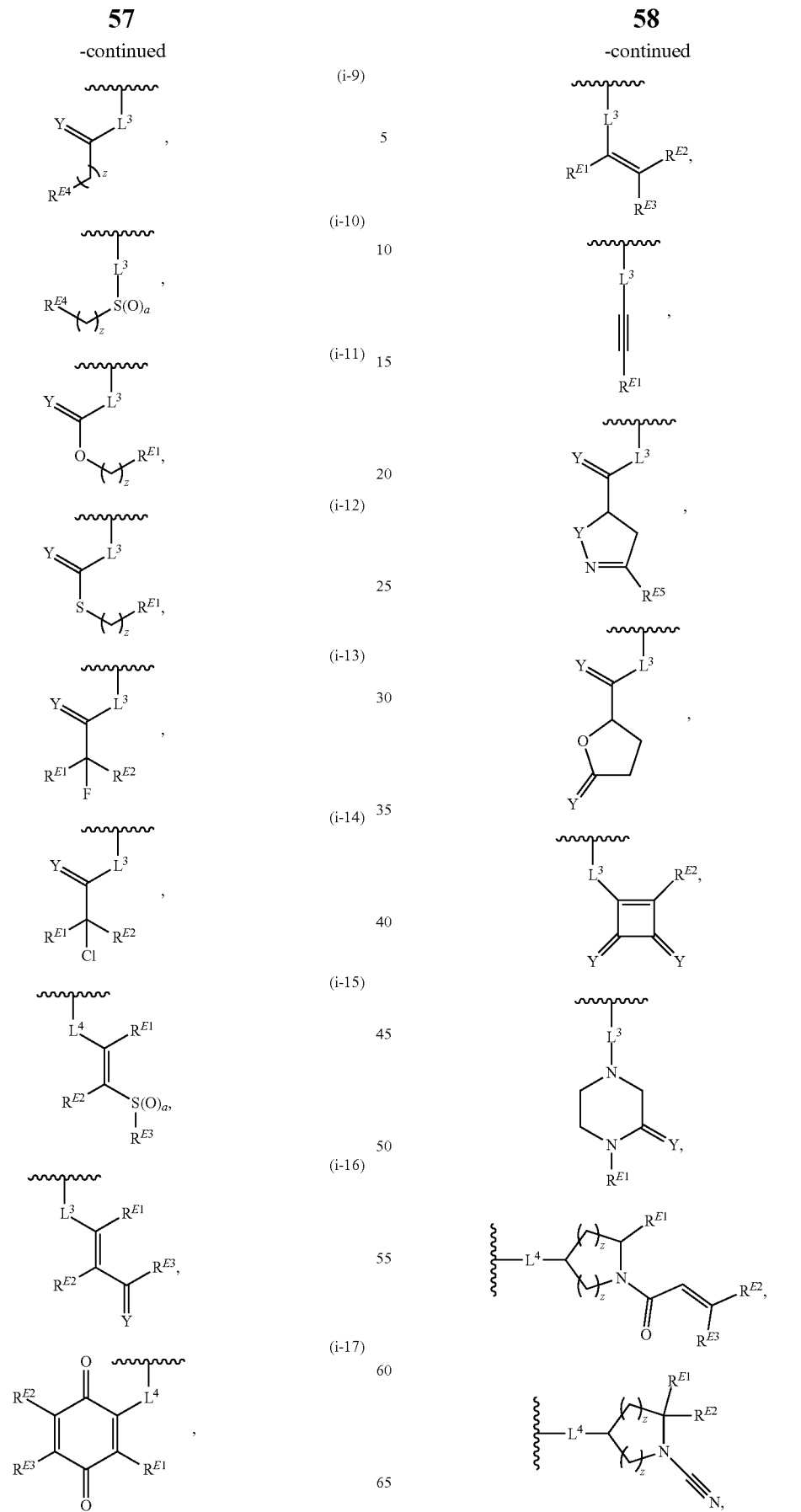

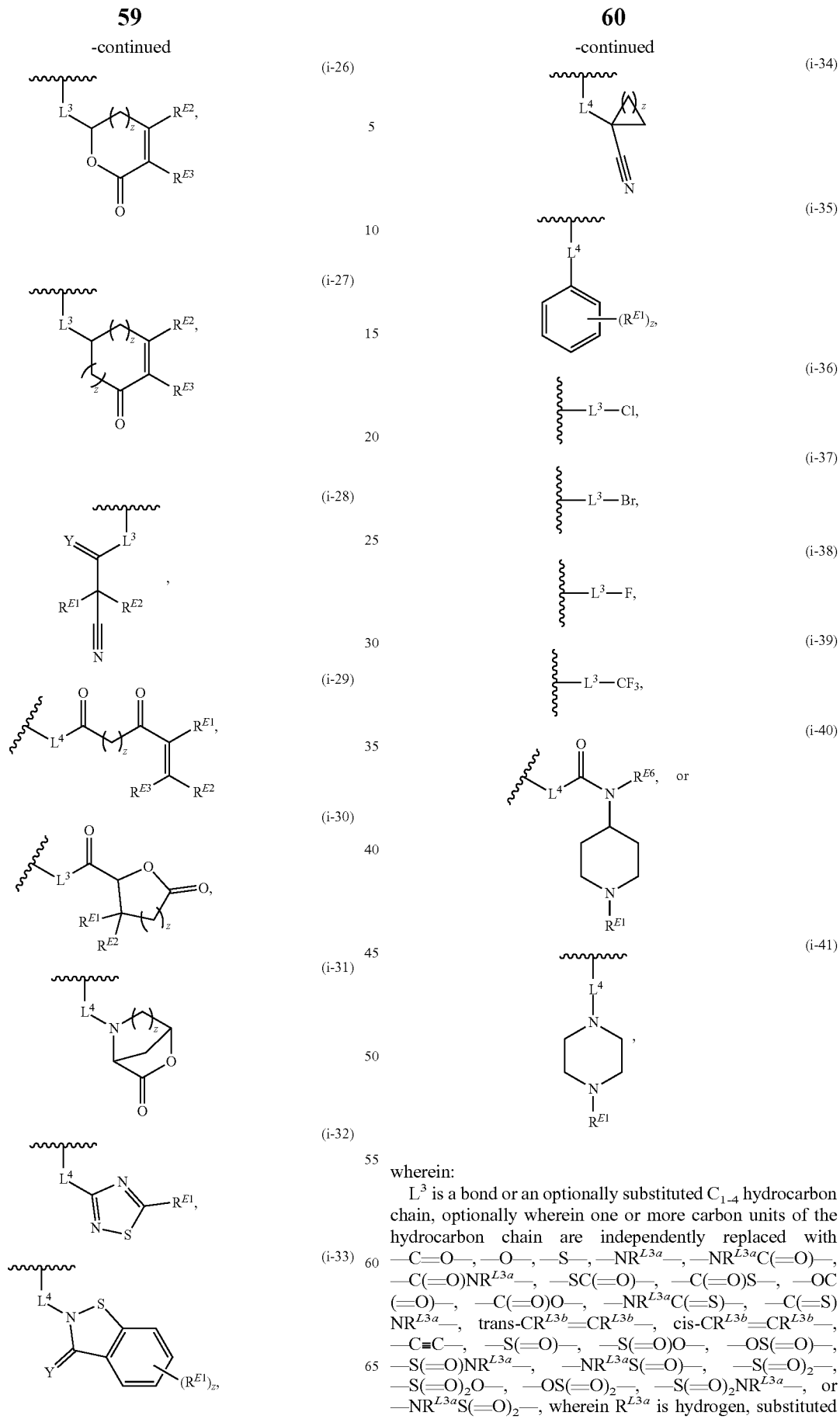

wherein:
L³ is a bond or an optionally substituted C₁₋₄ hydrocarbon chain, optionally wherein one or more carbon units of the hydrocarbon chain are independently replaced with —C=O—, —O—, —S—, —NR^{L3a}—, —NR^{L3a}C(=O)—, —C(=O)NR^{L3a}—, —SC(=O)—, —C(=O)S—, —OC(=O)—, —C(=O)O—, —NR^{L3a}C(=S)—, —C(=S)NR^{L3a}—, trans-CR^{L3b}=CR^{L3b}—, cis-CR^{L3b}=CR^{L3b}—, —C≡C—, —S(=O)—, —S(=O)O—, —OS(=O)—, —S(=O)NR^{L3a}—, —NR^{L3a}S(=O)—, —S(=O)₂—, —S(=O)₂O—, —OS(=O)₂—, —S(=O)₂NR^{L3a}—, or —NR^{L3a}S(=O)₂—, wherein R^{L3a} is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring; $L^4$ is a bond or an optionally substituted, branched or unbranched $C_{1-6}$ hydrocarbon chain; each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring; or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring; $R^{E4}$ is a leaving group; $R^{E5}$ is halogen; $R^{E6}$ is hydrogen, substituted or unsubstituted $C_{1-6}$ alkyl, or a nitrogen protecting group; each instance of Y is independently O, S, or NR$^{E7}$, wherein $R^{E7}$ is hydrogen, substituted or unsubstituted $C_{1-6}$ alkyl, or a nitrogen protecting group; a is 1 or 2; and each instance of z is independently 0, 1, 2, 3, 4, 5, or 6, as valency permits.

In certain embodiments, $R^2$ is a warhead of formula (i-1) through (i-41). In certain embodiments, the warhead is of formula:

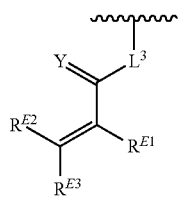
(i-1)

In certain embodiments, $R^2$ is a warhead of formula:

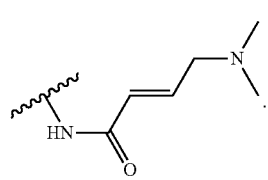 [SMILES: *NC(=O)/C=C/CN(C)C]

In certain embodiments, $R^2$ is a warhead of formula:

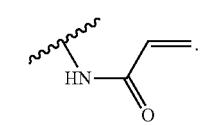 [SMILES: *NC(=O)C=C]

In certain embodiments, $R^2$ is a warhead of formula:

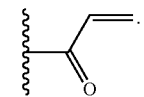 [SMILES: *C(=O)C=C]

In certain embodiments, the warhead is of formula:

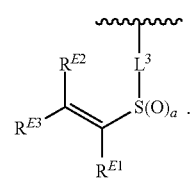
(i-2)

In certain embodiments, the warhead is of formula:

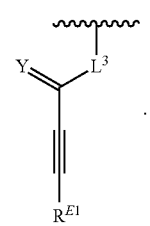
(i-3)

In certain embodiments, the warhead is of formula:

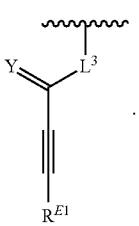
(i-4)

In certain embodiments, the warhead is of formula:

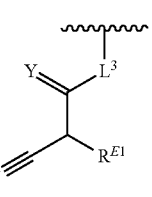
(i-5)

In certain embodiments, the warhead is of formula:

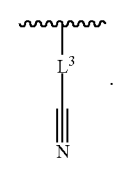
(i-6)

In certain embodiments, the warhead is of formula:

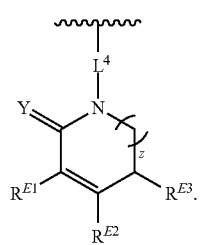

(i-7)

In certain embodiments, the warhead is of formula:

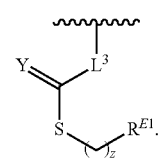

(i-12)

In certain embodiments, the warhead is of formula:

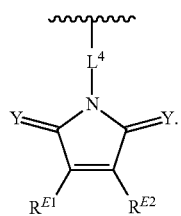

(i-8)

In certain embodiments, the warhead is of formula:

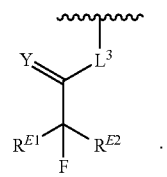

(i-13)

In certain embodiments, the warhead is of formula:

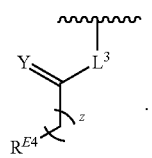

(i-9)

In certain embodiments, the warhead is of formula:

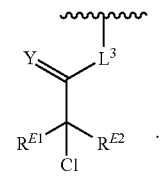

(i-14)

In certain embodiments, the warhead is of formula:

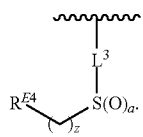

(i-10)

In certain embodiments, the warhead is of formula:

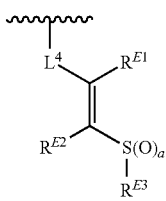

(i-15)

In certain embodiments, the warhead is of formula:

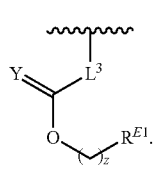

(i-11)

In certain embodiments, the warhead is of formula:

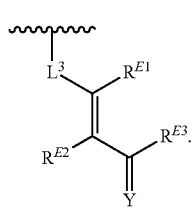

(i-16)

In certain embodiments, the warhead is of formula:

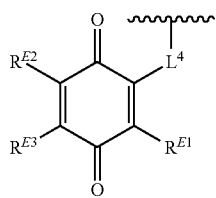 (i-17)

In certain embodiments, the warhead is of formula:

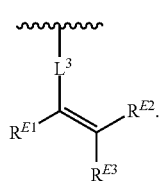 (i-18)

In certain embodiments, the warhead is of formula:

 (i-19)

In certain embodiments, the warhead is of formula:

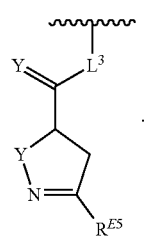 (i-20)

In certain embodiments, the warhead is of formula:

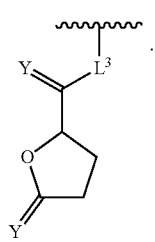 (i-21)

In certain embodiments, the warhead is of formula:

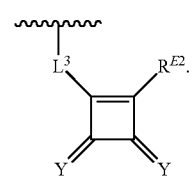 (i-22)

In certain embodiments, the warhead is of formula:

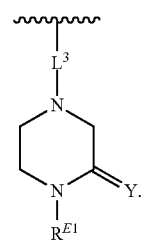 (i-23)

In certain embodiments, the warhead is of formula:

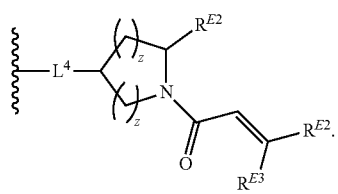 (i-24)

In certain embodiments, the warhead is of formula:

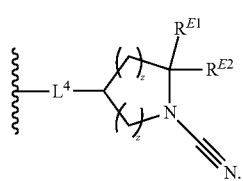 (i-25)

In certain embodiments, the warhead is of formula:

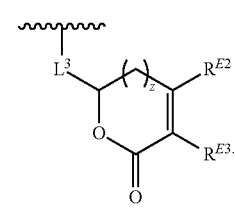 (i-26)

In certain embodiments, the warhead is of formula:

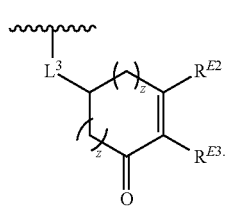

(i-27)

In certain embodiments, the warhead is of formula:

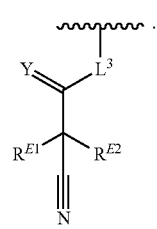

(i-28)

In certain embodiments, the warhead is of formula:

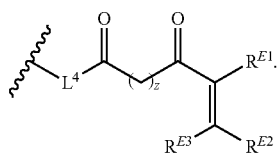

(i-29)

In certain embodiments, the warhead is of formula:

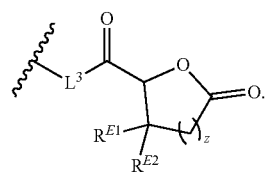

(i-30)

In certain embodiments, the warhead is of formula:

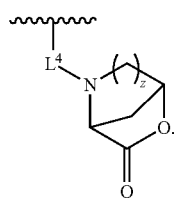

(i-31)

In certain embodiments, the warhead is of formula:

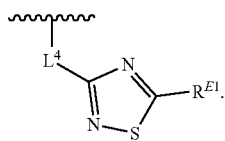

(i-32)

In certain embodiments, the warhead is of formula:

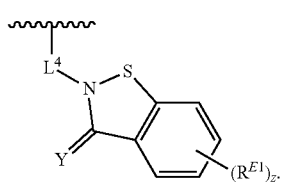

(i-33)

In certain embodiments, the warhead is of formula:

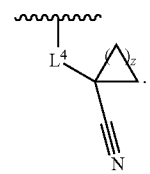

(i-34)

In certain embodiments, the warhead is of formula:

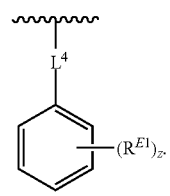

(i-35)

In certain embodiments, the warhead is of formula:

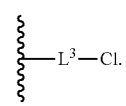

(i-36)

In certain embodiments, the warhead is of formula:

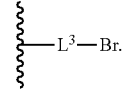

(i-37)

In certain embodiments, the warhead is of formula:

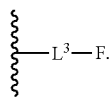

(i-38)

In certain embodiments, the warhead is of formula:

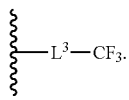

(i-39)

In certain embodiments, the warhead is of formula:

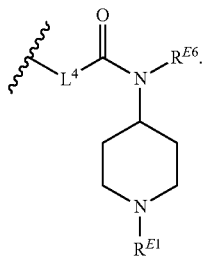

(i-40)

In certain embodiments, the warhead is of formula:

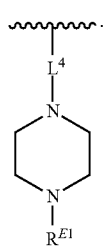

(i-41)

In certain embodiments, $L^3$ is a bond (e.g., a single bond, a double bond, a triple bond). In certain embodiments, $L^3$ is a single bond. In certain embodiments, $L^3$ is a double bond. In certain embodiments, $L^3$ is a triple bond. In certain embodiments, $L^3$ is an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring. In certain embodiments, $L^4$ is a bond (e.g., a single bond, a double bond, or a triple bond). In certain embodiments, $L^4$ is an optionally substituted branched $C_{1-6}$ hydrocarbon chain (e.g., i-Pr). In certain embodiments, $L^4$ is an optionally substituted unbranched $C_{1-6}$ hydrocarbon chain (e.g., n-Pr, or n-Bu). In certain embodiments, at least one instance of R$^{E1}$ is H. In certain embodiments, at least one instance of R$^{E1}$ is halogen (e.g., F, Cl, Br, or I). In certain embodiments, at least one instance of R$^{E1}$ is optionally substituted alkyl (e.g., Me, or Et). In certain embodiments, at least one instance of R$^{E1}$ is optionally substituted alkenyl (e.g., optionally substituted vinyl). In certain embodiments, at least one instance of R$^{E1}$ is optionally substituted alkynyl. In certain embodiments, at least one instance of R$^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of R$^{E1}$ is substituted or unsubstituted aryl (e.g., substituted or unsubstituted, 6- to 10-membered aryl). In certain embodiments, at least one instance of R$^{E1}$ is substituted or unsubstituted phenyl. In certain embodiments, at least one instance of R$^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of R$^{E1}$ is —CN. In certain embodiments, at least one instance of R$^{E1}$ is —CH$_2$OR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^{E1}$ is —CH$_2$N(R$^{EF}$)$_2$ or —N(R$^{EF}$)$_2$, wherein each instance of REF is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two R$^{EF}$ groups are joined to form an optionally substituted heterocyclic ring. In certain embodiments, at least one instance of R$^{E1}$ is —CH$_2$SR$^{EE}$ or —SR$^{EE}$ (e.g., —CH$_2$SMe or —SMe). In certain embodiments, at least one instance of R$^{E1}$ is —OR$^{EE}$ (e.g., —OMe). In certain embodiments, at least one instance of R$^{E1}$ is —Si(R$^{EG}$)$_3$, wherein each instance of R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$).

In certain embodiments, at least one instance of R$^{E2}$ is H. In certain embodiments, at least one instance of R$^{E2}$ is halogen (e.g., F, Cl, Br, or I). In certain embodiments, at least one instance of R$^{E2}$ is optionally substituted alkyl (e.g., Me, or Et). In certain embodiments, at least one instance of $R^{E2}$ is optionally substituted alkenyl (e.g., optionally substituted vinyl). In certain embodiments, at least one instance of $R^{E2}$ is optionally substituted alkynyl. In certain embodiments, at least one instance of $R^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E2}$ is —CN. In certain embodiments, at least one instance of $R^{E2}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E2}$ is —CH$_2$N(R$^{EF}$)$_2$ or —N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E2}$ is —CH$_2$SR$^{EE}$ or —SR$^{EE}$ (e.g., CH$_2$SMe or —SMe). In certain embodiments, at least one instance of $R^{E2}$ is —OR$^{EE}$ (e.g., —OMe). In certain embodiments, at least one instance of $R^{E2}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, at least one instance of $R^{E3}$ is H. In certain embodiments, at least one instance of $R^{E3}$ is halogen (e.g., F, Cl, Br, or I). In certain embodiments, at least one instance of $R^{E3}$ is optionally substituted alkyl (e.g., Me, or Et). In certain embodiments, at least one instance of $R^{E3}$ is optionally substituted alkenyl (e.g., optionally substituted vinyl). In certain embodiments, at least one instance of $R^{E3}$ is optionally substituted alkynyl. In certain embodiments, at least one instance of $R^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E3}$ is —CN. In certain embodiments, at least one instance of $R^{E3}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E3}$ is —CH$_2$N(R$^{EF}$)$_2$ or —N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E3}$ is —CH$_2$SR$^{EE}$ or —SR$^{EE}$ (e.g., —CH$_2$SMe or —SMe). In certain embodiments, at least one instance of $R^{E3}$ is —OR$^{EE}$ (e.g., —OMe). In certain embodiments, at least one instance of $R^{E3}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, $R^{E1}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E2}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E2}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E1}$ and $R^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E4}$ is a leaving group (e.g., halogen, or a sulfonic acid ester, e.g., —O(tosylate) or —O(mesylate)). In certain embodiments, $R^{E5}$ is halogen (e.g., F, Cl, Br, or I). In certain embodiments, $R^{E6}$ is H. In certain embodiments, $R^{E6}$ is substituted or unsubstituted $C_{1-6}$ alkyl (e.g., Me, is —$CF_3$, Bn, Et, perfluoroethyl, Pr, perfluoropropyl, Bu, or perfluorobutyl). In certain embodiments, $R^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is $NR^{E7}$, wherein $R^{E7}$ is hydrogen, substituted or unsubstituted $C_{1-6}$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

Formulae (I') and (I) include zero or more instances of substituent $R^3$ on Ring C. In certain embodiments, n is 0. In certain embodiments, n is 1. In certain embodiments, n is 2. In certain embodiments, n is 3. In certain embodiments, at least one instance of $R^3$ is hydrogen. In certain embodiments, at least one instance of $R^3$ is substituted or unsubstituted acyl (e.g., —C(=O)Me). In certain embodiments, at least one instance of $R^3$ is halogen (e.g., F, Cl, Br, or I). In certain embodiments, at least one $R^3$ is substituted or unsubstituted alkyl (e.g., substituted or unsubstituted $C_{1-6}$ alkyl). In certain embodiments, at least one instance of $R^3$ is substituted or unsubstituted methyl. In certain embodiments, at least one instance of $R^3$ is substituted or unsubstituted ethyl. In certain embodiments, at least one instance of $R^3$ is substituted or unsubstituted propyl. In certain embodiments, at least one instance of $R^3$ is substituted or unsubstituted alkenyl (e.g., substituted or unsubstituted $C_{2-6}$ alkenyl). In certain embodiments, at least one instance of $R^3$ is substituted or unsubstituted alkynyl (e.g., substituted or unsubstituted $C_{2-6}$ alkynyl). In certain embodiments, at least one instance of $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^3$ is substituted or unsubstituted aryl (e.g., substituted or unsubstituted, 6- to 10-membered aryl). In certain embodiments, at least one instance of $R^3$ is benzyl. In certain embodiments, at least one instance of $R^3$ is substituted or unsubstituted phenyl. In certain embodiments, at least one instance of $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —$OR^{D1}$ (e.g., —OH or —OMe). In certain embodiments, at least one instance of $R^3$ is —$N(R^{D1a})_2$ (e.g., —$NMe_2$). In certain embodiments, at least one instance of $R^3$ is —$SR^{D1}$ (e.g., —SMe). In certain embodiments, two $R^3$ groups are joined to form an optionally substituted carbocyclyl (e.g., substituted or unsubstituted, 3- to 7-membered, monocyclic carbocyclyl comprising zero, one, or two double bonds in the carbocyclic ring system), optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur), optionally substituted aryl (e.g., substituted or unsubstituted, 6- to 10-membered aryl), or optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, $R^{D1}$ is hydrogen. In certain embodiments, $R^{D1}$ is substituted or unsubstituted acyl (e.g., —C(=O)Me). In certain embodiments, $R^{D1}$ is substituted or unsubstituted alkyl (e.g., substituted or unsubstituted $C_{1-6}$ alkyl). In certain embodiments, $R^{D1}$ is substituted or unsubstituted methyl. In certain embodiments, $R^{D1}$ is substituted or unsubstituted ethyl. In certain embodiments, $R^{D1}$ is substituted or unsubstituted propyl. In certain embodiments, $R^{D1}$ is substituted or unsubstituted alkenyl (e.g., substituted or unsubstituted $C_{2-6}$ alkenyl). In certain embodiments, $R^{D1}$ is substituted or unsubstituted alkynyl (e.g., substituted or unsubstituted $C_{2-6}$ alkynyl). In certain embodiments, $R^{D1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{D1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is substituted or unsubstituted aryl (e.g., substituted or unsubstituted, 6- to 10-membered aryl). In certain embodiments, $R^{D1}$ is benzyl. In certain embodiments, $R^{D1}$ is substituted or unsubstituted phenyl. In certain embodiments, $R^{D1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is an oxygen protecting group when attached to an oxygen atom. In certain embodiments, $R^{D1}$ is a sulfur protecting group when attached to a sulfur atom.

In certain embodiments, at least one instance of $R^{D1a}$ is hydrogen. In certain embodiments, at least one instance of $R^{D1}$ is substituted or unsubstituted acyl (e.g., —C(=O)Me). In certain embodiments, at least one $R^{D1a}$ is substituted or unsubstituted alkyl (e.g., substituted or unsubstituted $C_{1-6}$ alkyl). In certain embodiments, at least one instance of $R^{D1a}$ is substituted or unsubstituted methyl. In certain embodiments, at least one instance of $R^{D1a}$ is substituted or unsubstituted ethyl. In certain embodiments, at least one instance of $R^{D1a}$ is substituted or unsubstituted propyl. In certain embodiments, at least one instance of $R^{D1a}$ is substituted or unsubstituted alkenyl (e.g., substituted or unsubstituted $C_{2-6}$ alkenyl). In certain embodiments, at least one instance of $R^{D1a}$ is substituted or unsubstituted alkynyl (e.g., substituted or unsubstituted $C_{2-6}$ alkynyl). In certain embodiments, at least one instance of $R^{D1a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D1a}$ is substituted or unsubstituted aryl (e.g., substituted or unsubstituted, 6- to 10-membered aryl). In certain embodiments, at least one instance of $R^{D1a}$ is benzyl. In certain embodiments, at least one instance of $R^{D1a}$ is substituted or unsubstituted phenyl. In certain embodiments, at least one instance of $R^{D1a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I') includes linker $L^{1A}$ which is attached to Ring A1 at one end of $L^{1A}$ and attached to Ring B at the other end of $L^{1A}$. In certain embodiments, $L^{1A}$ is $L^1$. In certain embodiments, $L^{1A}$ is of formula $^{1a}$—$NR^{L1}C(=O)$—$^{1b}$, $^{1a}$—$NR^{L1}C(=O)$—$^{1b}$, or a 5-membered heteroaryl ring; wherein $^{1a}$ indicates the point of attachment to Ring A; $^{1b}$ indicates the point of attachment to Ring B; and $R^{L1}$ is independently hydrogen, optionally substituted $C_{1-6}$ alkyl, or a nitrogen protecting group. In certain embodiments, $L^{1A}$ is of formula $^{1a}$—$NHC(=O)$—$^{1b}$. In certain embodiments, $L^{1A}$ is of formula $^{1a}$—$C(=O)NH$—$^{1b}$. In certain embodiments, $L^{1A}$ is an optionally substituted heteroarylene (e.g., substituted or unsubstituted, 5- to 6-membered, monocyclic heteroarylene, wherein one, two, three, or four atoms in the heteroarylene are independently nitrogen, oxygen, or sulfur; or substituted or unsubstituted, 9- to 10-membered, bicyclic heteroaryl, wherein one, two, three, or four atoms in the heteroarylene are independently nitrogen, oxygen, or sulfur). In certain embodiments, $L^{1A}$ is an optionally substituted 5-membered heteroarylene (e.g., pyrrolylene, furanylene, thiophenylene, imidazolylene, pyrazolylene, oxazolylene, isoxazolylene, thiazolylene, isothiazolylene, dimethyloxazolylene, triazolylene, oxadiazolylene, or thiadiazolylene, all of which are optionally substituted). In certain embodiments, $L^{1A}$ is of formula

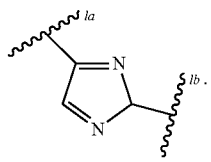

In certain embodiments, $L^{1A}$ is of formula

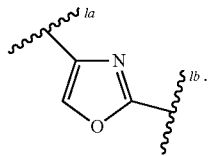

In certain embodiments, $L^{1A}$ is of formula

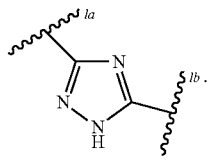

In certain embodiments, $L^{1A}$ is of formula

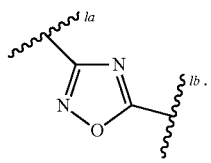

In certain embodiments, $L^{1A}$ is of formula

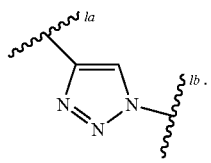 [SMILES: *c1cn(*)nn1]

As generally defined herein, Formula (I) includes linker $L^1$ which is attached to Ring A at one end of $L^1$ and attached to Ring B at the other end of $L^1$. In certain embodiments, $L^1$ is $^{1a}$—$NR^{L1}C(=O)$—$^{1b}$ or a 5-membered heteroaryl ring; wherein $^{1a}$ indicates the point of attachment to Ring A; $^{1b}$ indicates the point of attachment to Ring B; and $R^{L1}$ is independently hydrogen, optionally substituted $C_{1-6}$ alkyl, or a nitrogen protecting group. In certain embodiments, $R^{L1}$ is hydrogen. In certain embodiments, $R^{L1}$ is optionally substituted $C_{1-6}$ alkyl (e.g. optionally substituted methyl or optionally substituted ethyl). In certain embodiments, $R^{L1}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $L^1$ is $^{1a}$—$NHC(=O)$—$^{1b}$. In certain embodiments, $L^1$ is an unsubstituted 5-membered heteroaryl ring. In certain embodiments, $L^1$ is an unsubstituted 5-membered heteroarylene. In certain embodiments, $L^1$ is of formula:

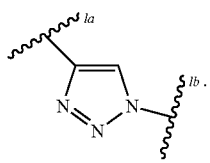 [SMILES: *c1cn(*)nn1]

Formula (I') includes zero or more instances of substituent $R^4$ on Ring A1. Formula (I) includes zero or more instances of substituent $R^4$ on Ring A. In certain embodiments, p is 0. In certain embodiments, p is 1. In certain embodiments, p is 2. In certain embodiments, p is 3. In certain embodiments, p is 4. In certain embodiments, at least one instance of $R^4$ is hydrogen. In certain embodiments, at least one instance of $R^4$ is substituted or unsubstituted acyl (e.g., —C(=O)Me). In certain embodiments, at least one instance of $R^4$ is halogen (e.g., F, Cl, Br, or I). In certain embodiments, at least one $R^4$ is substituted or unsubstituted alkyl (e.g., substituted or unsubstituted $C_{1-6}$ alkyl). In certain embodiments, at least one instance of $R^4$ is substituted or unsubstituted methyl. In certain embodiments, at least one instance of $R^4$ is substituted or unsubstituted ethyl. In certain embodiments, at least one instance of $R^4$ is substituted or unsubstituted propyl. In certain embodiments, at least one instance of $R^4$ is substituted or unsubstituted alkenyl (e.g., substituted or unsubstituted $C_{2-6}$ alkenyl). In certain embodiments, at least one instance of $R^4$ is substituted or unsubstituted alkynyl (e.g., substituted or unsubstituted $C_{2-6}$ alkynyl). In certain embodiments, at least one instance of $R^4$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^4$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^4$ is substituted or unsubstituted aryl (e.g., substituted or unsubstituted, 6- to 10-membered aryl). In certain embodiments, at least one instance of $R^4$ is benzyl. In certain embodiments, at least one instance of $R^4$ is substituted or unsubstituted phenyl. In certain embodiments, at least one instance of $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^4$ is —$OR^{D1}$ (e.g., —OH or —OMe). In certain embodiments, at least one instance of $R^4$ is —$N(R^{D1a})_2$ (e.g., —NMe$_2$). In certain embodiments, at least one instance of $R^4$ is —$SR^{D1}$ (e.g., —SMe).

Formula (I') includes Ring A1. In certain embodiments, Ring A1 is Ring A. In certain embodiments, Ring A1 is optionally substituted carbocyclyl (e.g., substituted or unsubstituted, 3- to 10-membered, monocyclic or bicyclic carbocyclyl comprising zero, one, or two double bonds in the carbocyclic ring system). In certain embodiments, Ring A1 is optionally substituted cyclohexyl. In certain embodiments, Ring A1 is optionally substituted cyclopentyl. In certain embodiments, Ring A1 is optionally substituted cyclohexyl. In certain embodiments, Ring A1 is unsubstituted cyclohexyl.

In certain embodiments, Ring A1 is

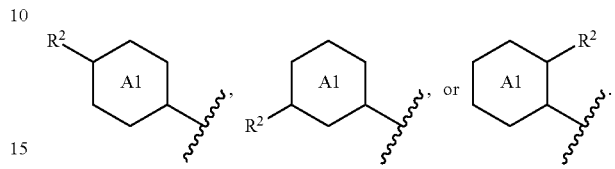

In certain embodiments, Ring A1 is

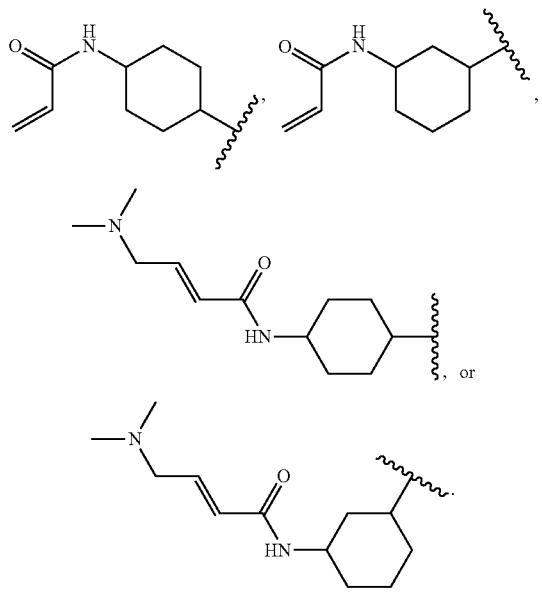

In certain embodiments, Ring A1 is optionally substituted cyclopropyl, optionally substituted cycloheptyl, or optionally substituted cyclooctyl. In certain embodiments, Ring A1 is optionally substituted bicyclic carbocyclyl. In certain embodiments, Ring A1 is optionally substituted bicyclo[1.1.1]pentane. In certain embodiments, Ring A1 is unsubstituted bicyclo[1.1.1]pentane. In certain embodiments, Ring A1 is optionally substituted bicyclo[2.2.1]heptanyl, or optionally substituted bicyclo[2.2.2]octanyl.

In certain embodiments, Ring A1 is

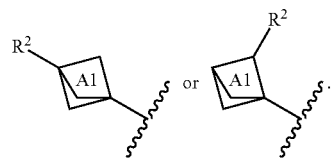

In certain embodiments, Ring A1 is

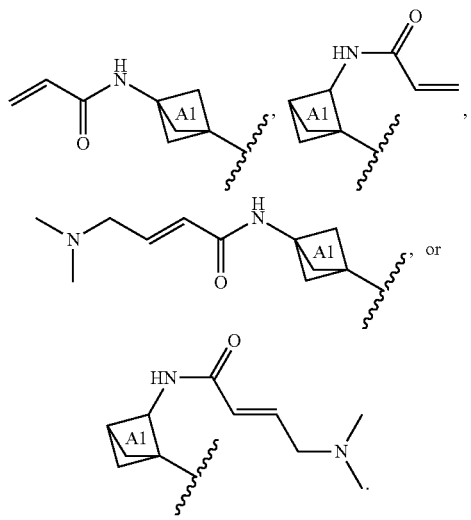

In certain embodiments, Ring A1 is optionally substituted aryl (e.g., substituted or unsubstituted, 6- to 10-membered aryl). In certain embodiments, Ring A1 is optionally substituted phenyl. In certain embodiments, Ring A1 is unsubstituted phenyl. In certain embodiments, Ring A1 is optionally substituted benzyl.

In certain embodiments, Ring A1 is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Ring A1 is optionally substituted heterocyclyl, wherein one or two atoms in the heterocyclic ring are independently nitrogen, oxygen, or sulfur. In certain embodiments, Ring A1 is optionally substituted 5-membered heterocyclyl. In certain embodiments, Ring A1 is optionally substituted 6-membered heterocyclyl. In certain embodiments, Ring A1 is optionally substituted 5-6 membered heterocyclyl, wherein one or two atoms in the heterocyclic ring are independently nitrogen, oxygen, or sulfur. In certain embodiments, Ring A1 is optionally substituted tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxasulfuranyl, disulfuranyl, triazolinyl, oxadiazolinyl, thiadiazolinyl, tetrahydropyranyl, dihydropyridinyl, piperazinyl, morpholinyl, dioxanyl, or thianyl. In certain embodiments, Ring A1 is optionally substituted piperidine. In certain embodiments, Ring A1 is unsubstituted piperidine. In certain embodiments, Ring A1 is unsubstituted cyclohexyl, unsubstituted bicyclo[1.1.1]pentane, unsubstituted phenyl, or unsubstituted piperidine.

In certain embodiments, Ring A1 is

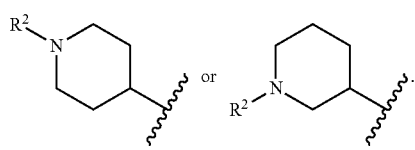

In certain embodiments, Ring A1 is

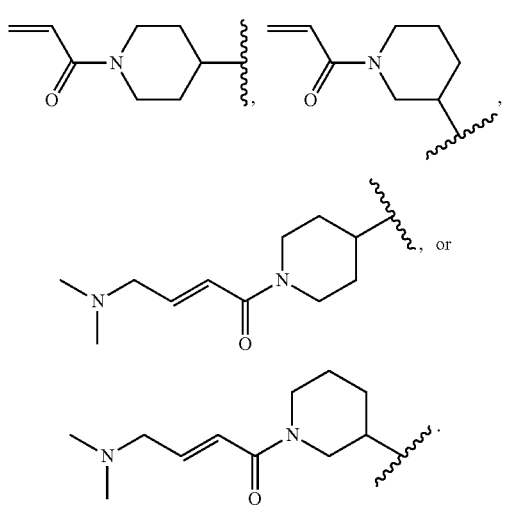

In certain embodiments, Ring A is:

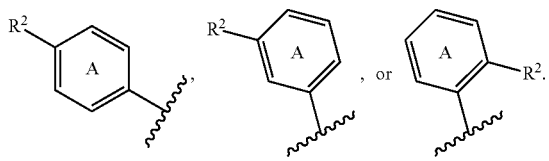

In certain embodiments, Ring A is:

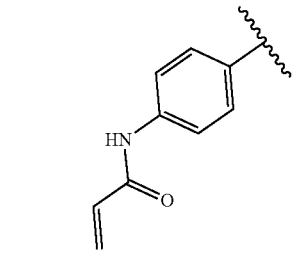

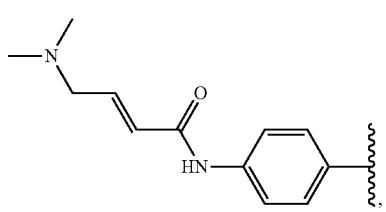

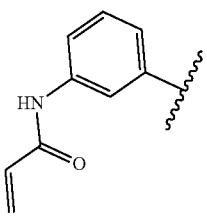

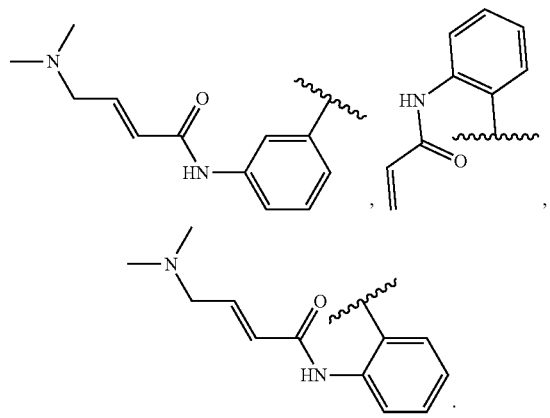
, or
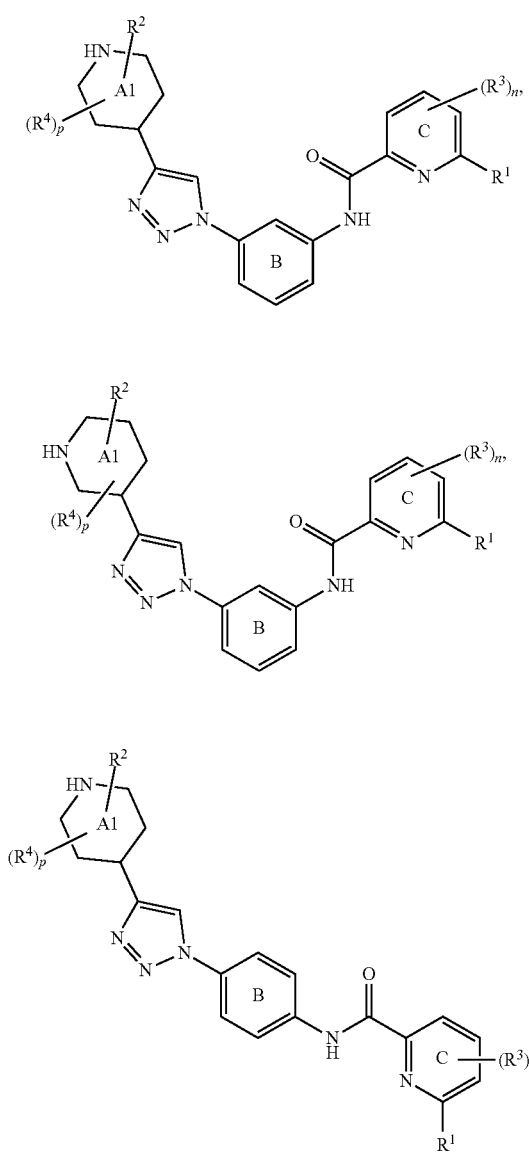
In certain embodiments, the compound of Formula (I') is of the formula:
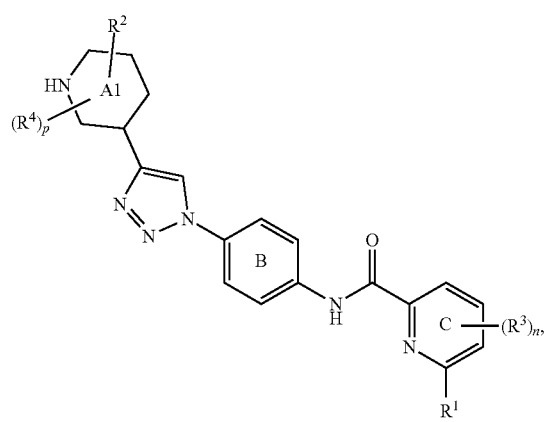
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
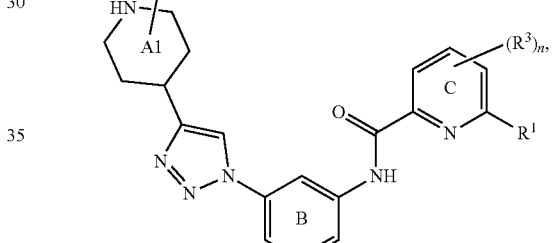
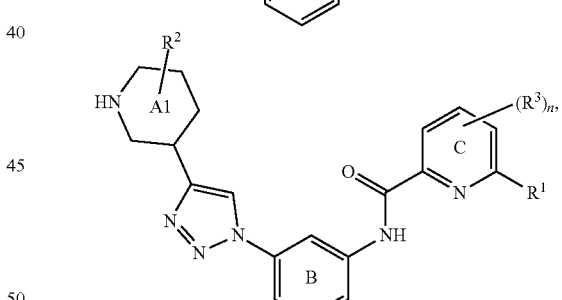
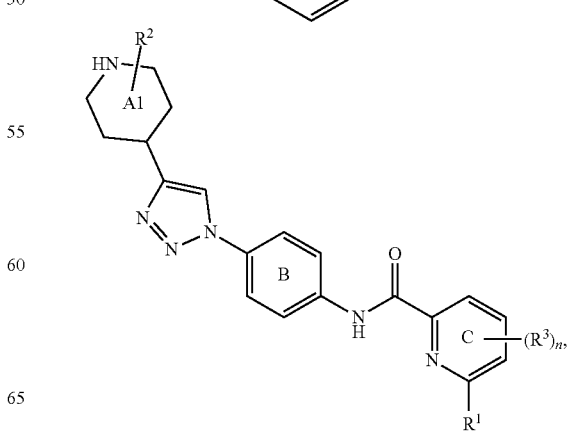

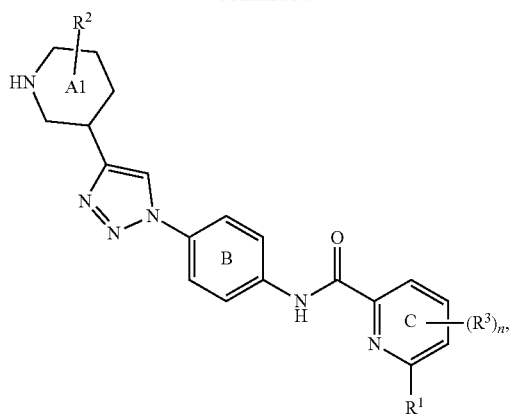

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

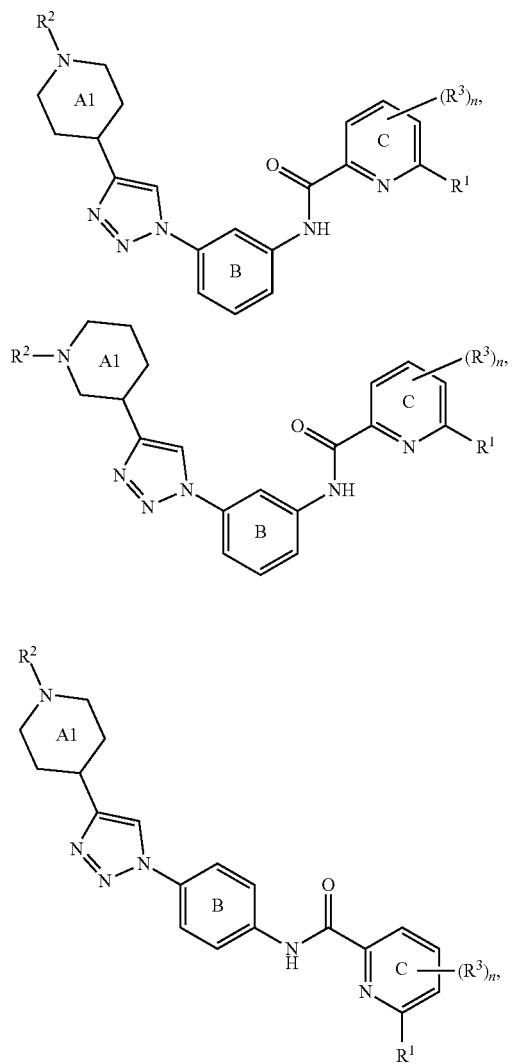

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

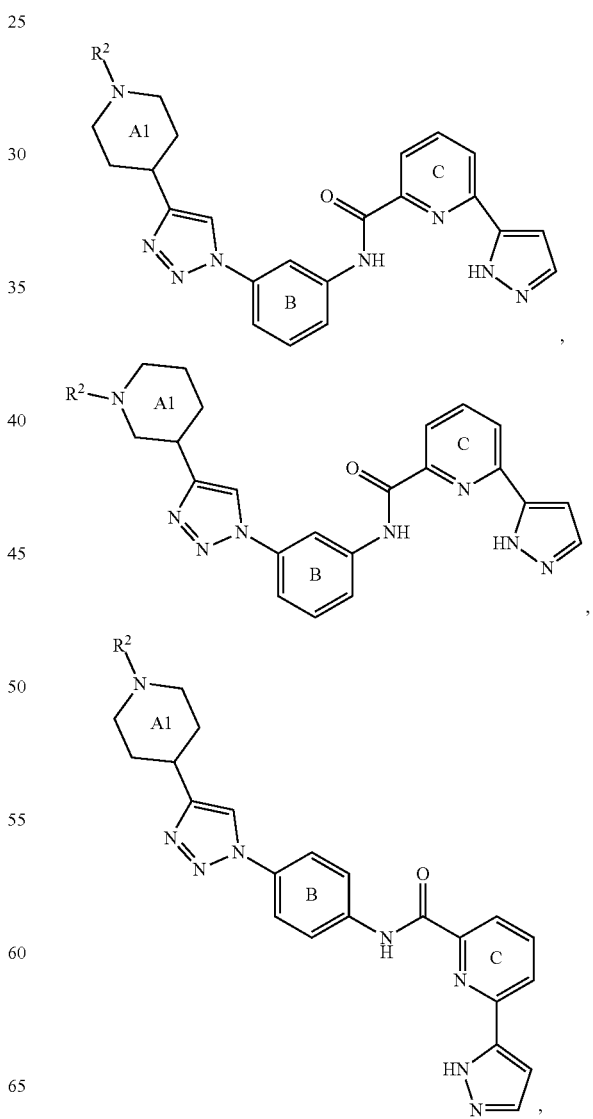

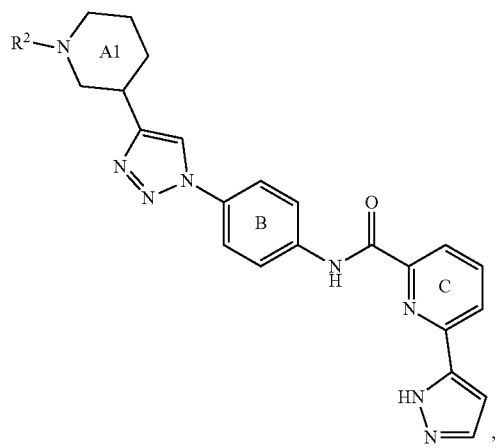

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

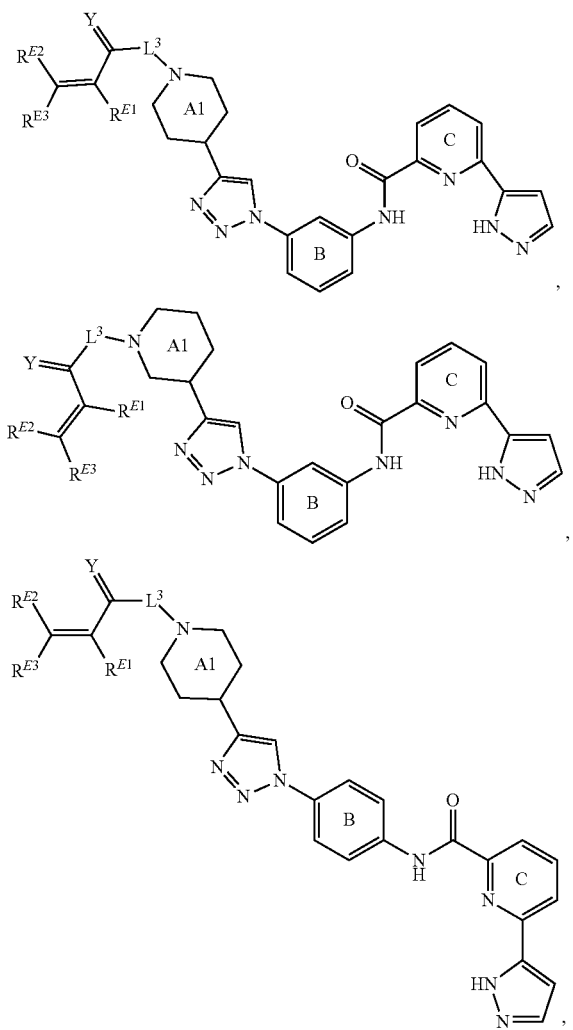

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

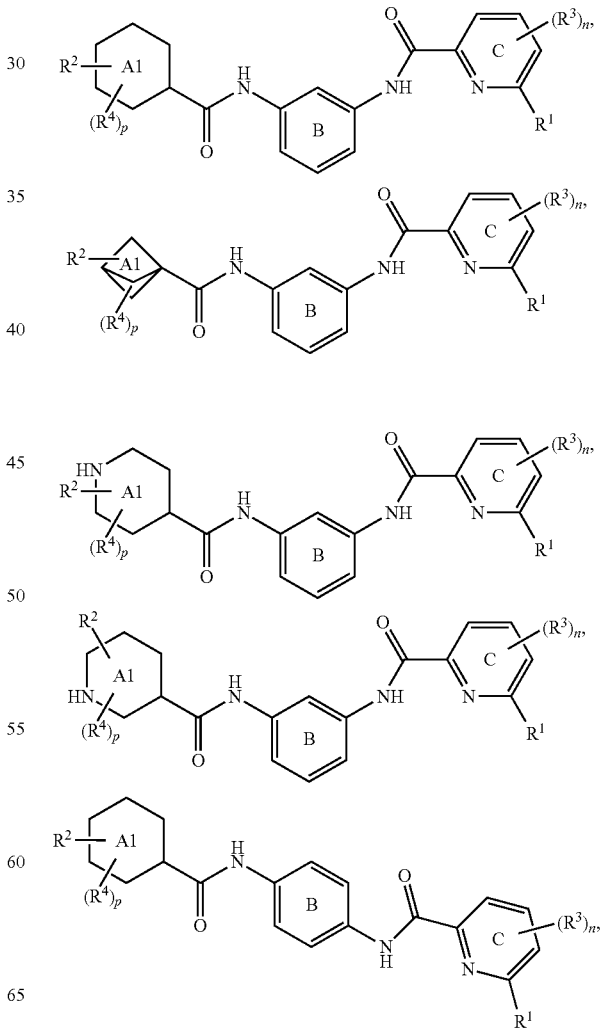

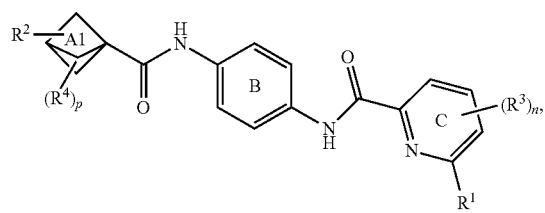

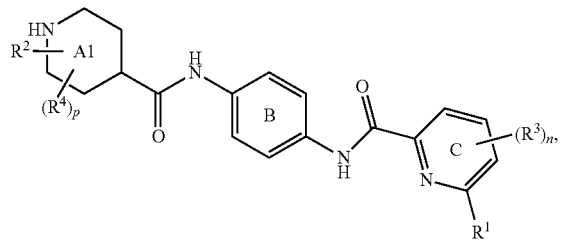

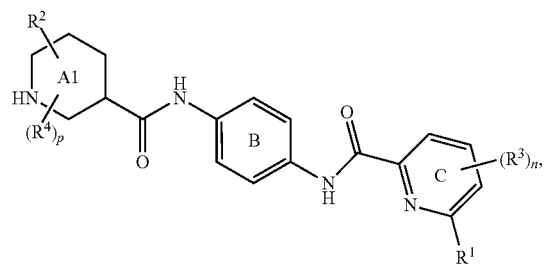

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

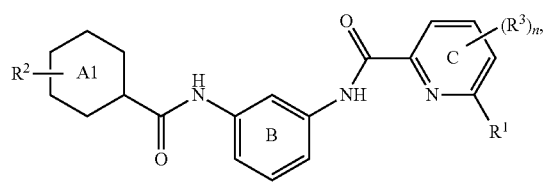

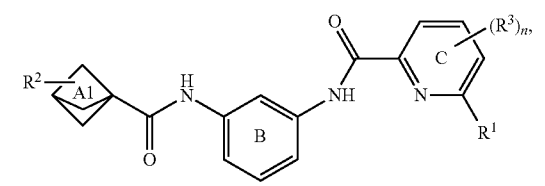

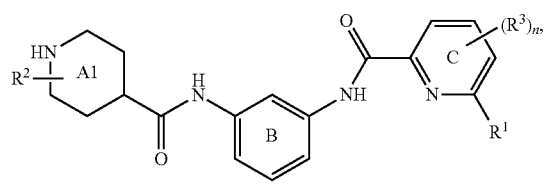

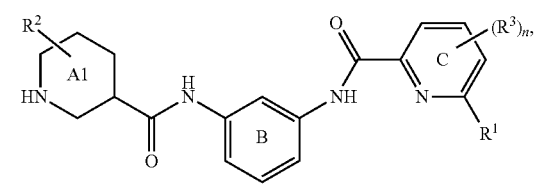

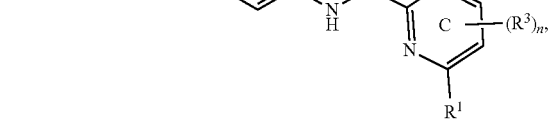

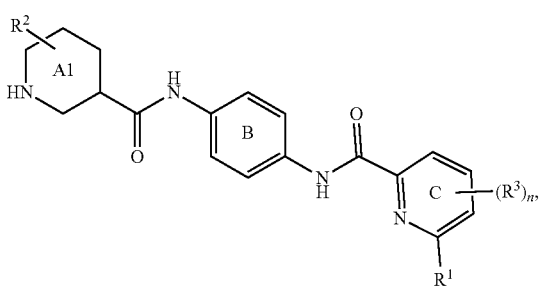

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

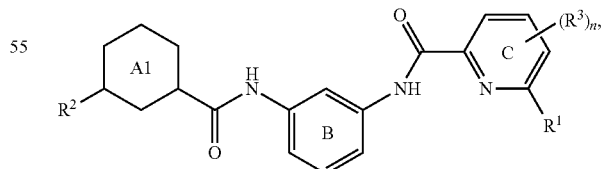

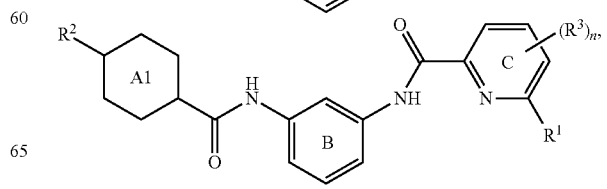

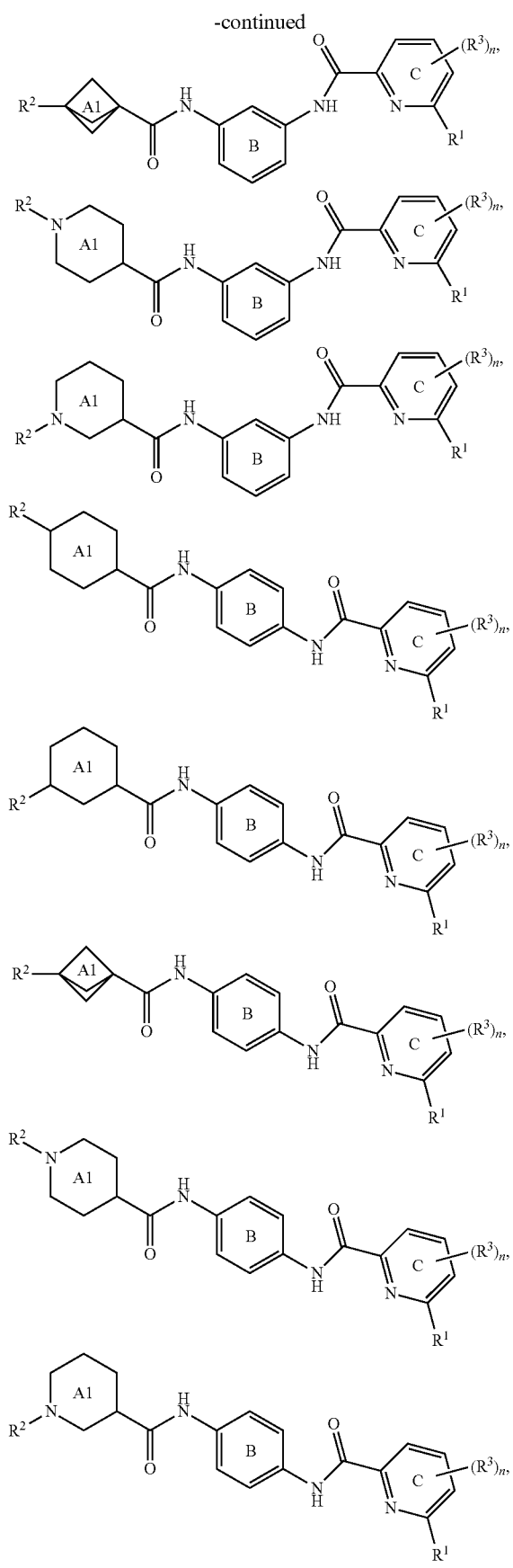
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:

-continued
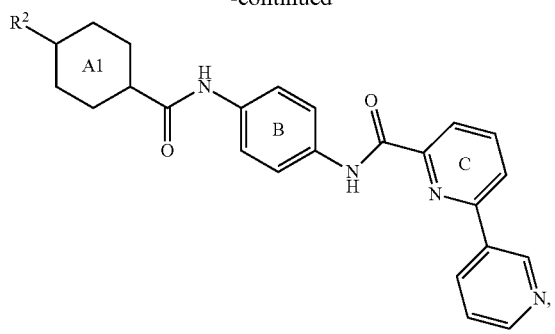
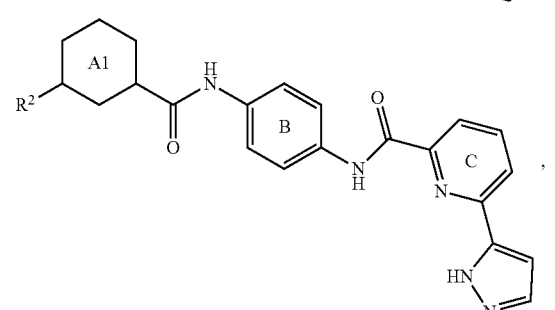
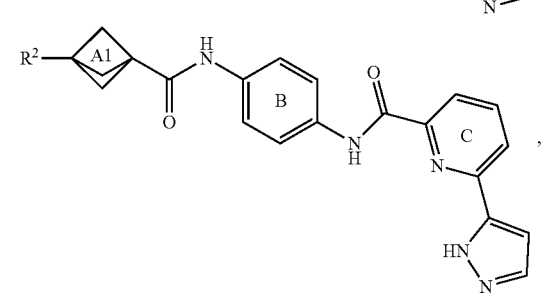
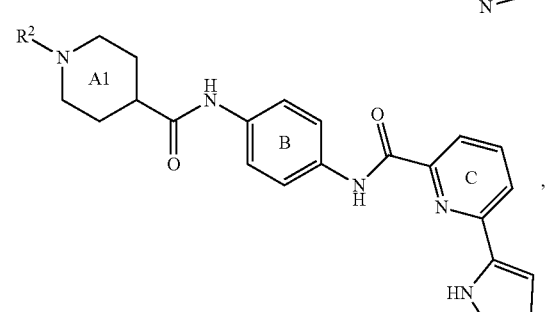
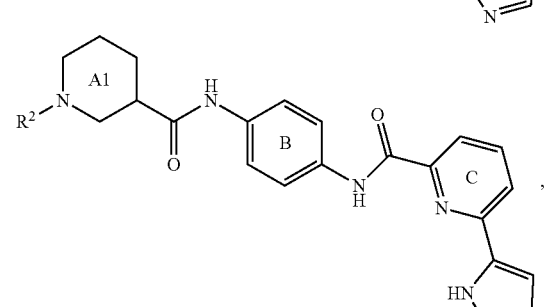
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
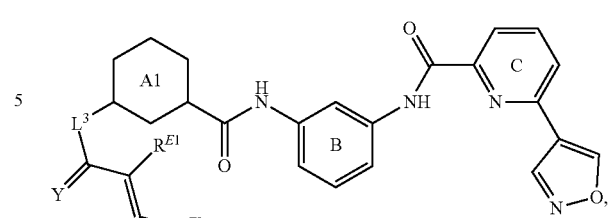
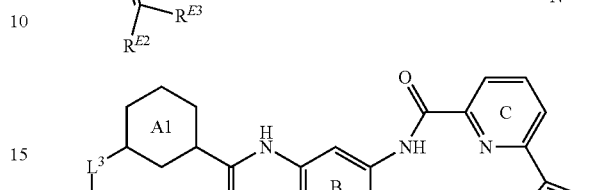
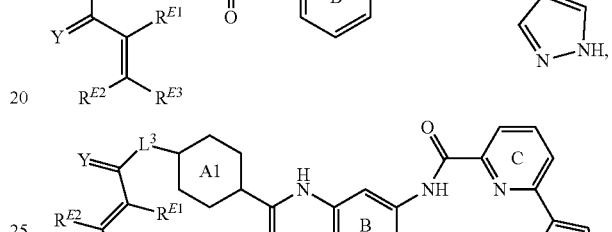
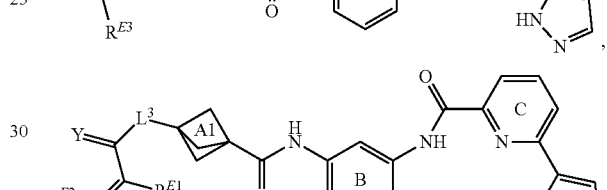
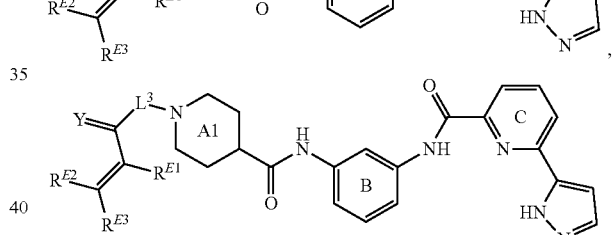
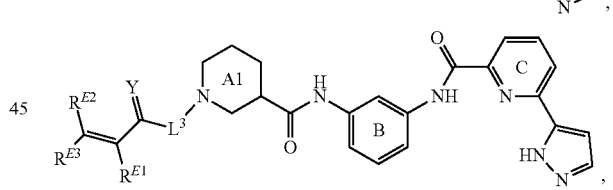
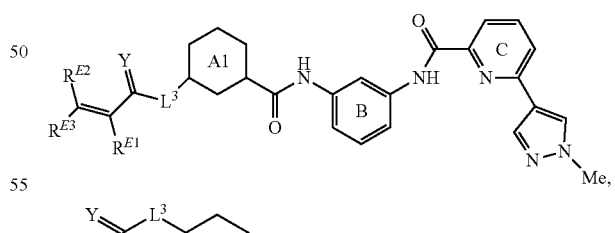
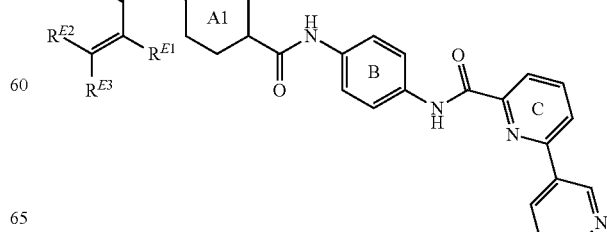

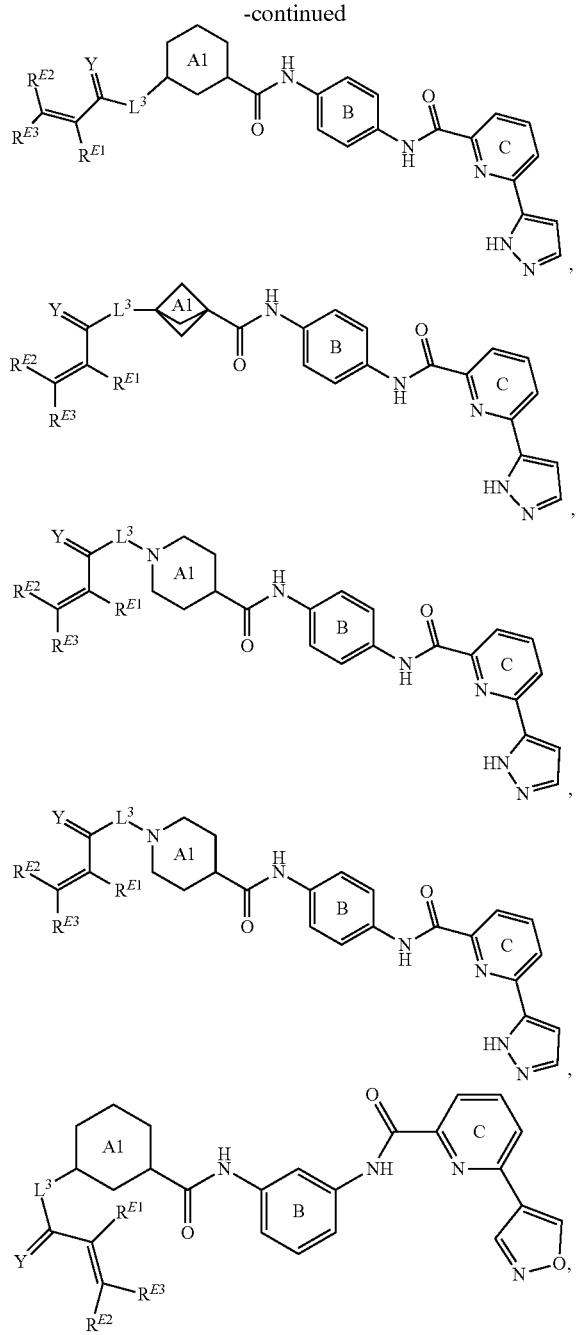

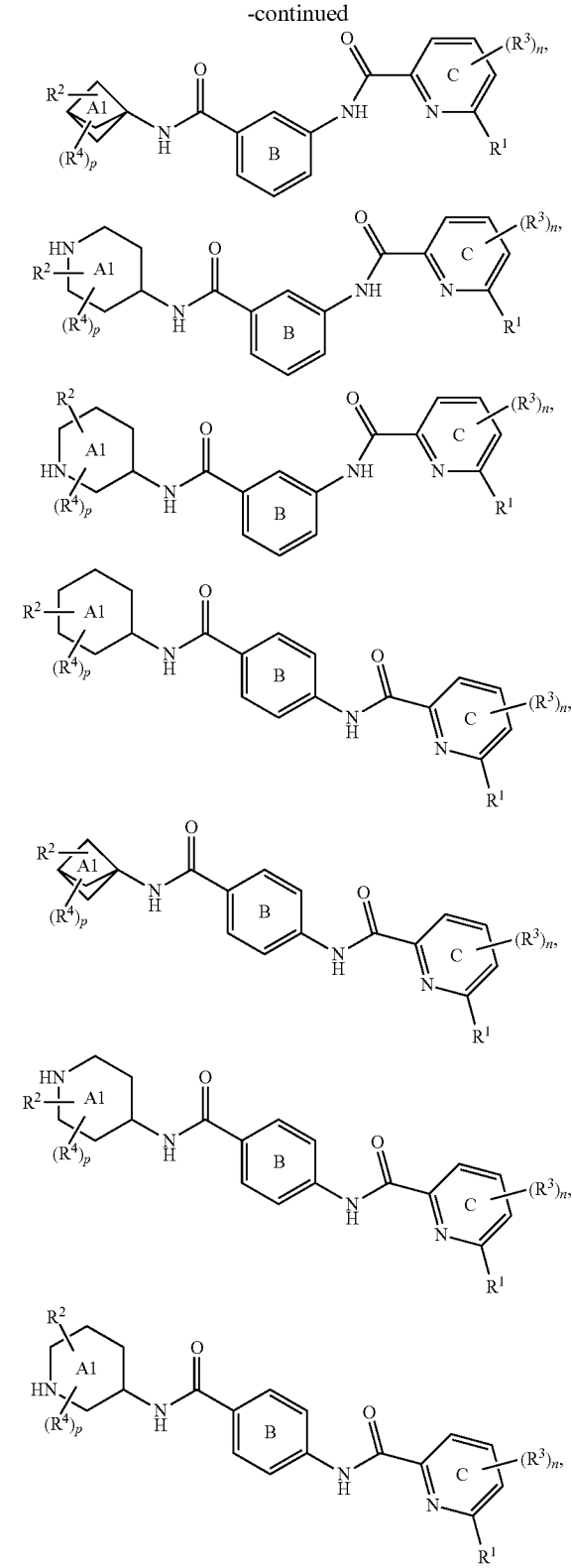

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

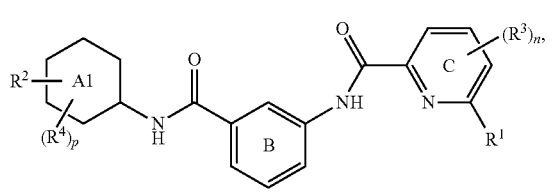

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

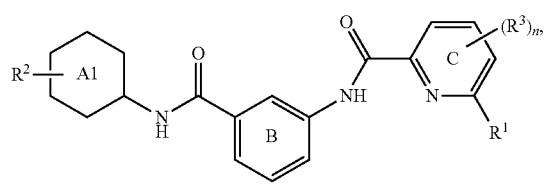
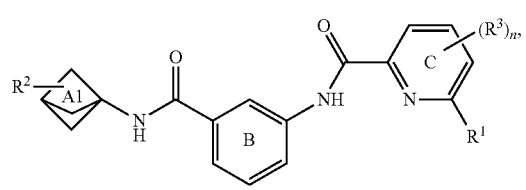
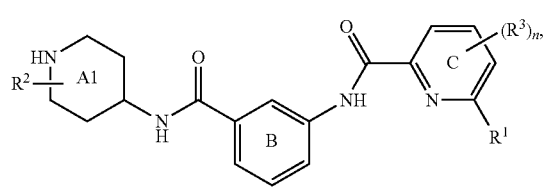
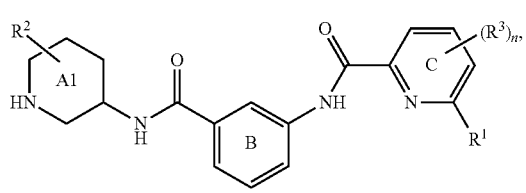
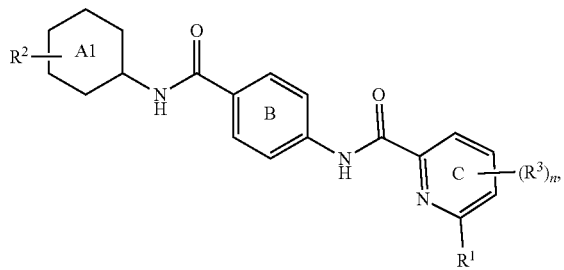
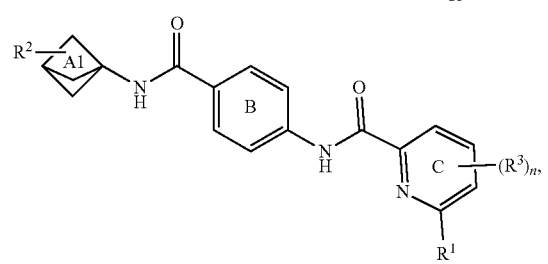
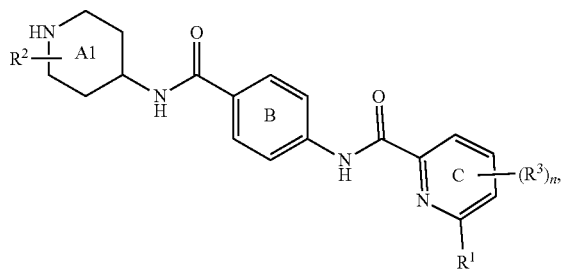
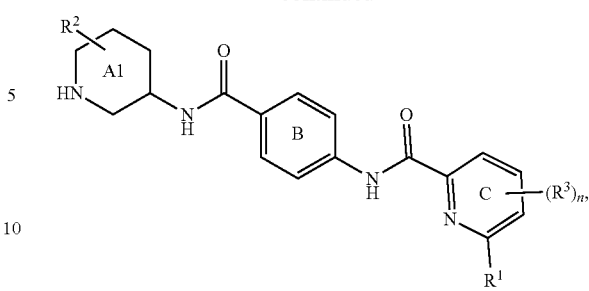
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
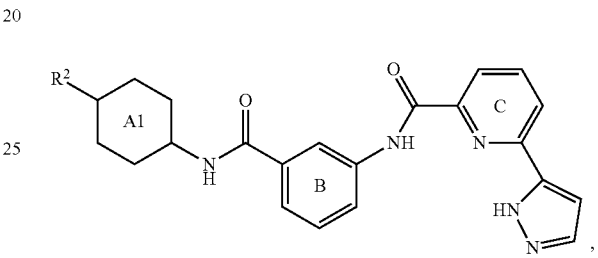
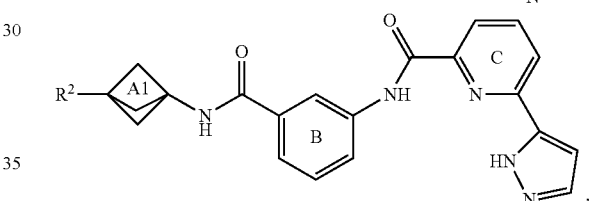
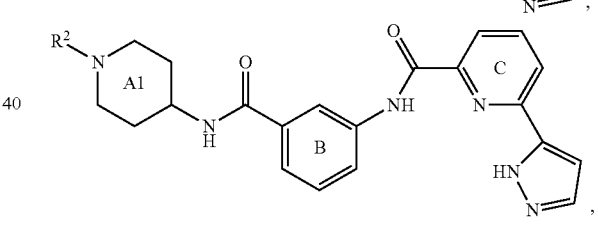
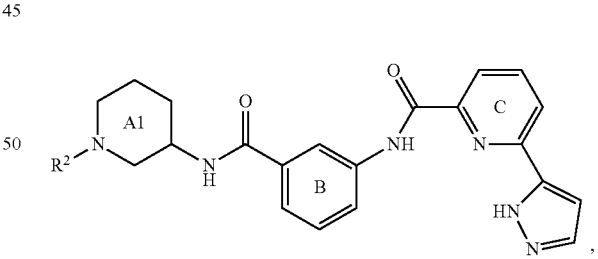
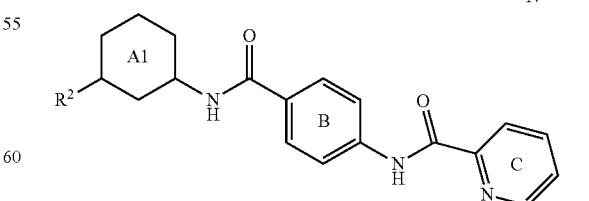

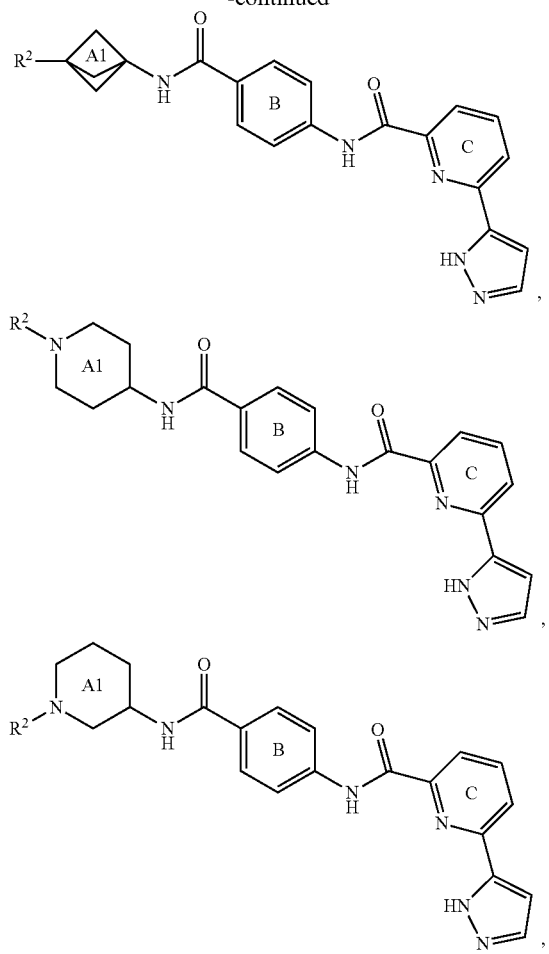

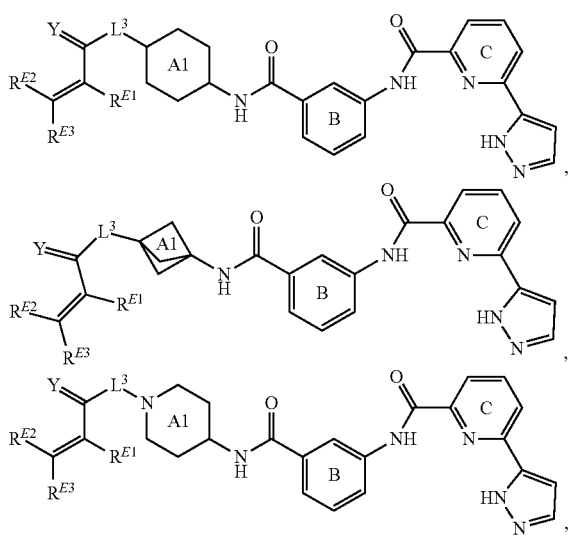

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

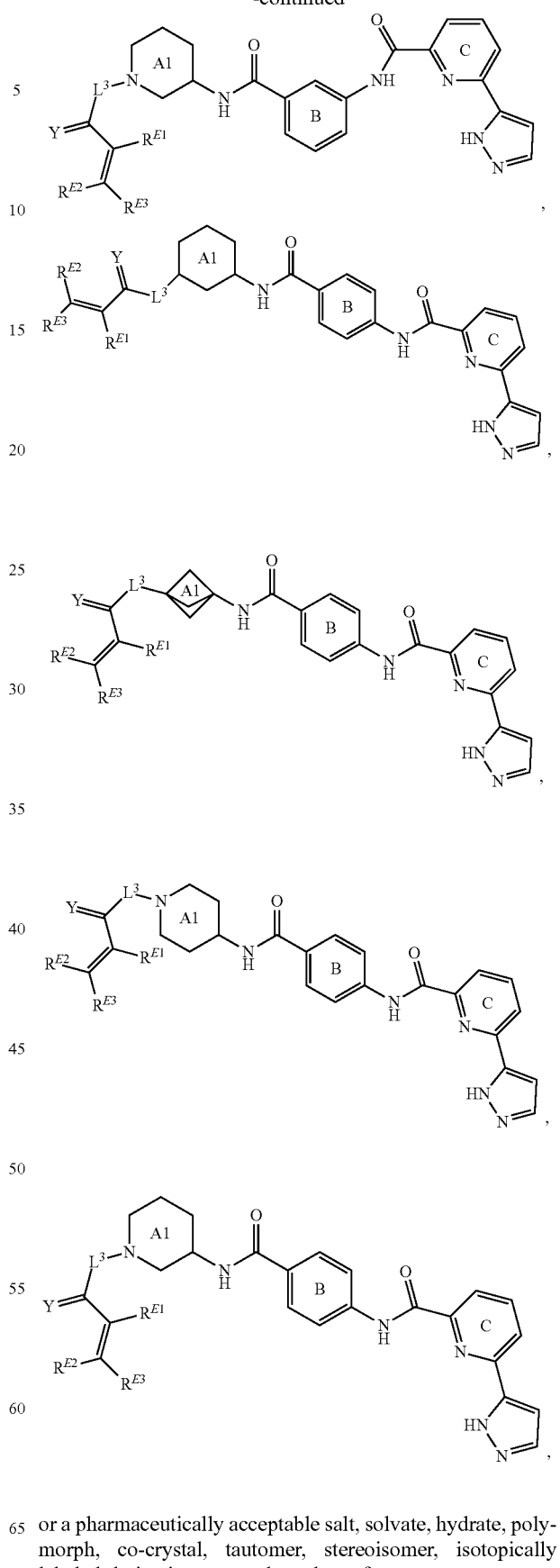

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

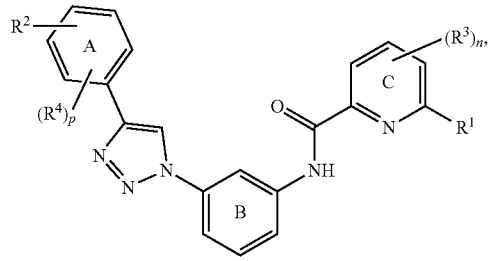

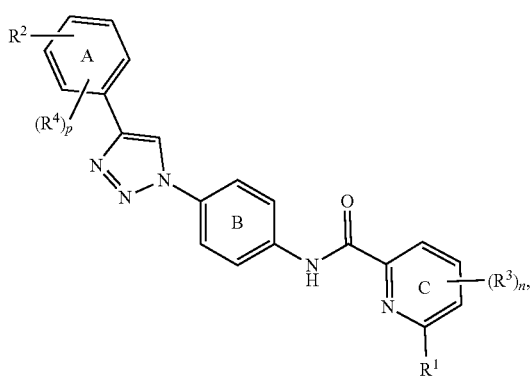

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

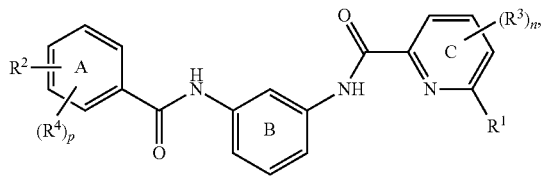

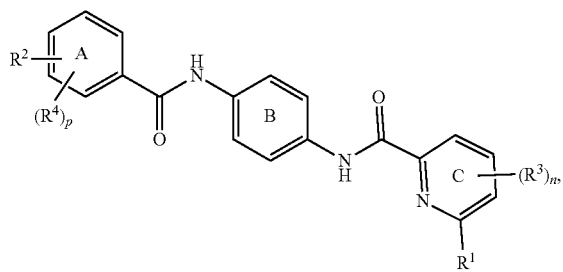

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

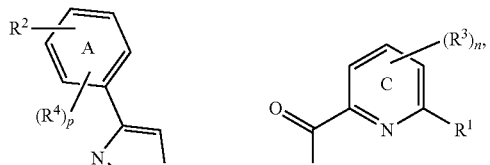

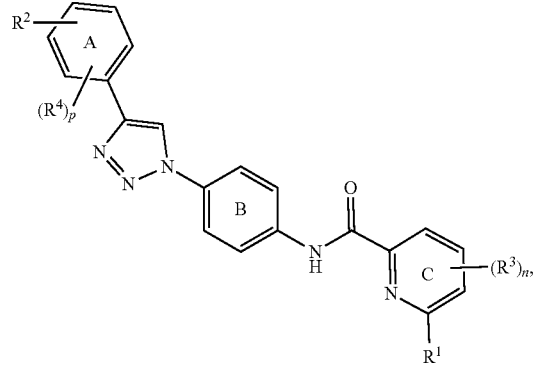

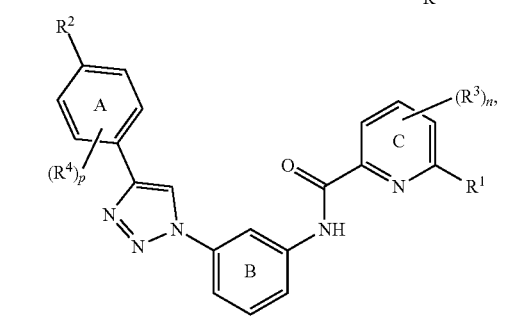

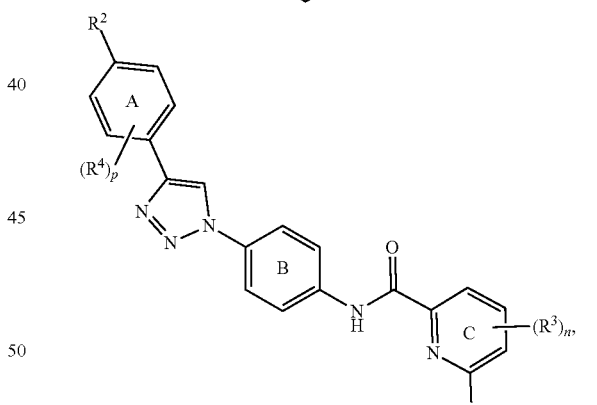

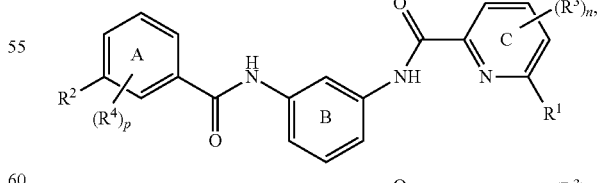

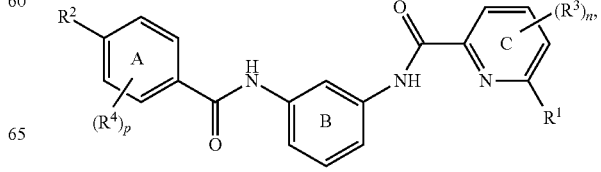

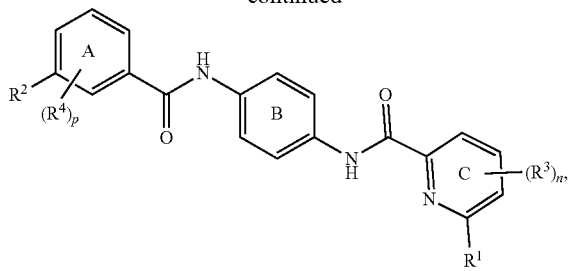

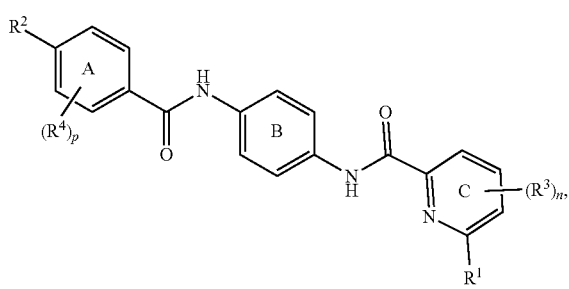

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

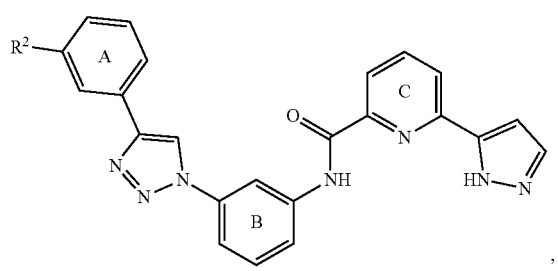

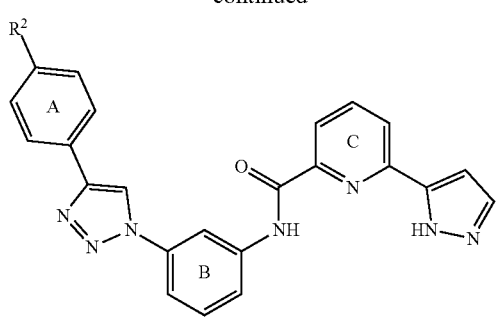

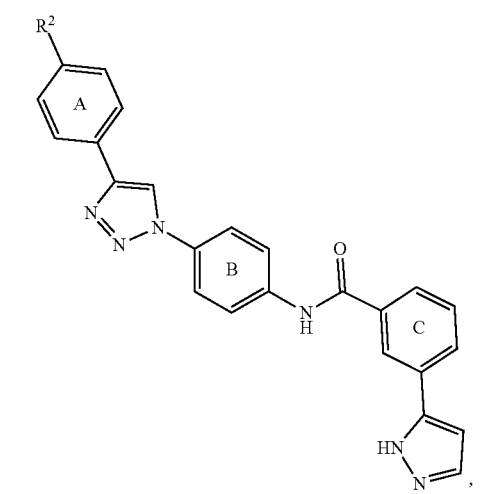

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

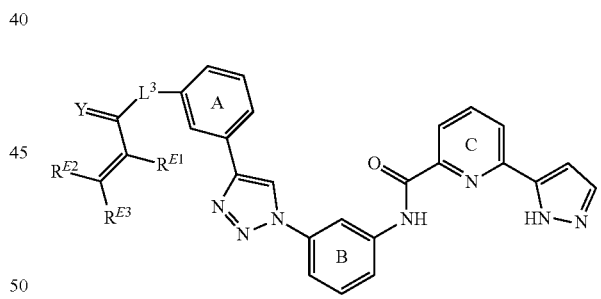

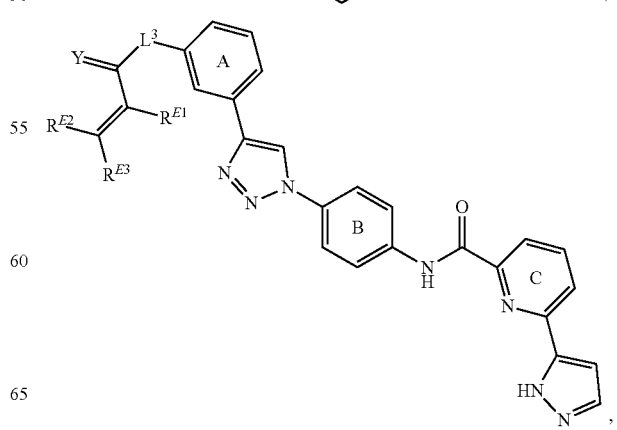

103
-continued
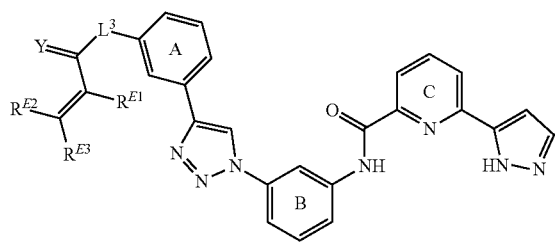
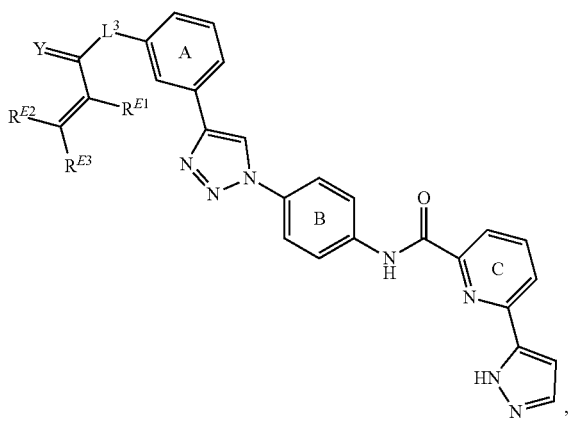
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
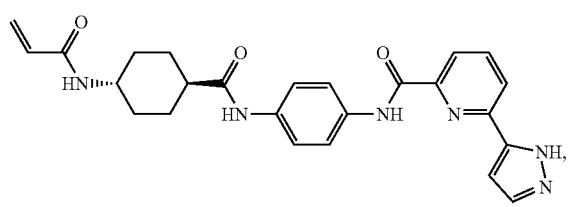
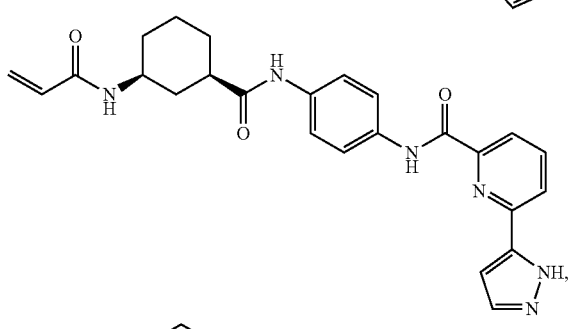
104
-continued
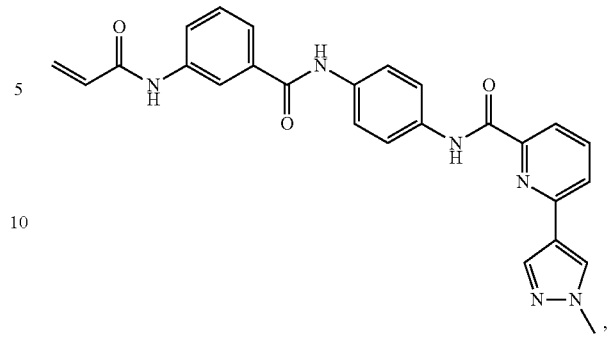
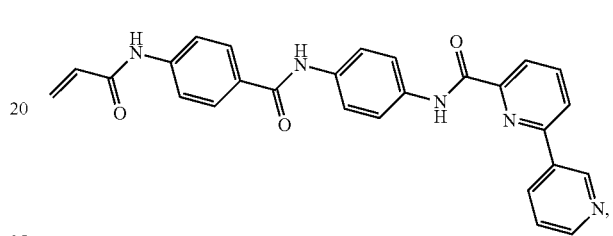
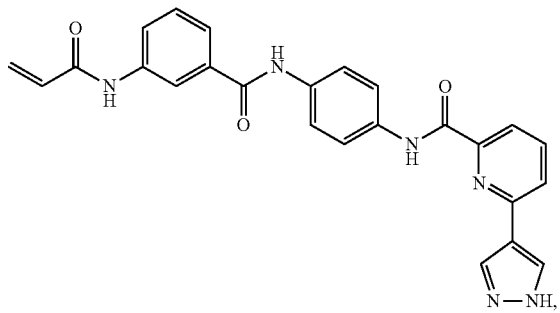
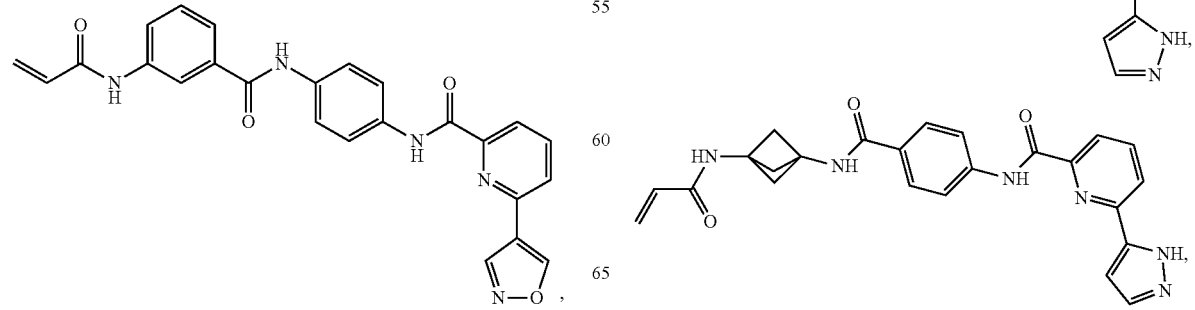

105
-continued
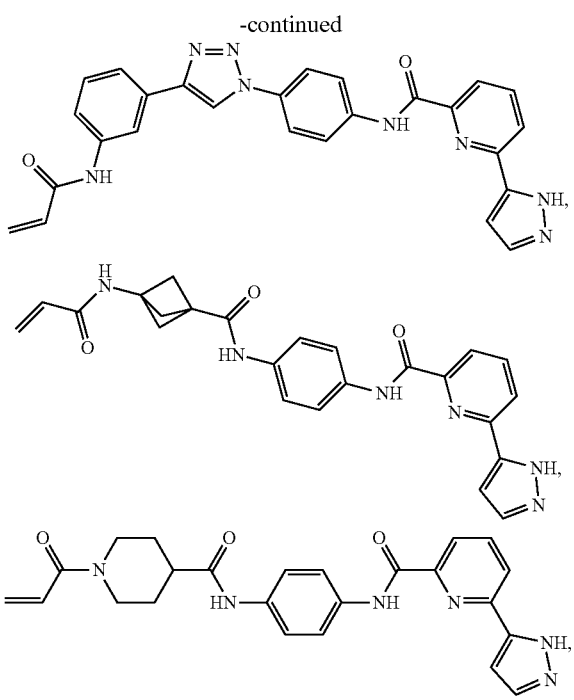
106
-continued
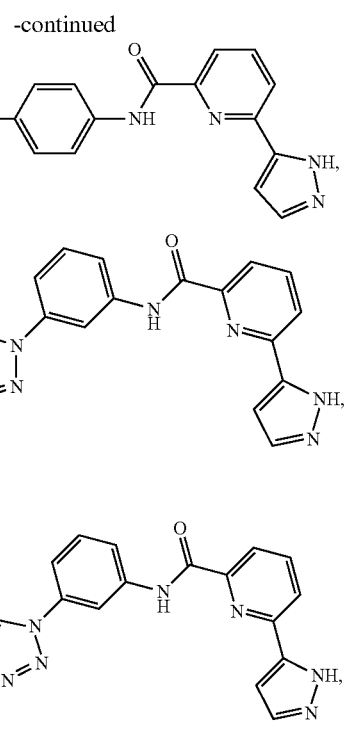
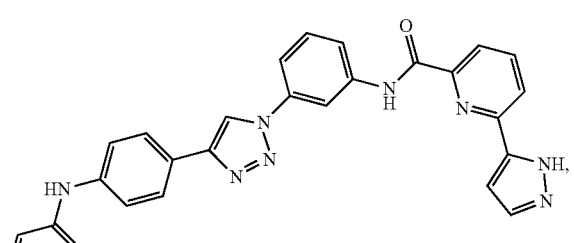
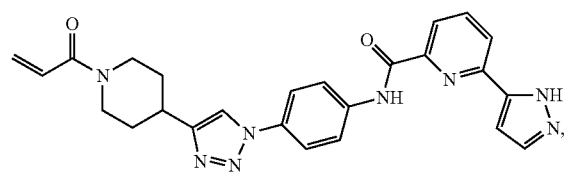
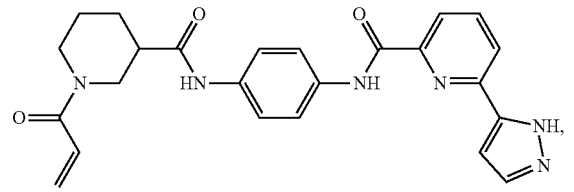
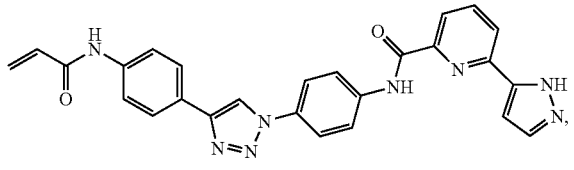
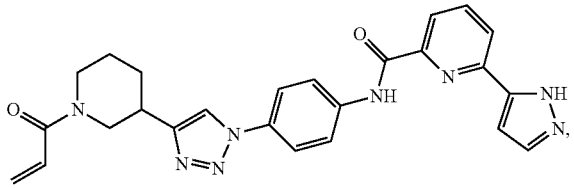
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
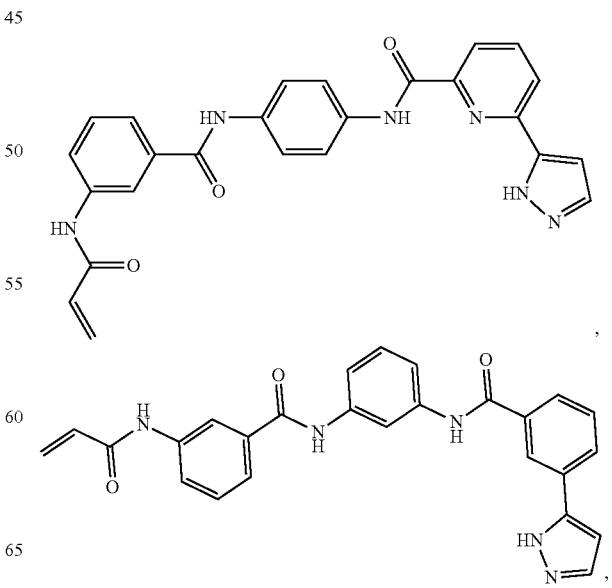

-continued

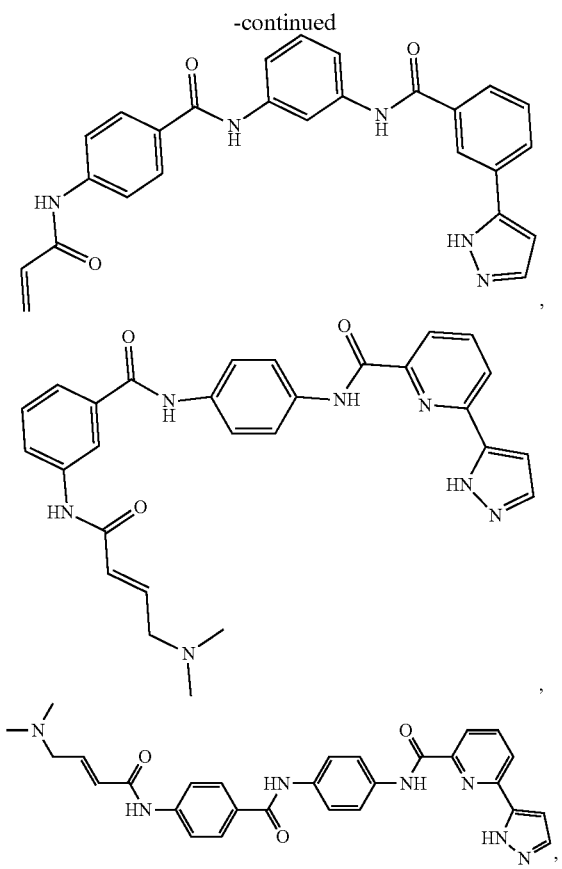

or a pharmaceutically acceptable salt, solvate, hydrate, polymorph, co-crystal, tautomer, stereoisomer, isotopically labeled derivative, or prodrug thereof.

In certain embodiments, the compound of Formulae (I') or (I) is a compound provided in any one of Tables 1-4 below.

In certain embodiments, a compound described herein is a compound of Formula (I'), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I'), or a pharmaceutically acceptable salt thereof.

Certain compounds described herein bind, covalently modify, and/or inhibit a protein kinase. In certain embodiments, the protein kinase is an IRAK. In certain embodiments, the protein kinase is IRAK1. In certain embodiments, the protein kinase is IRAK4. In certain embodiments, the compounds described herein covalently bind to the protein kinase (e.g., IRAK (e.g., IRAK1 or IRAK4)). In certain embodiments, the compounds described herein reversibly bind to the protein kinase (e.g., IRAK (e.g., IRAK1 or IRAK4)). In certain embodiments, the compounds described herein non-reversibly bind to the protein kinase (e.g., IRAK (e.g., IRAK1 or IRAK4). In certain embodiments, the compounds described herein modulate the activity of the protein kinase (e.g., IRAK (e.g., IRAK1 or IRAK4)). In certain embodiments, the compounds described herein inhibit the activity of the protein kinase (e.g., IRAK (e.g., IRAK1 or IRAK4)).

The binding affinity of a compound described herein to a protein kinase (e.g., IRAK, (e.g., IRAK1 or IRAK4)) may be measured by the dissociation constant ($K_d$) value of an adduct of the compound and the protein kinase (e.g., IRAK, (e.g., IRAK1 or IRAK4)) using methods known in the art (e.g., isothermal titration calorimetry (ITC)). In certain embodiments, the $K_d$ value of the adduct is not more than about 100 μM, not more than about 10 μM, not more than about 1 μM, not more than about 100 nM, not more than about 10 nM, or not more than about 1 nM.

In certain embodiments, the activity of a protein kinase (e.g., IRAK (e.g., IRAK1 or IRAK4)) is inhibited by a compound described herein. The inhibition of the activity of a protein kinase (e.g., IRAK (e.g., IRAK1 or IRAK4)) by a compound described herein may be measured by determining the half maximal inhibitory concentration ($IC_{50}$) of the compound when the compound, or a pharmaceutical composition thereof, is contacted with the protein kinase (e.g., IRAK (e.g., IRAK1 or IRAK4)). The $IC_{50}$ values may be obtained using methods known in the art (e.g., by a competition binding assay). In certain embodiments, the $IC_{50}$ value of a compound described herein is not more than about 1 mM, not more than about 100 μM, not more than about 10 μM, not more than about 1 μM, not more than about 100 nM, not more than about 10 nM, or not more than about 1 nM.

The compounds described herein may selectively modulate the activity of a protein kinase (e.g., IRAK (e.g., IRAK1 or IRAK4)). In certain embodiments, the compounds selectively increase the activity of a protein kinase (e.g., IRAK (e.g., IRAK1 or IRAK4)). In certain embodiments, the compounds selectively inhibit the activity of a protein kinase (e.g., IRAK (e.g., IRAK1 or IRAK4)). In certain embodiments, the compounds inhibit the activity of two or more protein kinases (e.g., IRAK (e.g., IRAK1 or IRAK4)) to the same extent. In certain embodiments, the compounds increase the activity of two or more protein kinases (e.g., IRAK (e.g., IRAK1 or IRAK4)) to the same extent.

The selectivity of a compound described herein in inhibiting the activity of a first protein kinase (e.g., IRAK) over a second protein kinase may be measured by the quotient of the $IC_{50}$ value of the compound in inhibiting the activity of the second protein kinase (e.g., IRAK) over the $IC_{50}$ value of the compound in inhibiting the activity of the first protein kinase (e.g., IRAK). The selectivity of a compound described herein in modulating the activity of a first protein kinase (e.g., IRAK) over a second protein kinase may also be measured by the quotient of the $K_d$ value of an adduct of the compound and the second protein kinase over the $K_d$ value of an adduct of the compound and the first protein kinase (e.g., IRAK). In certain embodiments, the selectivity is at least about 1-fold, at least about 3-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold.

It is expected that the compounds described herein may be useful in treating and/or preventing diseases associated with aberrant activity (e.g., increased activity, undesired activity, abnormal activity) of a protein kinase (e.g., IRAK (e.g., IRAK1 or IRAK4)). It is known in the art that protein kinases are implicated in a wide range of diseases, such as proliferative diseases, inflammatory diseases, and autoimmune diseases. Therefore, the compounds described herein are expected to be useful in treating and/or preventing proliferative diseases, inflammatory diseases, and autoimmune diseases.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I'), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of a protein kinase (e.g., IRAK (e.g., an IRAK (e.g., IRAK1 or IRAK4)). In certain embodiments, a therapeutically effective amount is an amount effective for treating a disease (e.g., a disease associated with aberrant activity of an IRAK (e.g., proliferative disease)). In certain embodiments, a therapeutically effective amount is an amount effective for inhibiting the aberrant activity of an IRAK (e.g., IRAK1 or IRAK4) and treating a disease (e.g., a disease associated with aberrant activity of a protein kinase (e.g., IRAK (e.g., an IRAK (e.g., proliferative disease))). In certain embodiments, a therapeutically effective amount is an amount effective for inducing apoptosis of a cell (e.g., cell in vivo or in vitro). In certain embodiments, a prophylactically effective amount is an amount effective for inhibiting the aberrant activity of a protein kinase (e.g., IRAK (e.g., an IRAK (e.g., IRAK1 or IRAK4)). In certain embodiments, a prophylactically effective amount is an amount effective for preventing or keeping a subject in need thereof in remission of a disease (e.g., a disease associated with aberrant activity of an IRAK (e.g., proliferative disease)). In certain embodiments, a prophylactically effective amount is an amount effective for inhibiting the aberrant activity of an IRAK (e.g., IRAK1 or IRAK4), and preventing or keeping a subject in need thereof in remission of a disease (e.g., a disease associated with aberrant activity of an IRAK (e.g., proliferative disease)). In certain embodiments, a prophylactically effective amount is an amount effective for inducing apoptosis of a cell (e.g., cell in vivo or in vitro).

In certain embodiments, the effective amount is an amount effective for inhibiting the activity of a protein kinase (e.g., IRAK (e.g., an IRAK (e.g., IRAK1 or IRAK4)) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of an IRAK (e.g., IRAK1 or IRAK4) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is in vitro. In certain embodiments, the cell being contacted with a compound or composition described herein is in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a protein kinase (e.g., IRAK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZO- LASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is ibrutinib. In certain embodiments, the additional pharmaceutical agent is a protein kinase inhibitor (e.g., tyrosine protein kinase inhibitor). In certain embodiments, the additional pharmaceutical agent is a binder or inhibitor of an IRAK (e.g., IRAK1 or IRAK4). In certain embodiments, the additional pharmaceutical agent is a binder or inhibitor of IRAK1. In certain embodiments, the additional pharmaceutical agent is a binder or inhibitor of IRAK4. In certain embodiments, the additional pharmaceutical agent is a binder or inhibitor of Bruton's tyrosine kinase (BTK). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inhibiting the activity (e.g., aberrant or unwanted activity, such as increased activity) of a protein kinase (e.g., IRAK) in a subject, biological sample, tissue, or cell. In certain embodiments, the kits are useful for inducing apoptosis of a cell (e.g., cell in vivo or in vitro).

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for modulating (e.g., inhibiting) the activity (e.g., aberrant activity, such as increased activity) of a protein kinase (e.g., IRAK) in a subject, biological sample, tissue, or cell. In certain embodiments, the kits and instructions provide for inducing apoptosis of a cell. A kit described herein may include one or more additional pharmaceutical agents described herein as a separate composition.

Methods of Treatment and Uses

The present disclosure provides methods of modulating (e.g., inhibiting or increasing) the activity (e.g., aberrant activity, such as increased or decreased activity) of a protein kinase (e.g., IRAK). The present disclosure provides methods of modulating (e.g., inhibiting or increasing) the activity (e.g., aberrant activity, such as increased or decreased activity) of an IRAK (e.g., IRAK1 or IRAK4) in a subject, biological sample, or cell. The present disclosure also provides methods for the treatment of a wide range of diseases, such as diseases associated with the aberrant activity (e.g., increased activity) of a protein kinase, e.g., proliferative diseases, musculoskeletal diseases, genetic diseases, hematological diseases, neurological diseases, painful conditions, psychiatric disorders, and metabolic disorders in a subject in need thereof. The present disclosure provides methods for the treatment and/or prevention of a proliferative disease (e.g., cancers (e.g., leukemia, lymphoma), inflammatory diseases, autoinflammatory diseases, and autoimmune diseases.

In another aspect, the present disclosure provides methods of modulating the activity of a protein kinase (e.g., IRAK (e.g., IRAK1 or IRAK4)) in a subject, biological sample, or cell. In certain embodiments, provided are methods of inhibiting the activity of a protein kinase in a subject. In certain embodiments, provided are methods of inhibiting the activity of a protein kinase in a cell. In certain embodiments, provided are methods of increasing the activity of a protein kinase (e.g., IRAK (e.g., IRAK1 or IRAK4) in a subject. The compounds described herein may exhibit kinase inhibitory activity; the ability to inhibit interleukin-1 receptor-associated kinase (IRAK); the ability to inhibit interleukin-1 receptor-associated kinase (IRAK) 1 (IRAK1); the ability to inhibit IRAK1, without inhibiting another kinase (e.g., an interleukin-1 receptor-associated kinase (e.g., IRAK)); the ability to inhibit IRAK4, without inhibiting another kinase (e.g., an interleukin-1 receptor-associated kinase (e.g., IRAK)); a therapeutic effect and/or preventative effect in the treatment of cancers; a therapeutic effect and/or preventative effect in the treatment of proliferative diseases; and/or a therapeutic profile (e.g., optimum safety and curative effect) that is superior to existing chemotherapeutic agents.

In certain embodiments, provided are methods of increasing the activity of a protein kinase (e.g., IRAK (e.g., IRAK1 or IRAK4)) in a subject or cell by a method described herein. In certain embodiments, provided are methods of decreasing the activity of a protein kinase (e.g., IRAK (e.g., IRAK1 or IRAK4)) in a subject or cell by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a protein kinase (e.g., IRAK (e.g., IRAK1 or IRAK4)) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a protein kinase (e.g., IRAK (e.g., IRAK1 or IRAK4)) in a subject or cell is selectively inhibited by the method. In some embodiments, the activity of a protein kinase (e.g., IRAK (e.g., IRAK1 or IRAK4)) in a subject or cell is selectively decreased by the method.

Without wishing to be bound by any particular theory, the compounds described herein are able to bind (e.g., covalently modify) the protein kinase being inhibited. In certain embodiments, a compound described herein is able to bind (e.g., covalently modify) the protein kinase. In certain embodiments, the compound described herein is able to covalently bind a cysteine residue of the protein kinase. In certain embodiments, the compound is capable of covalently modifying IRAK1 (e.g., Cys302) of IRAK1. In certain embodiments, the compound is capable of covalently modifying IRAK4.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein. In another aspect, the present disclosure provides methods of inhibiting the activity of a protein kinase (e.g., IRAK (e.g., IRAK1 or IRAK4) in a biological sample, the methods comprising contacting the biological sample with an effective amount of a compound, or pharmaceutical composition thereof, as described herein. In another aspect, the present disclosure provides methods of inhibiting the activity of a protein kinase in a tissue or cell, the methods comprising contacting the tissue or cell with an effective amount of a compound, or pharmaceutical composition thereof, as described herein.

In another aspect, the present disclosure provides methods of inhibiting the activity of a protein kinase (e.g., IRAK (e.g., IRAK1 or IRAK4) in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the biological sample being contacted with the compound or composition is breast tissue, bone marrow, lymph node, lymph tissue, spleen, or blood. In certain embodiments, the biological sample being contacted with the compound or composition is a tumor or cancerous tissue. In certain embodiments, the biological sample being contacted with the compound or composition is serum, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

In certain embodiments, the cell or tissue being contacted with the compound or composition is present in vitro. In certain embodiments, the cell or tissue being contacted with the compound or composition is present in vivo. In certain embodiments, the cell or tissue being contacted with the compound or composition is present ex vivo. In certain embodiments, the cell or tissue being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant white blood cell. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a breast carcinoma cell. In certain embodiments, the cell being contacted with the compound or composition is a sarcoma cell. In certain embodiments, the cell being contacted with the compound or composition is a sarcoma cell from breast tissue.

The proliferative disease to be treated or prevented using the compounds described herein may be associated with the overexpression of a kinase, such as an interleukin-1 receptor-associated kinase (IRAK). IRAK1 and IRAK4 are serine/threonine-protein kinases that play a role in initiating innate immune response against foreign pathogens. They are involved in Toll-like receptor (TLR) and IL-1R signaling pathways, and are rapidly recruited by MYD88 to the receptor-signaling complex upon TLR activation. Association with MYD88 leads to IRAK1 phosphorylation by IRAK4 and subsequent autophosphorylation and kinase activation of IRAK1 (*Immunity*, 1997, 7(6), 837-47). IRAK4−/− mice have abolished cellular responses to various IL-1 and TLR ligands and are severely impaired in their response to viral and bacterial challenges. IRAK1−/− mice show a similar but partial response.

In certain embodiments, the proliferative disease to be treated or prevented using the compounds described herein may be associated with the overexpression of an IRAK (e.g., IRAK1 or IRAK4).

A proliferative disease may be associated with aberrant activity of an IRAK (e.g., IRAK1 or IRAK4). Aberrant activity of an IRAK (e.g., IRAK1 or IRAK4) may be elevated and/or inappropriate or undesired activity of the IRAK. Deregulation of cell cycle progression is a characteristic of a proliferative disease, and a majority of proliferative diseases have abnormalities in some component of IRAK (e.g., IRAK1 or IRAK4) activity, frequently through elevated and/or inappropriate IRAK activation. In certain embodiments, IRAK is not overexpressed, and the activity of IRAK is elevated and/or inappropriate. In certain embodiments, IRAK1 is overexpressed, and the activity of IRAK1 is elevated and/or inappropriate. In certain embodiments, IRAK4 is overexpressed, and the activity of IRAK4 is elevated and/or inappropriate. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of IRAK1 and be useful in treating and/or preventing proliferative diseases. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of IRAK4 and be useful in treating and/or preventing proliferative diseases. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of IRAK1 and be useful in treating and/or preventing proliferative diseases.

All types of biological samples described herein or known in the art are contemplated as being within the scope of the invention. In certain embodiments, the proliferative disease to be treated or prevented using the compounds described herein is cancer. All types of cancers disclosed herein or known in the art are contemplated as being within the scope of the invention. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myeloid leukemia (AML). In certain embodiments, the proliferative disease is acute monocytic leukemia (AMoL). In certain embodiments, the proliferative disease is Waldenstrim's macroglobulinemia. In certain embodiments, the proliferative disease is Waldenstrim's macroglobulinemia associated with the MYD88 L265P somatic mutation. In certain embodiments, the proliferative disease is myelodysplastic syndrome (MDS). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis.

In certain embodiments, the proliferative disease is an acute inflammatory disease. In certain embodiments, the proliferative disease is an inflammatory disease. In certain embodiments, the acute inflammatory disease is rheumatoid arthritis, Crohn's disease, or fibrosis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Another aspect of the invention relates to methods of inhibiting the activity of a kinase in a biological sample, tissue, cell, or subject. In certain embodiments, the kinase is an IRAK. In certain embodiments, the kinase is IRAK1. In certain embodiments, the kinase is IRAK4. In certain embodiments, the activity of the kinase is aberrant activity of the kinase. In certain embodiments, the activity of the kinase is increased activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound described herein to the kinase.

The present invention provides methods of inhibiting cell growth in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of an IRAK. In certain embodiments, the additional pharmaceutical agent is an inhibitor of IRAK1. In certain embodiments, the additional pharmaceutical agent is an inhibitor of IRAK4. In certain embodiments, the additional pharmaceutical agent is a selective inhibitor of IRAK1. In certain embodiments, the additional pharmaceutical agent is a selective inhibitor of IRAK4. In certain embodiments, the additional pharmaceutical agent is a non-selective inhibitor of IRAK1. In certain embodiments, the additional pharmaceutical agent is a non-selective inhibitor of IRAK4. In certain embodiments, the additional pharmaceutical agent includes an anti-cancer agent (e.g., chemotherapeutics), anti-inflammatory agent, steroids, immunosuppressant, radiation therapy, or other agents. In certain embodiments, the additional pharmaceutical agent is an anti-proliferative agent. In certain embodiments, the additional pharmaceutical agent is an inhibitor of a kinase. In certain embodiments, the additional pharmaceutical agent is a non-selective inhibitor of Bruton's tyrosine kinase (BTK). In certain embodiments, the additional pharmaceutical agent is a selective inhibitor of BTK. In certain embodiments, the additional pharmaceutical agent is flavopiridol, triptolide, SNS-032 (BMS-387032), PHA-767491, PHA-793887, BS-181, (S)-CR8, (R)-CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a calmodulin-dependent kinase (CaM Kinase). In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. Exemplary chemotherapeutic agents include alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as vinca alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant. Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine. In certain embodiments, a pharmaceutical composition described herein further comprises a combination of the additional pharmaceutical agents described herein.

The inventive compounds or compositions may synergistically augment inhibition of IRAK1 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of the protein kinase being inhibited is selectively inhibited by the compounds or pharmaceutical compositions described herein, compared to the activity of a different protein (e.g., a different protein kinase). In certain embodiments, the activity of IRAK (e.g., IRAK1) is selectively inhibited by a compound or pharmaceutical composition described herein, compared to the activity of a different protein. In certain embodiments, the activity of IRAK1 is selectively inhibited by a compound or pharmaceutical composition described herein, compared to the activity of another IRAK (e.g., IRAK4). In certain embodiments, the activity of IRAK4 is selectively inhibited by a compound or pharmaceutical composition described herein, compared to the activity of another IRAK (e.g., IRAK1).

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating a proliferative disease (e.g., cancers (e.g., leukemia, lymphoma), inflammatory diseases, autoinflammatory diseases, and autoimmune diseases in a subject in need thereof, preventing a proliferative disease in a subject in need thereof, inhibiting the activity of a protein kinase (e.g., IRAK (e.g., IRAK1 or IRAK4)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., IRAK (e.g., IRAK1 or IRAK4)) in a subject, biological sample, tissue, or cell, and/or inducing apoptosis in a cell. A kit described herein may include one or more additional pharmaceutical agents described herein as a separate composition.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Structure-Activity Analyses for Selected Compounds

Select compounds described herein were evaluated for structure-activity analyses. Exemplary results are shown in Table 1. For IRAK1, the following Alexa kinase assay procedure was followed: in the absence of an inhibitor, ADP formed by a kinase reaction will displace an Alexa Fluor 647 dye-labeled ADP tracer from an Eu3+-labeled anti-ADP antibody, resulting in a decrease in the time-resolved fluorescence resonance energy transfer (TR-FRET) signal. In the presence of an inhibitor, the amount of ADP formed by the kinase reaction is reduced, and the resulting intact antibody-tracer interaction produces a high TR-FRET signal. For IRAK4, the following Z-lyte kinase assay procedure was followed: phosphorylation-dependent protease susceptibility of a double-labeled peptide substrate is detected using fluorescence resonance energy transfer (FRET).

TABLE 1

$IC_{50}$ values of exemplary compounds described herein.

| Compound | IRAK1 (nM) | IRAK4 (nM) |
|---|---|---|
| 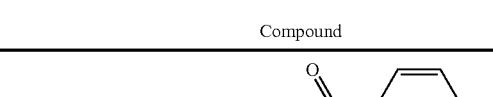 JH-X-119-01 | 9 | >10,000 |

TABLE 1-continued

IC$_{50}$ values of exemplary compounds described herein.

| Compound | | IRAK1 (nM) | IRAK4 (nM) |
|---|---|---|---|
| JH-X-119-03 | | 55 | >10,000 |
| JH-X-159 | | 259 | >10,000 |
| JH-X-119-02 | | 47 | >10,000 |
| JH-X-119-04 | | 25 | >10,000 |
| JH-X-198 | | 51 | >10,000 |

TABLE 1-continued
IC$_{50}$ values of exemplary compounds described herein.
| Compound | | IRAK1 (nM) | IRAK4 (nM) |
|---|---|---|---|
| 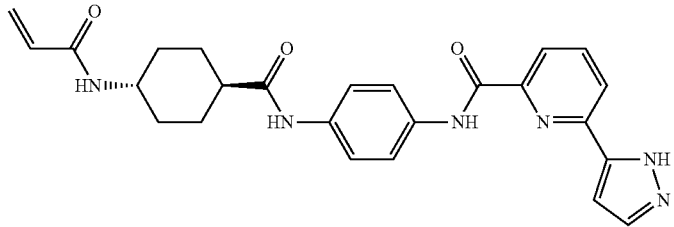 [SMILES: C=CC(=O)N[C@H]1CC[C@H](C(=O)Nc2ccc(NC(=O)c3cccc(-c4ccn[nH]4)n3)cc2)CC1] | JH-XII-205-1 | 88 | 1,110 |
| 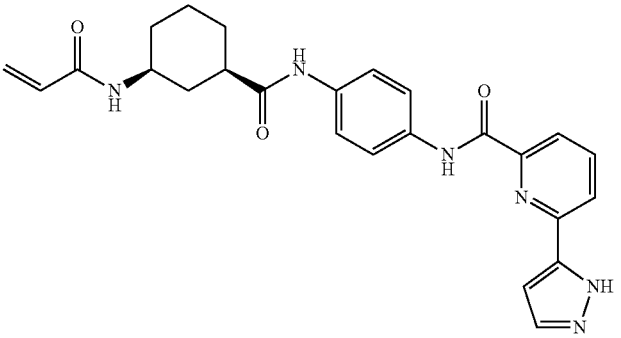 [SMILES: C=CC(=O)N[C@H]1CCC[C@@H](C(=O)Nc2ccc(NC(=O)c3cccc(-c4ccn[nH]4)n3)cc2)C1] | JH-XII-205-2 | 72 | >10,000 |
| 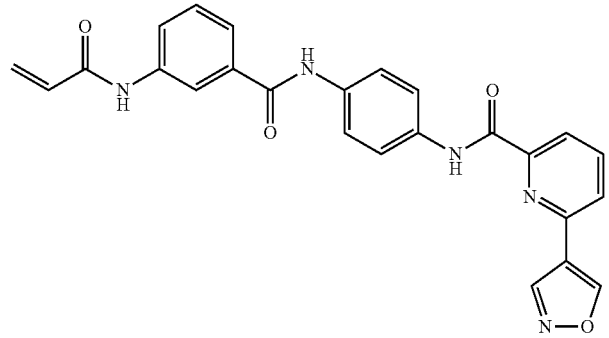 [SMILES: C=CC(=O)Nc1cccc(C(=O)Nc2ccc(NC(=O)c3cccc(-c4cnoc4)n3)cc2)c1] | JH-XIII-80-1 | 12 | >10,000 |
| 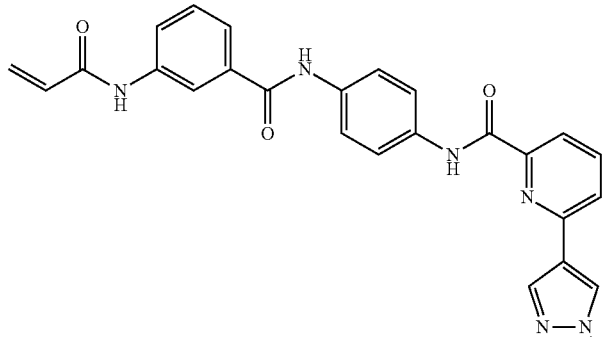 | JH-XIII-80-2 | 67 | >10,000 |
| 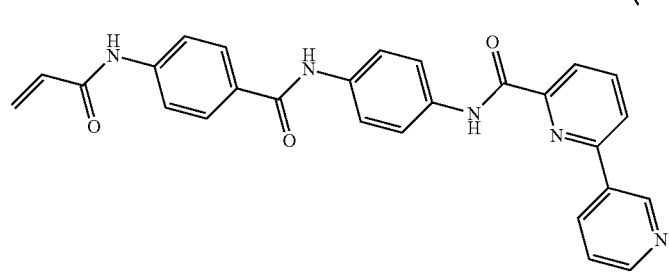 | JH-XIII-77 | 80 | >10,000 |

TABLE 1-continued

IC$_{50}$ values of exemplary compounds described herein.

| Compound | | IRAK1 (nM) | IRAK4 (nM) |
|---|---|---|---|
| | JH-XIII-80-3 | 22 | >10,000 |
| | JH-XII-200-1 | 46 | 154 |
| | JH-XII-200-2 | 24 | 648 |
| | JH-XII-200-3 | 51 | 607 |
| | JH-XIII-96-2 | 40 | >10,000 |

TABLE 1-continued
IC$_{50}$ values of exemplary compounds described herein.
| Compound | IRAK1 (nM) | IRAK4 (nM) |
|---|---|---|
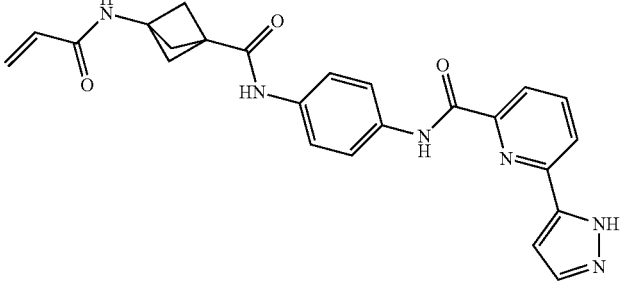
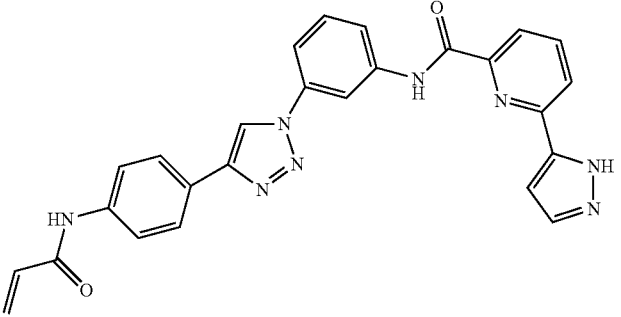 [SMILES: C=CC(=O)Nc1ccc(-c2cn(-c3cccc(NC(=O)c4cccc(-c5ccn[nH]5)n4)c3)nn2)cc1]
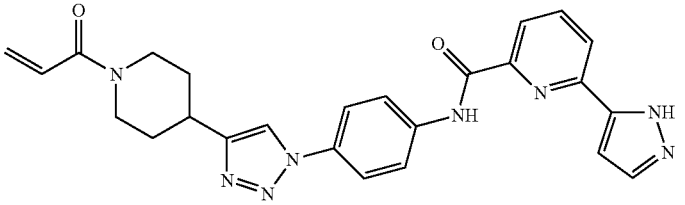 [SMILES: C=CC(=O)N1CCC(c2cn(-c3ccc(NC(=O)c4cccc(-c5ccn[nH]5)n4)cc3)nn2)CC1]
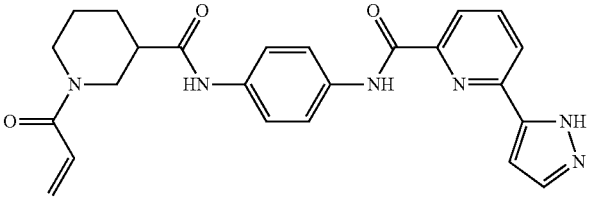 [SMILES: C=CC(=O)N1CCCC(C(=O)Nc2ccc(NC(=O)c3cccc(-c4ccn[nH]4)n3)cc2)C1]
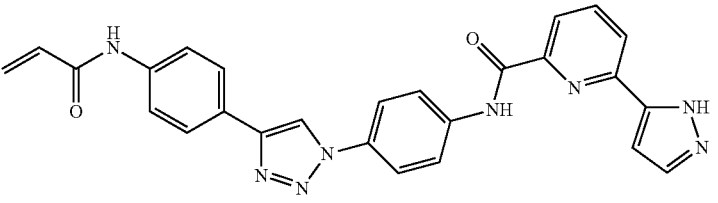 [SMILES: C=CC(=O)Nc1ccc(-c2cn(-c3ccc(NC(=O)c4cccc(-c5ccn[nH]5)n4)cc3)nn2)cc1]
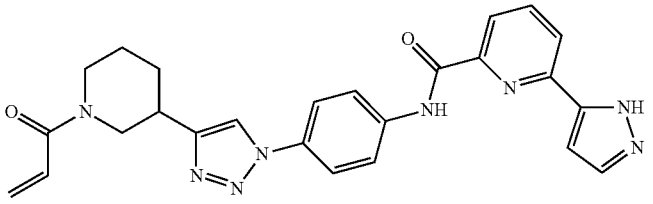 [SMILES: C=CC(=O)N1CCCC(c2cn(-c3ccc(NC(=O)c4cccc(-c5ccn[nH]5)n4)cc3)nn2)C1]

TABLE 1-continued

IC$_{50}$ values of exemplary compounds described herein.

| Compound | IRAK1 (nM) | IRAK4 (nM) |
|---|---|---|

Preparation of the Compounds Described Herein

The compounds provided herein can be prepared from readily available starting materials using the following general methods and procedures. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

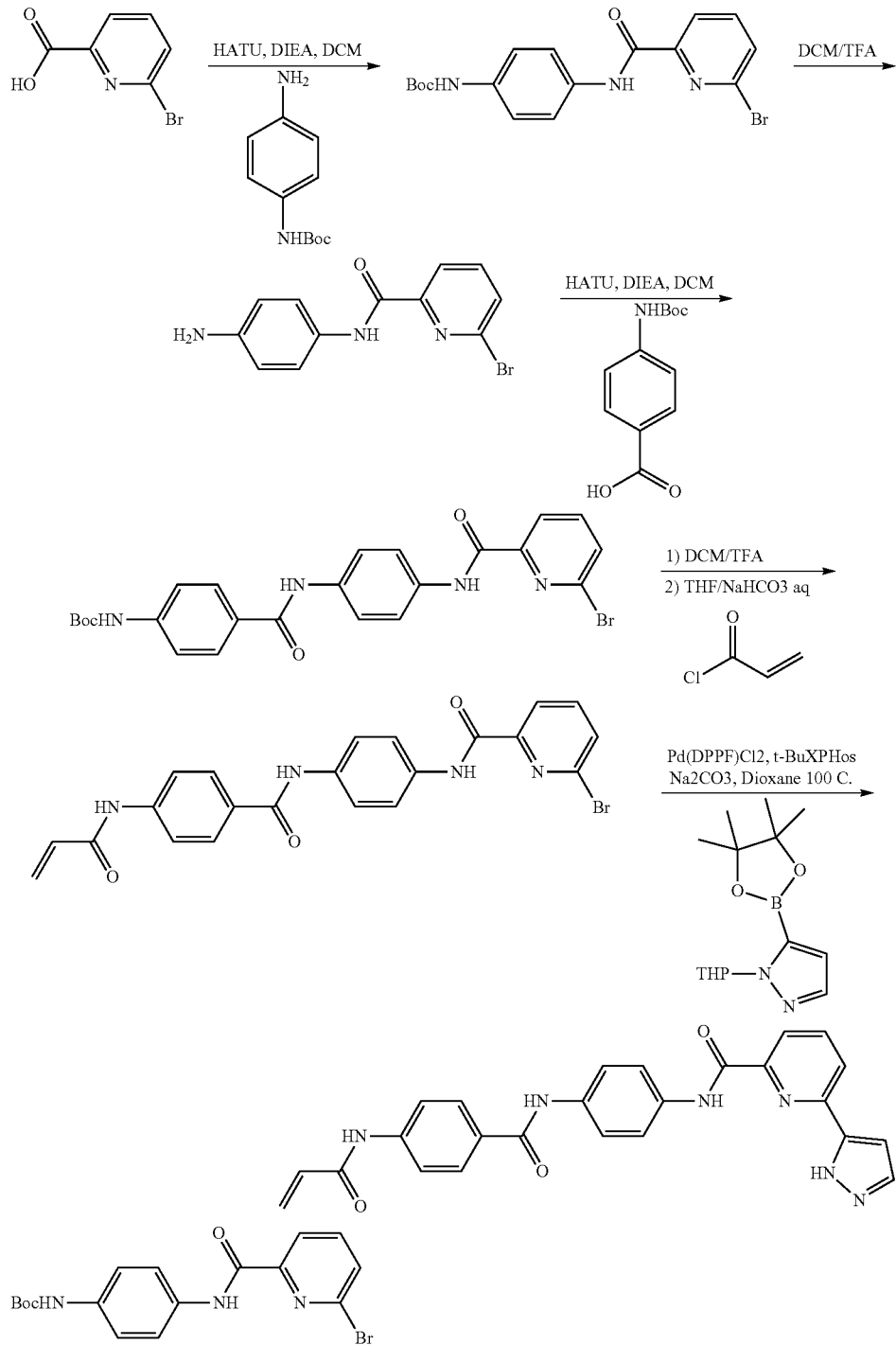

tert-butyl (4-(6-bromopicolinamido)phenyl)carbamate

To a solution of 6-bromopicolinic acid (1.6 g, 7.92 mmol) in DCM (100 mL) was added tert-butyl (4-aminophenyl) carbamate (1.81 g, 8.71 mmol) and HATU (6.02 g, 15.84 mmol) followed by DIEA (6.90 mL, 39.60 mmol). The mixture was stirred for 1 hour at room temperature. Water (50 mL) was added and the mixture was extracted with DCM (2×50 mL). The combined organic layer was washed with brine, dried over MgSO$_4$, and condensed. The crude material was triturated with EtOAc (20 mL), filtered and dried under N$_2$ to give a white powder that was used without further purification (1.58 g, 51% yield) m/z expected: 392.25, observed: 392.64

The following compound was synthesized according to the above procedure:

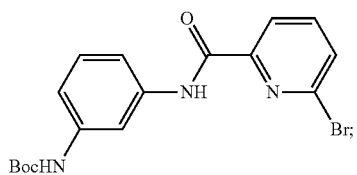 [SMILES: CC(C)(C)OC(=O)Nc1cccc(NC(=O)c2cccc(Br)n2)c1]

White powder (1.73 g, 56% yield) m/z expected: 392.25, observed: 392.53

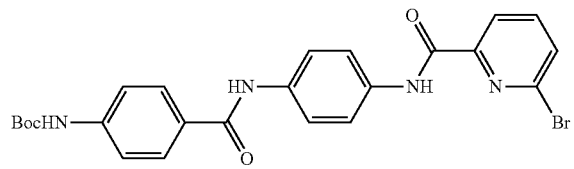

tert-butyl (4-((4-(6-bromopicolinamido)phenyl)carbamoyl)phenyl)carbamate

To a solution of tert-butyl (4-(6-bromopicolinamido)phenyl)carbamate (1.58 g, 4.03 mmol) in DCM (100 mL) was added TFA (10 mL). The mixture was stirred for 1 hour. The solvent was removed in vacuo and the material was dissolved in DCM (100 mL). 4-((tert-butoxycarbonyl)amino)benzoic acid (1.05 g, 4.43 mmol) and HATU (3.06 g, 8.06 mmol) followed by DIEA (2.75 mL, 20.14 mmol). The mixture was stirred for 1 hour at room temperature. Water (50 mL) was added and the mixture was extracted with DCM (2×50 mL). The combined organic layer was washed with brine, dried over MgSO$_4$, and condensed. The crude material was purified by flash chromatography using a gradient of 20-80% EtOAc in Hexanes to give the desired compound as a white solid. (0.70 g, 34% yield) m/z expected: 511.38, observed: 512.47

The following compounds in Table 2 were synthesized according to the above procedure.

TABLE 2

| Structure | Yield | LCMS |
|---|---|---|
| 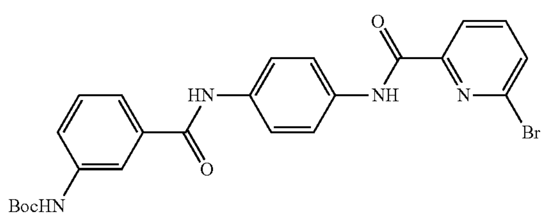 [SMILES: CC(C)(C)OC(=O)Nc1cccc(C(=O)Nc2ccc(NC(=O)c3cccc(Br)n3)cc2)c1] | 30% | 512.78 |
| 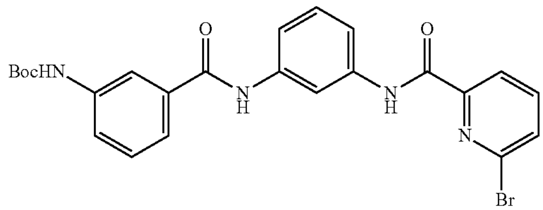 [SMILES: CC(C)(C)OC(=O)Nc1cccc(C(=O)Nc2cccc(NC(=O)c3cccc(Br)n3)c2)c1] | 42% | 512.68 |
| 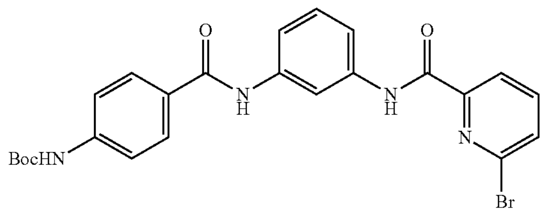 [SMILES: CC(C)(C)OC(=O)Nc1ccc(C(=O)Nc2cccc(NC(=O)c3cccc(Br)n3)c2)cc1] | 48% | 512.35 |

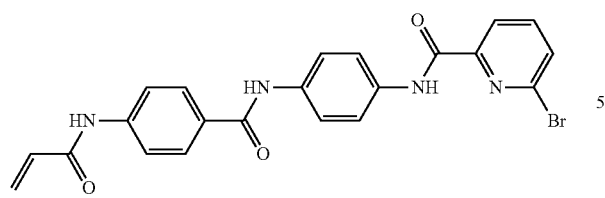

N-(4-(4-acrylamidobenzamido)phenyl)-6-bromopicolinamide

To a solution of tert-butyl (4-((4-(6-bromopicolinamido)phenyl)carbamoyl) phenyl)carbamate (100 mg, 0.19 mmol) in DCM (10 mL) was added TFA (1 mL). The mixture was stirred for 1 hour then the solvent was removed in vacuo. The material was dissolved in THF (5 mL) and NaHCO$_3$ sat. aq. (5 mL). Acryloyl chloride (19 µL, 0.23 mmol) was added and the mixture stirred for 30 minutes. Water (20 mL) was added and the mixture was extracted with EtOAc (2×50 mL). The combined organic layer was washed with brine, dried over MgSO$_4$, and condensed to give a white solid that was used without further purification. (84 mg, 92% yield) m/z expected: 465.31, observed: 467.52

The following compounds in Table 3 were synthesized according to the above procedure.

TABLE 3

| Structure | Yield | LCMS |
|---|---|---|
| 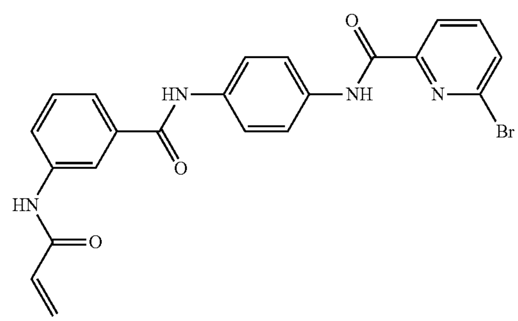 [SMILES: C=CC(=O)Nc1cccc(C(=O)Nc2ccc(NC(=O)c3cccc(Br)n3)cc2)c1] | 96% | 467.19 |
| 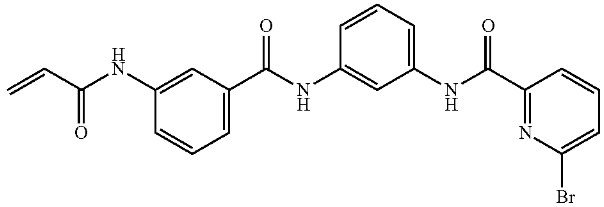 [SMILES: C=CC(=O)Nc1cccc(C(=O)Nc2cccc(NC(=O)c3cccc(Br)n3)c2)c1] | 88% | 467.23 |
| 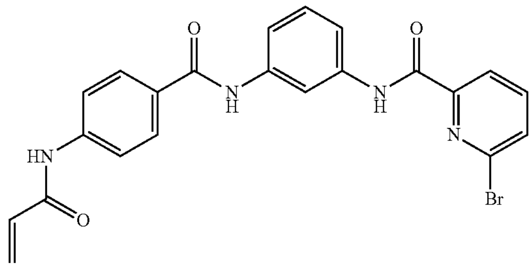 [SMILES: C=CC(=O)Nc1ccc(C(=O)Nc2cccc(NC(=O)c3cccc(Br)n3)c2)cc1] | 84% | 467.51 |

TABLE 3-continued

| Structure | Yield | LCMS |
|---|---|---|
| (structure) | 79% | 522.71 |
| (structure) | 82% | 522.32 |

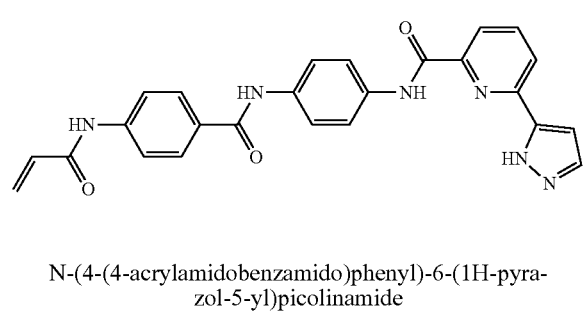

N-(4-(4-acrylamidobenzamido)phenyl)-6-(1H-pyrazol-5-yl)picolinamide

N-(4-(4-acrylamidobenzamido)phenyl)-6-bromopicolinamide (84 mg, 0.18 mmol) was dissolved in 1,4-Dioxane (5 mL). 1-(tetrahydro-2H-pyran-2-yl)-5-(4,4,5,5-tetramethyl-1,3,2-dioxaborolan-2-yl)-1H-pyrazole (55 mg, 0.19 mmol) was added followed by Na$_2$CO$_3$ 2M aqueous solution (0.54 mL, 1.08 mmol). The mixture was degassed in a sonicator for 2 minutes. Pd(dppf)Cl$_2$ (16 mg, 0.021 mmol) and t-BuXPhos (13 mg, 0.032 mmol) were added and the mixture heated to 90° C. in a sealed vial for 1 hour. The reaction was quenched with water (10 mL) and extracted with EtOAC (2×50 mL) washed with brine, dried over MgSO$_4$ and condensed. The crude material was dissolved in DCM (10 mL) and TFA (1 mL) was added. The mixture was stirred for 30 minutes and the solvent removed in vacuo. The crude material was purified by reversed phase HPLC to give the desired compound as a white solid (46 mg, 56% yield) m/z expected: 452.47, observed: 453.19; $^1$H NMR (500 MHz DMSO) δ 14.06, (Br, 1H), 10.67 (Br, 1H), 10.35 (d, J=20 Hz, 2H), 8.18 (s, 1H), 8.15-8.08 (m, 3H), 7.94 (d, J=9 Hz, 1H), 7.85 (q, J=12 Hz, 4H) 7.75 (Br, 1H), 7.69 (d, J=10 Hz, 1H), 7.50 (t, J=9 Hz, 1H), 7.18 (Br, 1H), 6.47 (dd, J=10 Hz, 15 Hz, 1H), 6.33-6.28 (m, 1H), 5.80 (dd, J=3 Hz, 10 Hz, 1H).

The following compounds in Table 4 were synthesized according to the above procedure.

TABLE 4

| Structure | Yield | LCMS | $^1$H NMR (500 MHz DMSO) |
|---|---|---|---|
| (structure) | 49% | 453.36 | δ 14.04 (Br, 1H), 10.66, (s, 1H), 10.44 (s, 1H), 10.19 (s, 1H), 8.14-8.07 (m, 3H), 7.98 (d, J = 9Hz, 2H), 7.87-7.81 (m, 6H), 7.75 (Br, 1H), 7.19 (Br, 1H), 6.48 (dd, J = 10 Hz, 16 Hz, 1H), 6.34-6.29 (m, 1H), 5.82 (dd, J = 3 Hz, 11 Hz, 1H) |

TABLE 4-continued

| Structure | Yield | LCMS | ¹H NMR (500 MHz DMSO) |
|---|---|---|---|
| 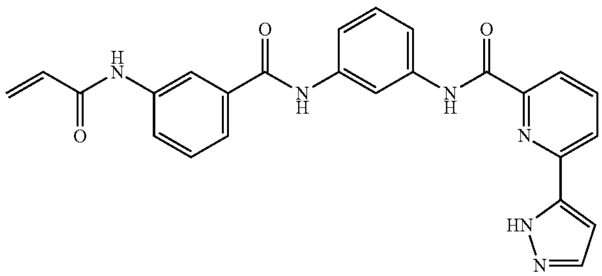 [SMILES: C=CC(=O)Nc1cccc(C(=O)Nc2cccc(NC(=O)c3cccc(-c4ccn[nH]4)n3)c2)c1] | 58% | 453.07 | δ 10.69 (s, 1H), 10.37 (d, J = 10 Hz, 2H), 8.38 (s, 1H), 8.19 (s, 1H), 8.15-8.08 (m, 3H), 7.93 (d, J = 9 Hz, 1H), 7.74 (Br, 1H), 7.69 (d, J = 8 Hz, 1H), 7.62 (d, J = 7 Hz, 1H), 7.57 (d, J = 8 Hz, 1H), 7.50 (t, J = 8 Hz, 1H), 7.40 (t, J = 8 Hz, 1H), 7.17 (Br, 1H), 6.47 (dd, J = 11 Hz, 17 Hz, 1H), 6.33-6.28 (m, 1H), 5.80 (dd, J = 2Hz, 10 Hz, 1H) |
| 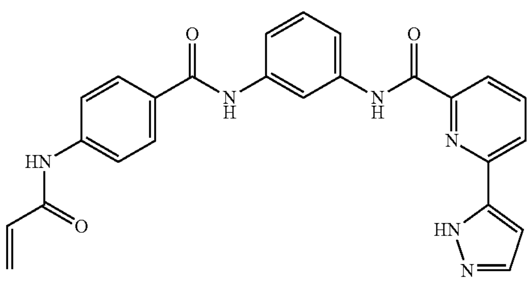 [SMILES: C=CC(=O)Nc1ccc(C(=O)Nc2cccc(NC(=O)c3cccc(-c4ccn[nH]4)n3)c2)cc1] | 54% | 453.56 | δ 10.69 (s, 1H), 10.45 (s, 1H), 10.26 (s, 1H), 8.40 (s, 1H), 8.14-8.08 (m, 3H), 8.00 (d, J = 9 Hz, 2H), 7.82 (d, J = 9 Hz, 2H), 7.74 (Br, 1H), 7.59 (t, J = 10 Hz, 2H), 7.39 (t, J = 7 Hz, 1H), 7.17 (Br, 1H), 6.48 (dd, J = 10 Hz, 16 Hz, 1H), 6.35-6.29 (m, 1H), 5.82 (dd, J = 3 Hz, 10 Hz, 1H) |
| 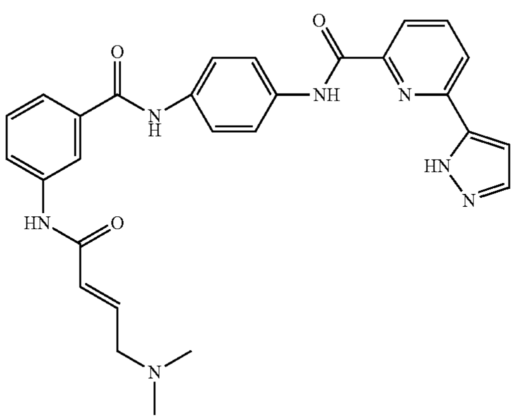 [SMILES: CN(C)C/C=C/C(=O)Nc1cccc(C(=O)Nc2ccc(NC(=O)c3cccc(-c4ccn[nH]4)n3)cc2)c1] | 45% | 510.27 | |
| 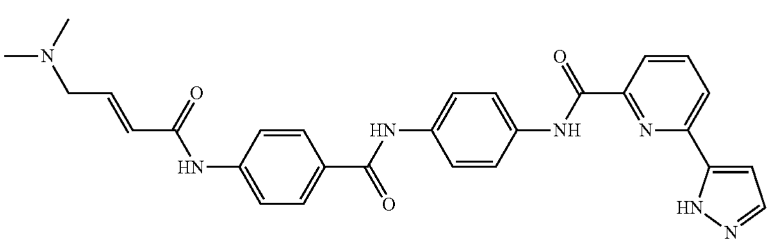 [SMILES: CN(C)C/C=C/C(=O)Nc1ccc(C(=O)Nc2ccc(NC(=O)c3cccc(-c4ccn[nH]4)n3)cc2)cc1] | 47% | 510.38 | |

Preparation of Further Compounds Described Herein

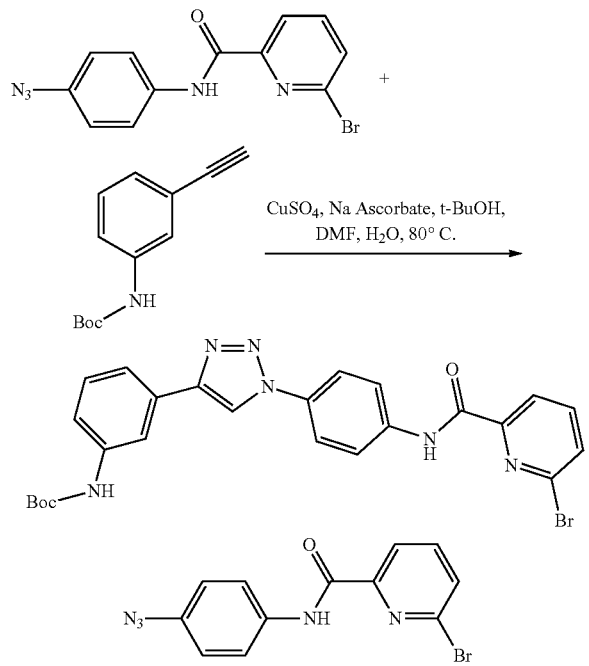

N-(4-azidophenyl)-6-bromopicolinamide

Prepared using the same procedure as for the synthesis of tert-butyl (4-(6-bromopicolinamido)phenyl)carbamate described above to give a yellow solid that was used without further purification (72% yield). M/z expected: 318.13, observed: 318.57

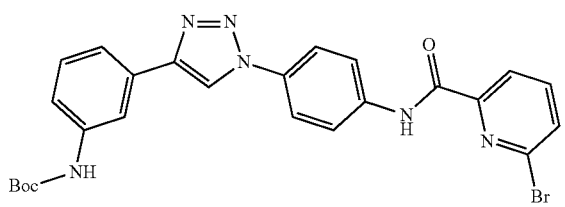 [SMILES: CC(C)(C)OC(=O)Nc1cccc(-c2cn(-c3ccc(NC(=O)c4cccc(Br)n4)cc3)nn2)c1]

tert-butyl (3-(1-(4-(6-bromopicolinamido)phenyl)-1H-1,2,3-triazol-4-yl)phenyl)carbamate N-(4-azidophenyl)-6-bromopicolinamide (200 mg, 0.629 mmol) and tert-butyl (3-ethynylphenyl)carbamate (137 mg, 0.629 mmol) were dissolved in a 1:1:1 solution of t-BuOH, DMF and H$_2$O (6 mL). CuSO$_4$ Pentahydrate (157 mg, 0.629 mmol) and Na Ascorbate (125 mg, 0.629 mmol) were added and the mixture stirred at 80° C. for 1 hour. Water was added and the precipitate filtered, washed with water and dried under vacuum to give the desired product as a yellow solid that was used without further purification (268 mg, 80% yield). M/z expected: 535.40, observed: 537.39

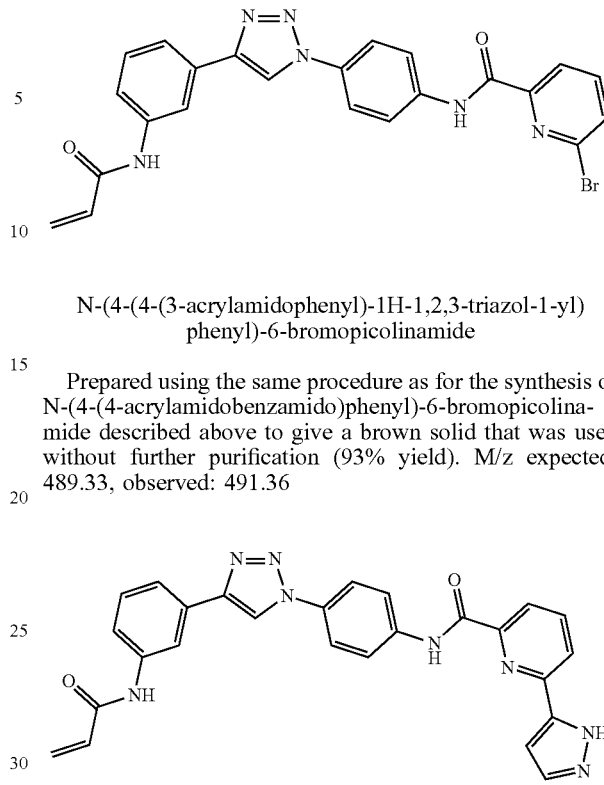

N-(4-(4-(3-acrylamidophenyl)-1H-1,2,3-triazol-1-yl)phenyl)-6-bromopicolinamide Prepared using the same procedure as for the synthesis of N-(4-(4-acrylamidobenzamido)phenyl)-6-bromopicolinamide described above to give a brown solid that was used without further purification (93% yield). M/z expected: 489.33, observed: 491.36

N-(4-(4-(3-acrylamidophenyl)-1H-1,2,3-triazol-1-yl)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (58% yield). M/z expected: 476.50, observed: 477.26. $^1$H NMR (500 MHz DMSO) δ 10.81, (Br, 1H), 10.26 (s, 1H), 9.22 (s, 1H), 8.29 (s, 1H), 8.13-8.04 (m, 6H), 7.98 (d, J=9 Hz, 2H), 7.64 (d, J=7 Hz, 2H), 7.56 (d, J=7 Hz, 1H), 7.39 (t, J=10 Hz, 1H), 6.42 (dd, J=10 Hz, 15 Hz, 1H), 6.26-6.22 (m, 1H), 5.73 (dd, J=3 Hz, 10 Hz, 1H). IRAK1 IC50=40 nM, IRAK4 IC50>10,000 nM.

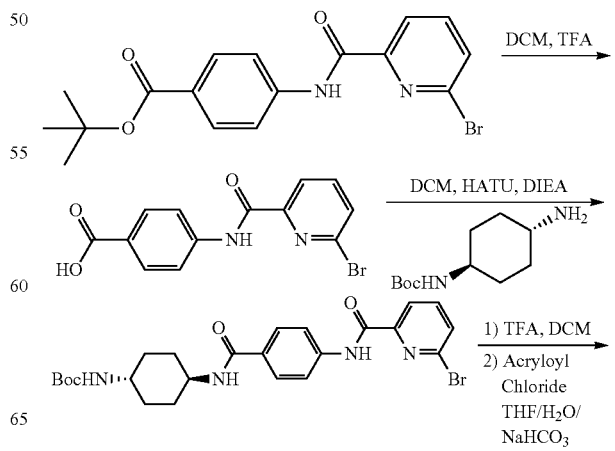

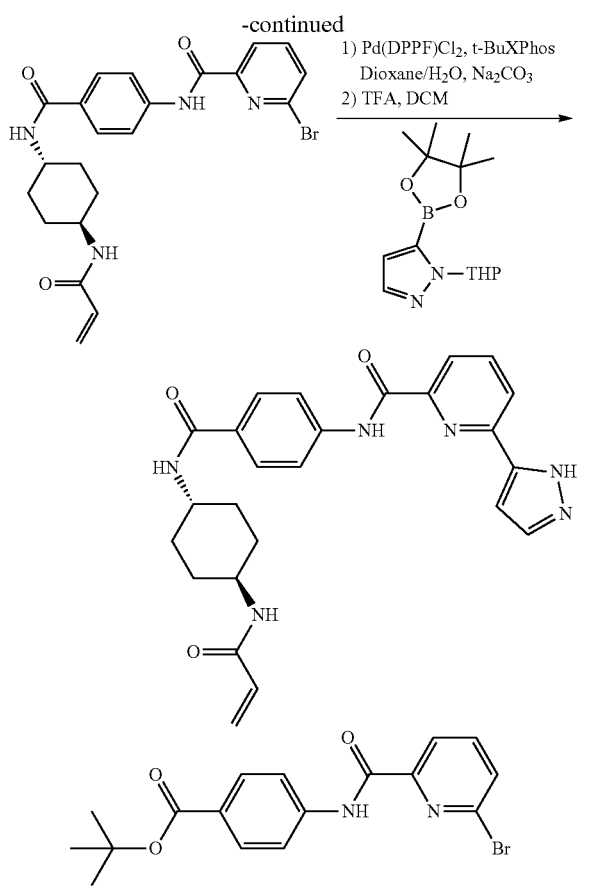

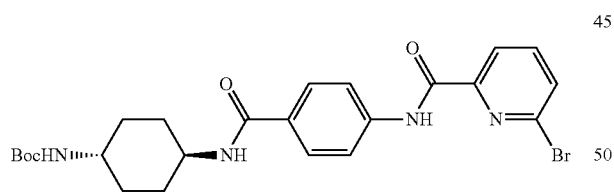

tert-butyl 4-(6-bromopicolinamido)benzoate

Prepared using the same procedure as for the synthesis of tert-butyl (4-(6-bromopicolinamido)phenyl)carbamate described above to give a white solid that was used without further purification (54% yield). M/z expected: 377.24, observed: 377.56

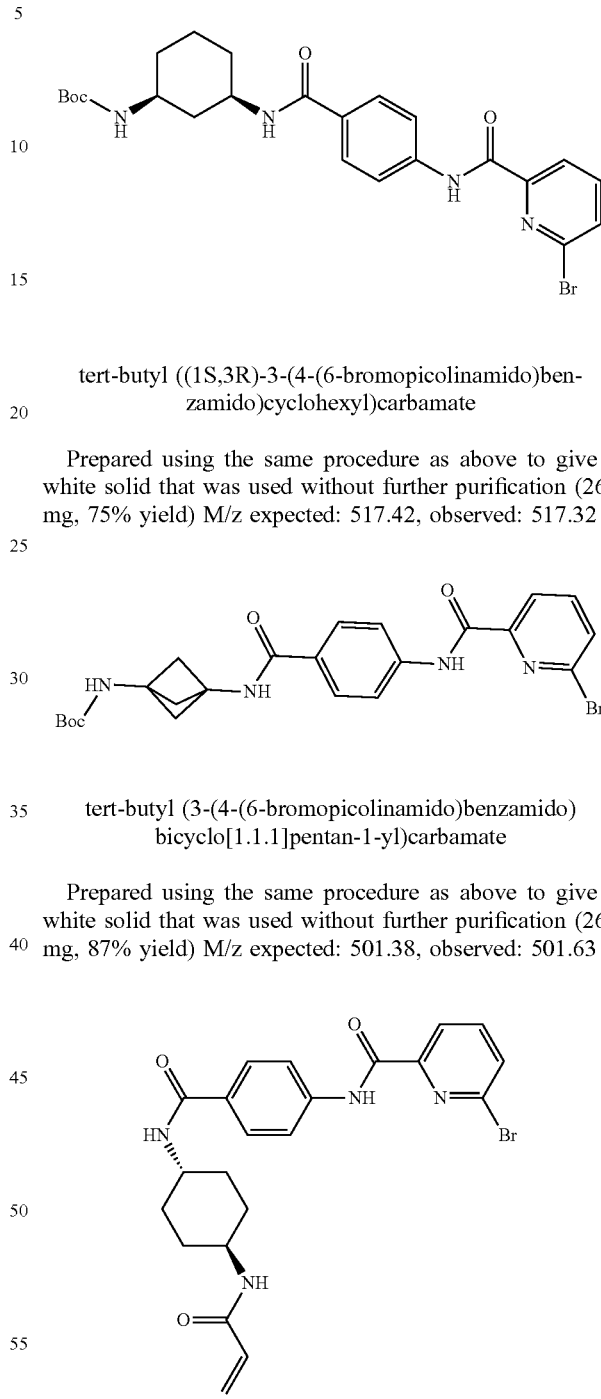

tert-butyl ((1r,4r)-4-(4-(6-bromopicolinamido)benzamido)cyclohexyl)carbamate To a solution of tert-butyl 4-(6-bromopicolinamido)benzoate (250 mg, 0.66 mmol) in DCM (10 mL) was added TFA (1 mL). The solution was stirred for 3 hours at room temperature and the solvent removed. The residue was dissolved in DCM (10 mL) and tert-butyl ((1r,4r)-4-aminocyclohexyl)carbamate (156 mg, 0.73 mmol) was added along with HATU (503 mg, 1.32 mmol) and DIEA (577 µL, 3.31 mmol). The solution was stirred for 1 hour at which time the resulting precipitate was filtered and washed with cold DCM and dried under vacuum to give the desired product as a yellow solid that was used without further purification (246 mg, 78% yield). M/z expected: 517.42, observed: 517.39 tert-butyl ((1S,3R)-3-(4-(6-bromopicolinamido)benzamido)cyclohexyl)carbamate Prepared using the same procedure as above to give a white solid that was used without further purification (260 mg, 75% yield) M/z expected: 517.42, observed: 517.32 tert-butyl (3-(4-(6-bromopicolinamido)benzamido)bicyclo[1.1.1]pentan-1-yl)carbamate Prepared using the same procedure as above to give a white solid that was used without further purification (260 mg, 87% yield) M/z expected: 501.38, observed: 501.63

N-(4-(((1r,4r)-4-acrylamidocyclohexyl)carbamoyl)phenyl)-6-bromopicolinamide

Prepared using the same procedure as for the synthesis of N-(4-(4-acrylamidobenzamido)phenyl)-6-bromopicolinamide described above to give a brown solid that was used without further purification (91% yield). M/z expected: 471.36, observed: 471.58

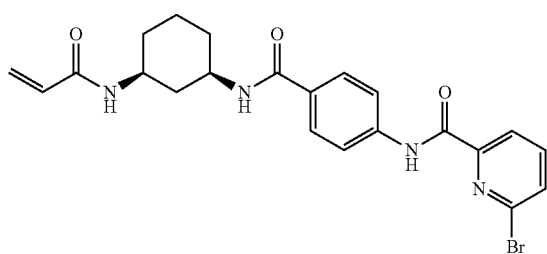 [SMILES: C=CC(=O)N[C@H]1CCC[C@@H](NC(=O)c2ccc(NC(=O)c3cccc(Br)n3)cc2)C1]

N-(4-(((1R,3S)-3-acrylamidocyclohexyl)carbamoyl)phenyl)-6-bromopicolinamide

Prepared using the same procedure as for the synthesis of N-(4-(4-acrylamidobenzamido)phenyl)-6-bromopicolinamide described above to give a brown solid that was used without further purification (91% yield). M/z expected: 471.36, observed: 471.64

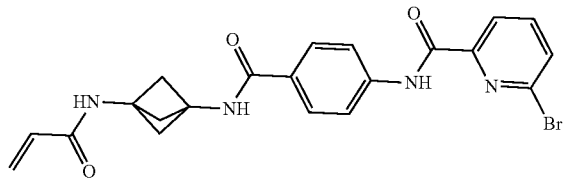 [SMILES: C=CC(=O)NC12CC(NC(=O)c3ccc(NC(=O)c4cccc(Br)n4)cc3)(C1)C2]

N-(4-((3-acrylamidobicyclo[1.1.1]pentan-1-yl)carbamoyl)phenyl)-6-bromopicolinamide Prepared using the same procedure as for the synthesis of N-(4-(4-acrylamidobenzamido)phenyl)-6-bromopicolinamide described above to give a brown solid that was used without further purification (91% yield). M/z expected: 455.31, observed: 455.73

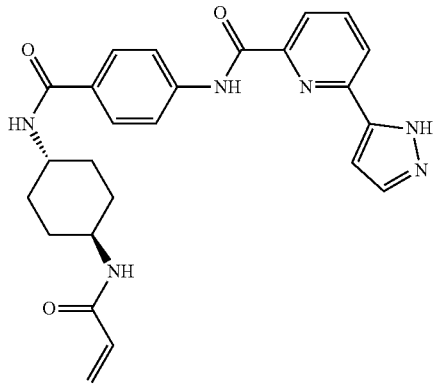 [SMILES: C=CC(=O)N[C@H]1CC[C@H](NC(=O)c2ccc(NC(=O)c3cccc(-c4ccn[nH]4)n3)cc2)CC1]

N-(4-(((1r,4r)-4-acrylamidocyclohexyl)carbamoyl)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (14% yield). M/z expected: 458.52, observed: 459.32. $^1$H NMR (500 MHz DMSO) δ 10.83, (Br, 1H), 8.20 (d, J=6 Hz, 1H), 8.12 (m, 2H), 8.03-7.90 (m, 4H), 7.68 (br, 1H), 7.09 (br, 1H), 6.21 (dd, J=10 Hz, 15 Hz, 1H), 6.16-6.08 (m, 1H), 5.57 (dd, J=3 Hz, 10 Hz, 1H), 3.83-3.56 (m, 2H), 1.88 (m, 4H), 1.51-1.26 (m, 6H). IRAK1 IC50=46 nM, IRAK4 IC50=154 nM.

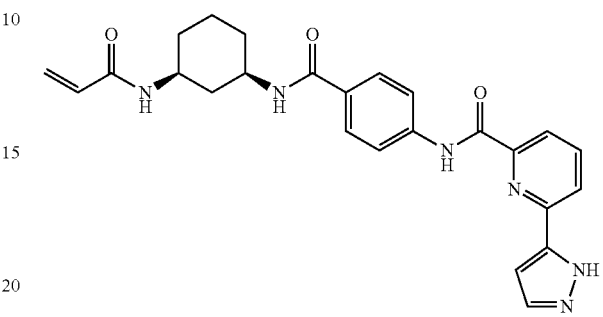

N-(4-(((1R,3S)-3-acrylamidocyclohexyl)carbamoyl)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (12% yield). M/z expected: 458.52, observed: 459.32. $^1$H NMR (500 MHz DMSO) δ 10.82, (Br, 1H), 8.25 (d, J=5 Hz, 1H), 8.17-8.03 (m, 3H), 7.99 (d, J=10 Hz, 2H), 7.92 (d, J=10 Hz, 2H), 7.71 (br, 1H), 7.12 (br, 1H), 6.20 (dd, J=10 Hz, 15 Hz, 1H), 6.16-6.08 (m, 1H), 5.57 (dd, J=3 Hz, 10 Hz, 1H), 3.93-3.66 (m, 2H), 1.86-1.74 (m, 3H), 1.46-1.09 (m, 6H). IRAK1 IC50=24 nM, IRAK4 IC50=648 nM.

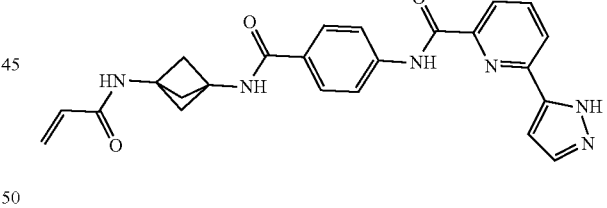

N-(4-((3-acrylamidobicyclo[1.1.1]pentan-1-yl)carbamoyl)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (12% yield). M/z expected: 442.48, observed: 443.29. $^1$H NMR (500 MHz DMSO) δ 10.77, (Br, 1H), 8.99 (s, 1H), 8.72 (s, 1H), 8.19-8.08 (m, 3H), 7.99 (d, J=10 Hz, 2H), 7.92 (d, J=10 Hz, 2H), 7.75 (br, 1H), 7.20 (br, 1H), 6.16 (dd, J=10 Hz, 15 Hz, 1H), 6.18-6.09 (m, 1H), 5.59 (dd, J=3 Hz, 10 Hz, 1H), 2.36 (s, 6H). IRAK1 IC50=51 nM, IRAK4 IC50=607 nM.

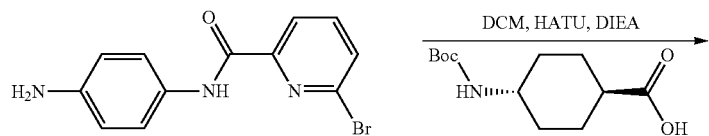
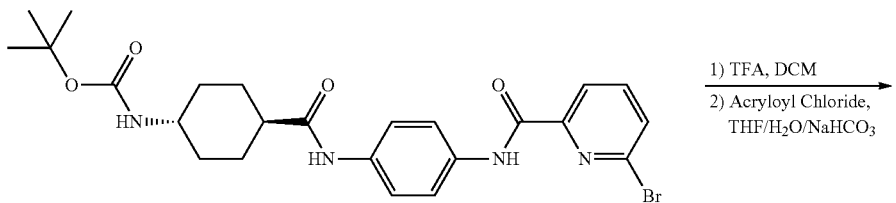
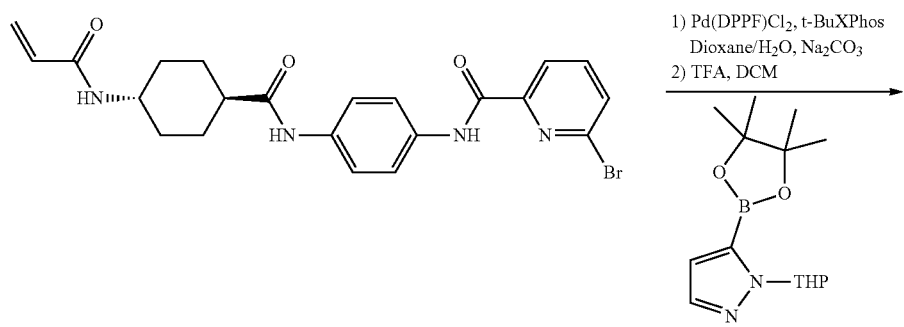
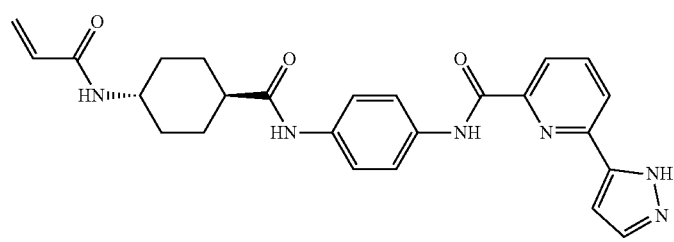
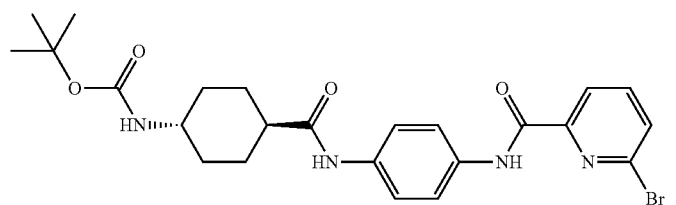

tert-butyl ((1r,4r)-4-((4-(6-bromopicolinamido)phenyl)carbamoyl)cyclohexyl)carbamate N-(4-aminophenyl)-6-bromopicolinamide (200 mg, 0.51 mmol) was dissolved in DCM (10 mL). (1r,4r)-4-((tert-butoxycarbonyl)amino)cyclohexane-1-carboxylic acid (136 mg, 0.561 mmol) and HATU (388 mg, 1.02 mmol) were added followed by DIEA (444 μL, 2.55 mmol). The mixture was stirred for 2 hours and the resulting precipitate was filtered and washed with DCM (5 mL) to give the desired product as a white solid (226 mg, 86% yield) that was used without further purification. M/z expected: 517.42, observed: 517.34

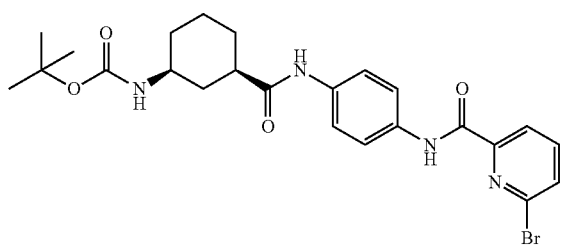 [SMILES: CC(C)(C)OC(=O)N[C@H]1CCC[C@@H](C(=O)Nc2ccc(NC(=O)c3cccc(Br)n3)cc2)C1]

tert-butyl ((1S,3R)-3-((4-(6-bromopicolinamido)phenyl)carbamoyl)cyclohexyl)carbamate Prepared using the same procedure as the above compound to give a white solid (218 mg, 83% yield) that was used without further purification. M/z expected: 517.42, observed: 517.56

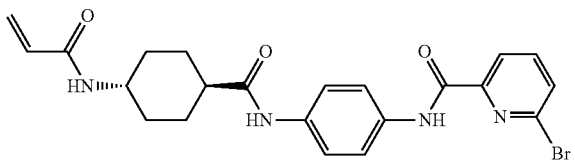 [SMILES: C=CC(=O)N[C@H]1CC[C@H](C(=O)Nc2ccc(NC(=O)c3cccc(Br)n3)cc2)CC1]

N-(4-((1r,4r)-4-acrylamidocyclohexane-1-carboxamido)phenyl)-6-bromopicolinamide

Prepared using the same procedure as for the synthesis of N-(4-(4-acrylamidobenzamido)phenyl)-6-bromopicolinamide described above to give a brown solid that was used without further purification (91% yield). M/z expected: 471.36, observed: 471.61

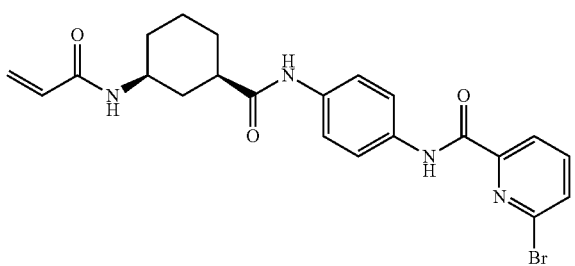 [SMILES: C=CC(=O)N[C@H]1CCC[C@@H](C(=O)Nc2ccc(NC(=O)c3cccc(Br)n3)cc2)C1]

N-(4-((1R,3S)-3-acrylamidocyclohexane-1-carboxamido)phenyl)-6-bromopicolinamide

Prepared using the same procedure as for the synthesis of N-(4-(4-acrylamidobenzamido)phenyl)-6-bromopicolinamide described above to give a brown solid that was used without further purification (91% yield). M/z expected: 471.36, observed: 471.43

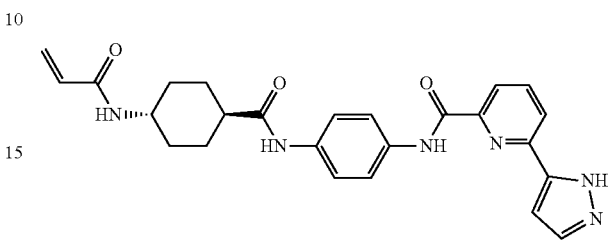

N-(4-((1r,4r)-4-acrylamidocyclohexane-1-carboxamido)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (8% yield). M/z expected: 458.52, observed: 459.71. $^1$H NMR (500 MHz DMSO) δ 10.64, (Br, 1H), 9.88 (s, 1H), 8.15-8.05 (m, 3H), 7.99 (d, J=10 Hz, 2H), 7.79 (d, J=10 Hz, 2H), 7.65 (d, J=10 Hz, 2H), 6.20 (dd, J=10 Hz, 15 Hz, 1H), 6.12-6.03 (m, 1H), 5.57 (dd, J=3 Hz, 10 Hz, 1H), 3.60 (m, 2H), 2.30 (m, 1H), 1.90 (m, 4H), 1.53 (m, 2H), 1.26 (m, 2H). IRAK1 IC50=88 nM, IRAK4 IC50=1,110 nM.

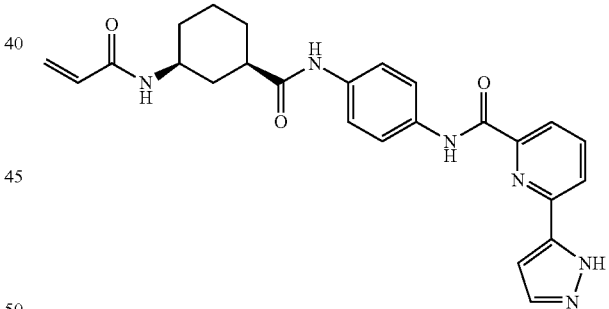

N-(4-((1R,3S)-3-acrylamidocyclohexane-1-carboxamido)phenyl)-6-(1H-pyrazol-5-yl)picolinamide Prepared using the same procedure as for the synthesis of N-(4-(4-acrylamidobenzamido)phenyl)-6-(1H-pyrazol-5-yl)picolinamide described above to give a brown oil that was purified by reverse phase HPLC using a gradient of 1 to 70% ACN in H$_2$O to give the desired product as a white solid (8% yield). M/z expected: 458.52, observed: 459.62. $^1$H NMR (500 MHz DMSO) δ 10.62, (Br, 1H), 9.93 (s, 1H), 8.14-8.04 (m, 4H), 7.78 (d, J=10 Hz, 2H), 7.73 (s, 1H), 7.67 (d, J=10 Hz, 2H), 7.18 (br, 1H), 6.20 (dd, J=10 Hz, 15 Hz, 1H), 6.12-6.03 (m, 1H), 5.57 (dd, J=3 Hz, 10 Hz, 1H), 3.81-3.67 (m, 2H), 1.98-1.77 (m, 4H), 1.42-1.32 (m, 3H), 1.15 (m, 1H). IRAK1 IC50=72 nM, IRAK4 IC50>10,000 nM.

Other compounds prepared using the same procedure as for the synthesis of N-(4-(4-acrylamidobenzamido)phenyl)-6-(1H-pyrazol-5-yl)picolinamide described above.

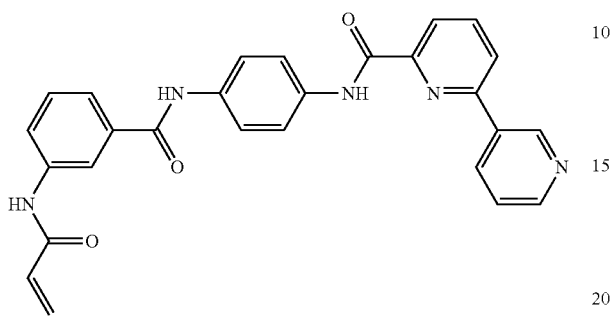

N-(4-(4-acrylamidobenzamido)phenyl)-[2,3'-bipyridine]-6-carboxamide

Brown solid (33% yield). M/z expected: 463.50, observed: 463.72. $^1$H NMR (500 MHz DMSO) δ 10.61, (s, 1H), 10.38 (s, 1H), 10.32 (s, 1H), 9.70 (s, 1H), 9.0 (d, J=5 Hz, 1H), 8.81 (s, 1H), 8.39 (d, J=9 Hz, 2H), 8.26-8.18 (m, 3H), 7.94-7.77 (m, 5H), 7.68 (d, J=6 Hz, 1H), 7.49 (t, J=10 Hz, 1H), 6.47 (dd, J=10 Hz, 15 Hz, 1H), 6.38-6.27 (m, 1H), 5.80 (dd, J=3 Hz, 10 Hz, 1H). IRAK1 IC50=80 nM, IRAK4 IC50>10,000 nM.

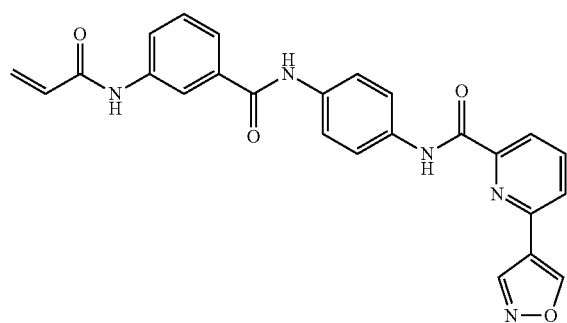 [SMILES: C=CC(=O)Nc1cccc(C(=O)Nc2ccc(NC(=O)c3cccc(-c4cnoc4)n3)cc2)c1]

N-(4-(3-acrylamidobenzamido)phenyl)-6-(isoxazol-4-yl)picolinamide

Yellow solid (10% yield). M/z expected: 453.46, observed: 453.38. $^1$H NMR (500 MHz DMSO) δ 10.82, (s, 1H), 10.37 (s, 1H), 10.31 (s, 1H), 9.03 (d, J=5 Hz, 1H), 8.17 (s, 1H), 8.01 (t, J=10 Hz, 1H), 7.94-7.11 (m, 2H), 7.84-7.75 (m, 4H), 7.67 (d, J=9 Hz, 1H), 7.55 (d, J=9 Hz, 1H), 7.50 (t, J=10 Hz, 1H), 6.54 (br, 1H), 6.47 (dd, J=10 Hz, 15 Hz, 1H), 6.38-6.27 (m, 1H), 5.79 (dd, J=3 Hz, 10 Hz, 1H). IRAK1 IC50=12 nM, IRAK4 IC50>10,000 nM.

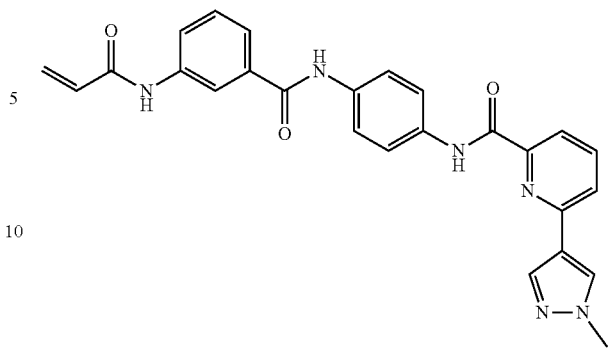

N-(4-(3-acrylamidobenzamido)phenyl)-6-(1-methyl-1H-pyrazol-4-yl)picolinamide

Brown solid (33% yield). M/z expected: 466.50, observed: 466.41. $^1$H NMR (500 MHz DMSO) δ 10.45, (s, 1H), 10.37 (s, 1H), 10.31 (s, 1H), 8.65, (s, 1H), 8.34 (s, 1H), 8.18 (s, 1H), 8.01 (t, J=10 Hz, 1H), 7.95-7.87 (m, 5H), 7.81 (d, J=9 Hz, 2H), 7.68 (d, J=7 Hz, 1H), 7.49 (t, J=10 Hz, 1H), 6.47 (dd, J=10 Hz, 15 Hz, 1H), 6.38-6.27 (m, 1H), 5.80 (dd, J=3 Hz, 10 Hz, 1H), 3.93 (s, 3H). IRAK1 IC50=67 nM, IRAK4 IC50>10,000 nM.

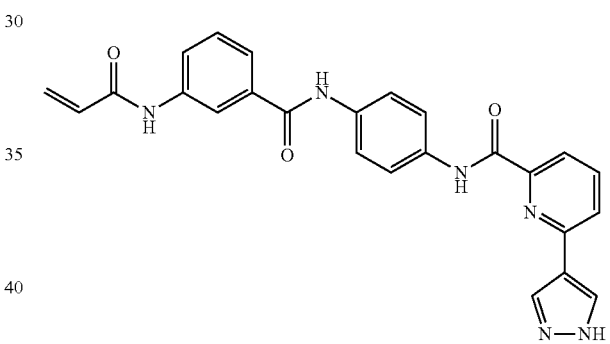

N-(4-(3-acrylamidobenzamido)phenyl)-6-(1H-pyrazol-4-yl)picolinamide

Brown solid (28% yield). M/z expected: 452.47, observed: 452.75. $^1$H NMR (500 MHz DMSO) δ 10.47, (s, 1H), 10.37 (s, 1H), 10.31 (s, 1H), 8.56, (s, 1H), 8.18 (s, 1H), 8.04-7.87 (m, 6H), 7.80 (d, J=9 Hz, 2H), 7.69 (d, J=7 Hz, 2H), 7.50 (t, J=10 Hz, 1H), 6.47 (dd, J=10 Hz, 15 Hz, 1H), 6.38-6.27 (m, 1H), 5.79 (dd, J=3 Hz, 10 Hz, 1H). IRAK1 IC50=22 nM, IRAK4 IC50>10,000 nM.

Biological Assays

Figure 1B:
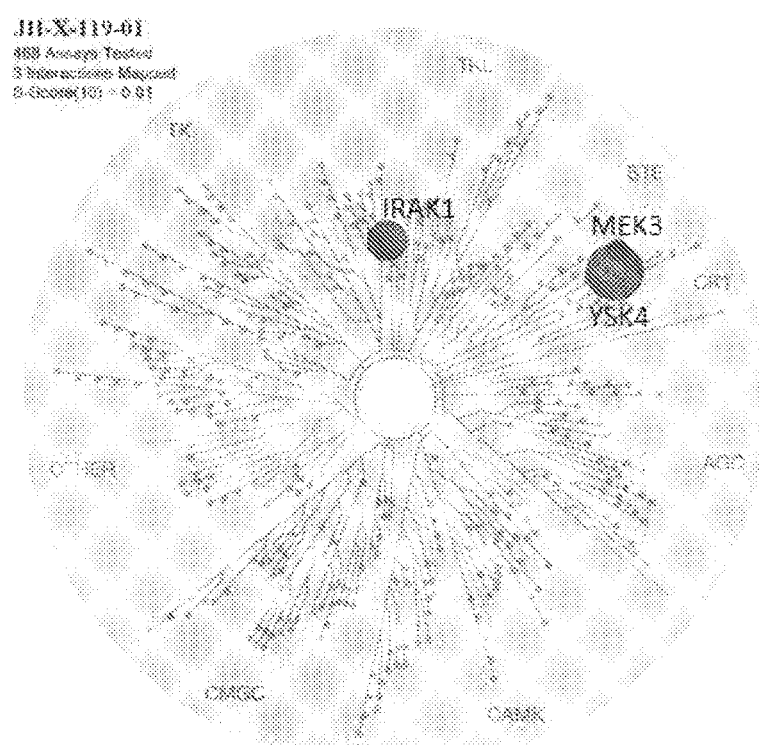
Figure 2:
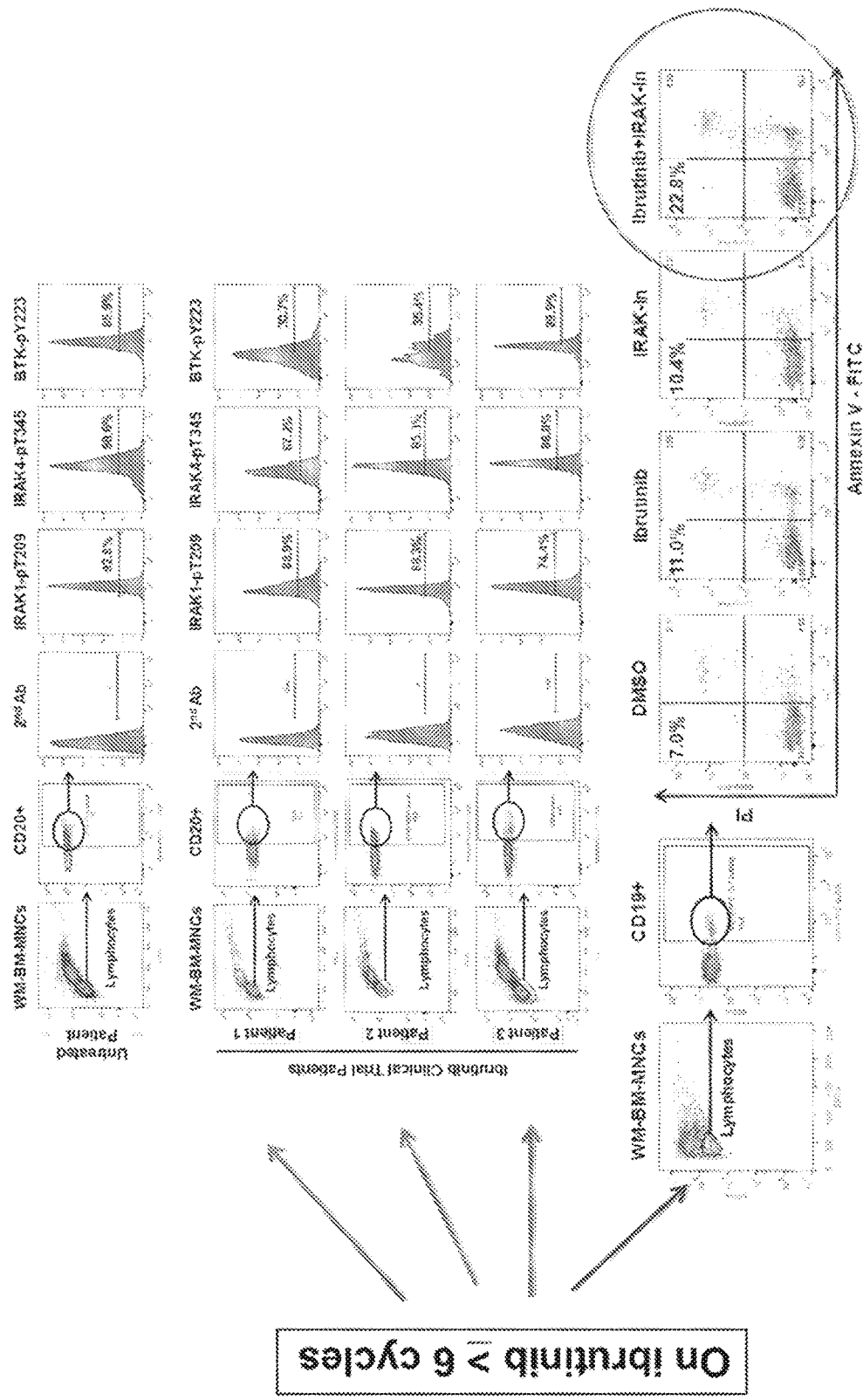
FIG. 2. IRAK1/4 kinase survival signaling remains intact in WM cells from ibrutinib treated patients.
Figure 3:
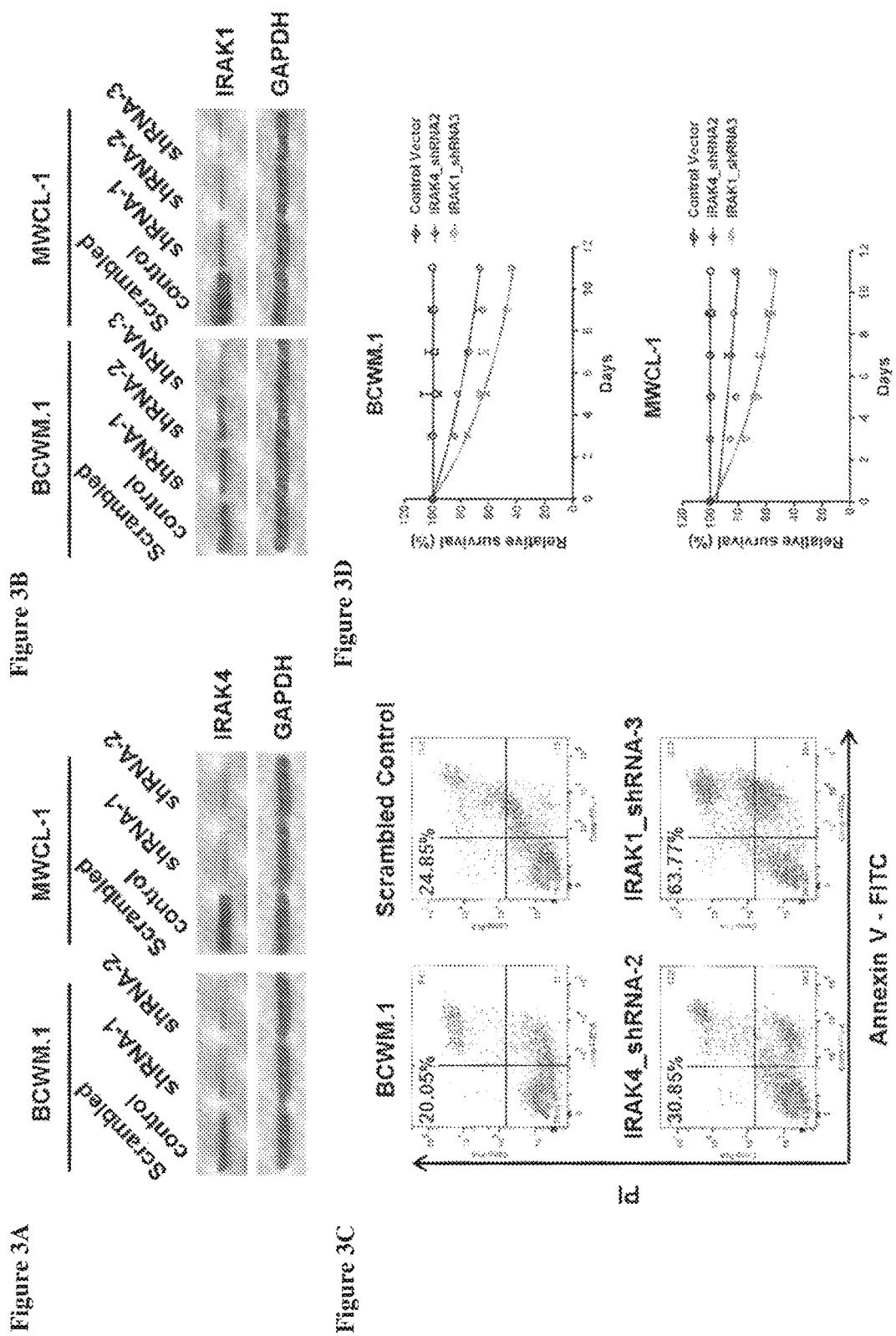
FIGS. 3A to 3D. Cell survival is more dependent on IRAK1 over IRAK4 in MYD88 mutated WM cells.
Figure 5:
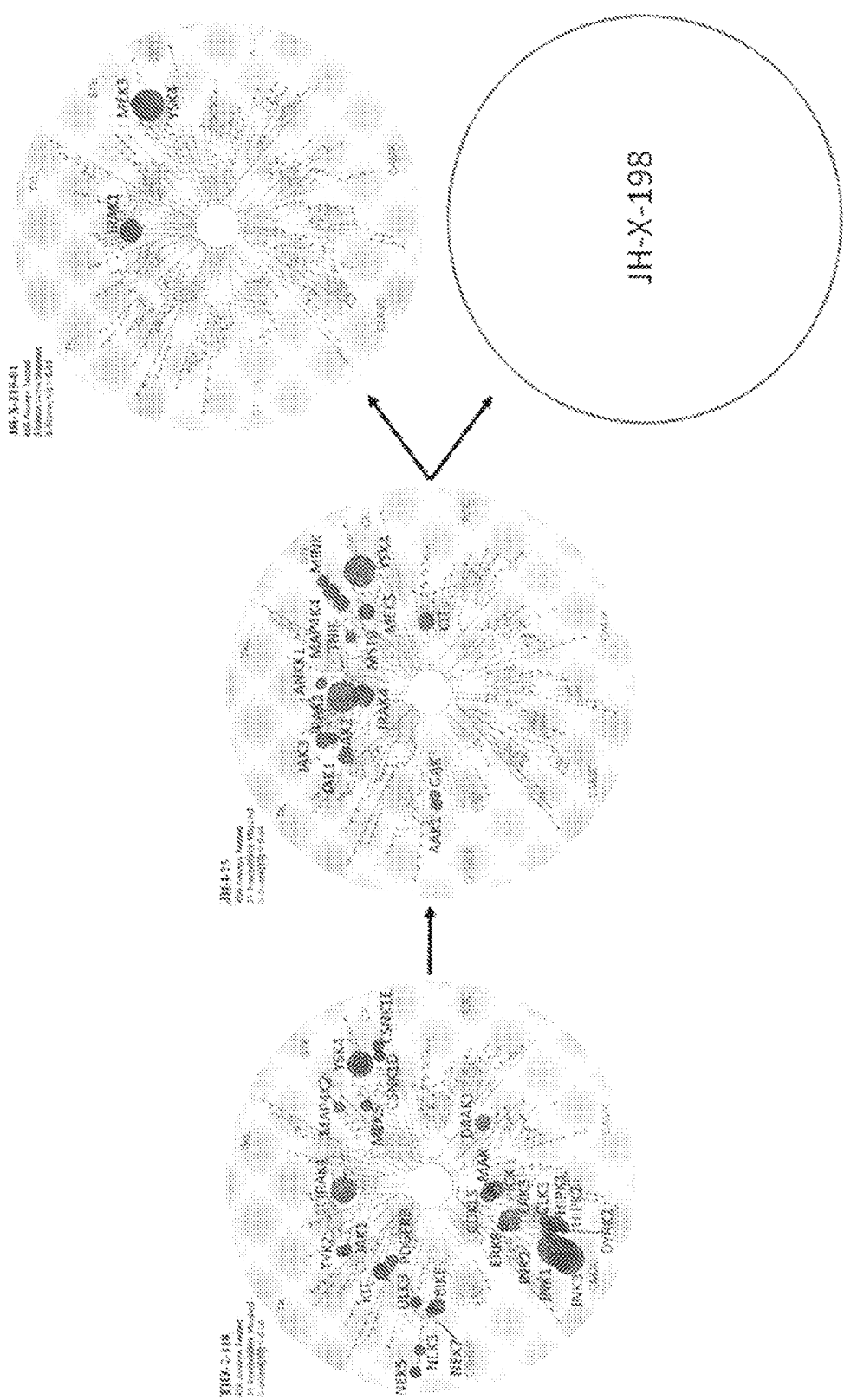
FIG. 5. Kinome tree for IRAK1 inhibitors.
Figure 6:
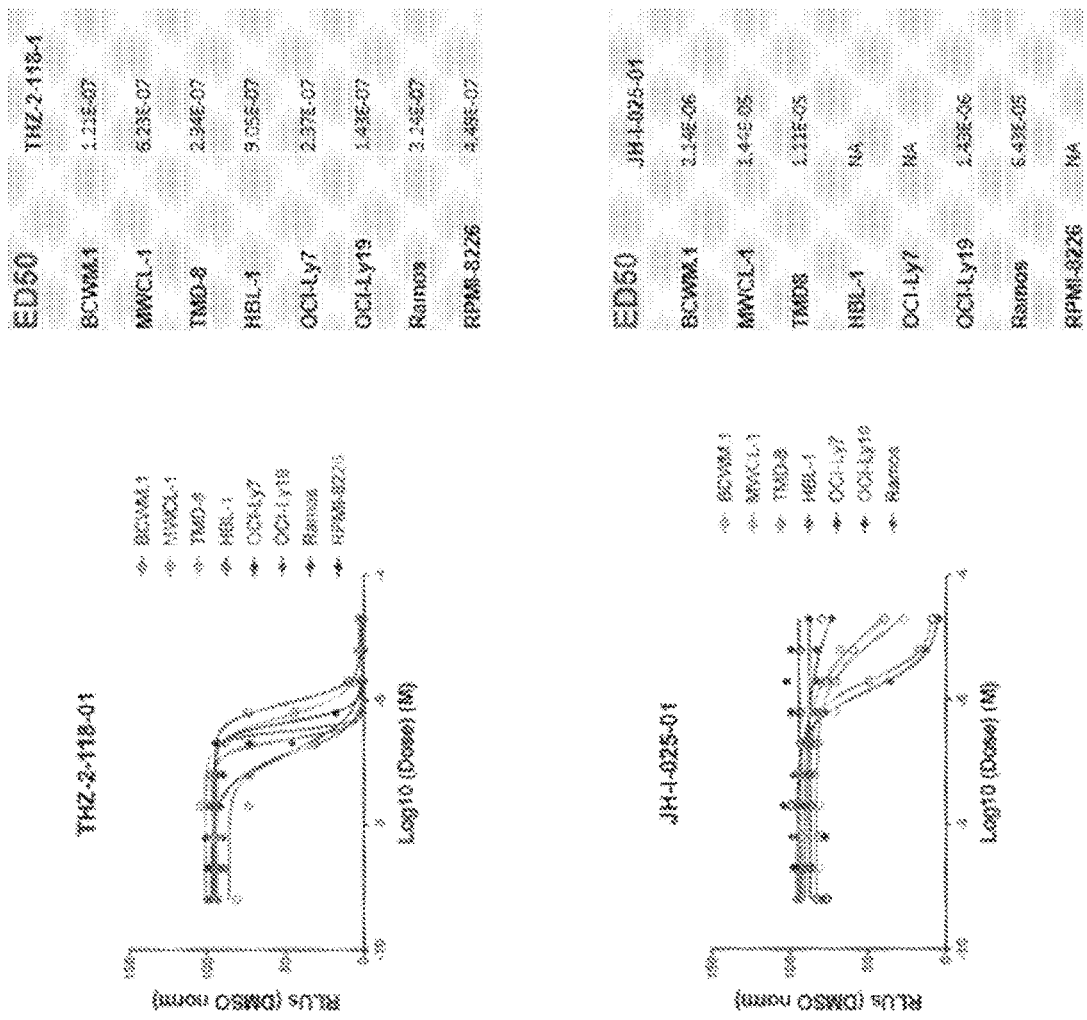
FIG. 6. Cellular data for covalent IRAK1 inhibitors.
Figure 7:
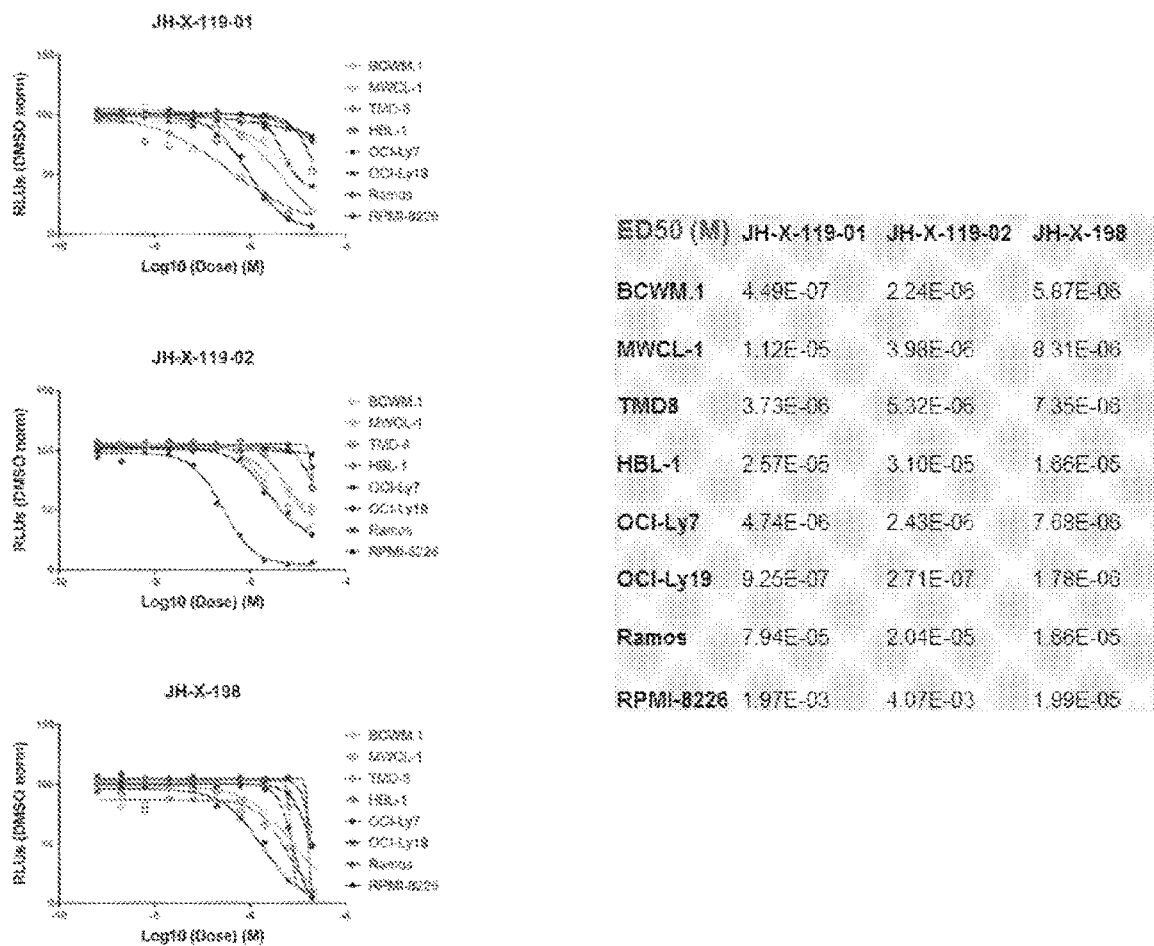
FIG. 7. Cellular data for covalent IRAK1 inhibitors. JH-X-119-01 showed cell killing with micromolar ED50's when tested in Waldenstrom's, DLBCL, and Burkitt Lymphoma cell lines.
Figure 8:
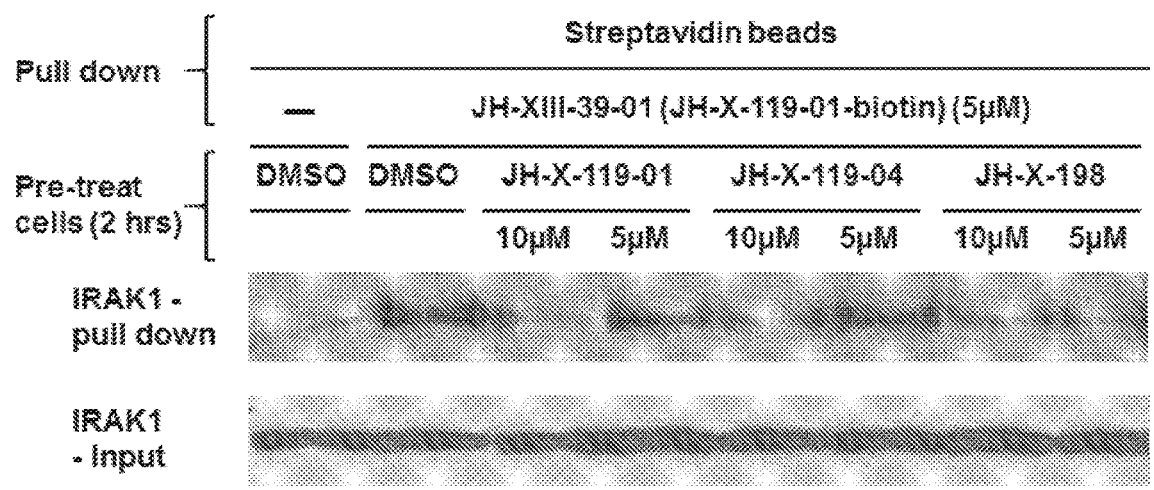
FIG. 8. IRAK1 inhibitor JH-X-119-01 target engagement in BCWM.1 cells.
Figure 9:
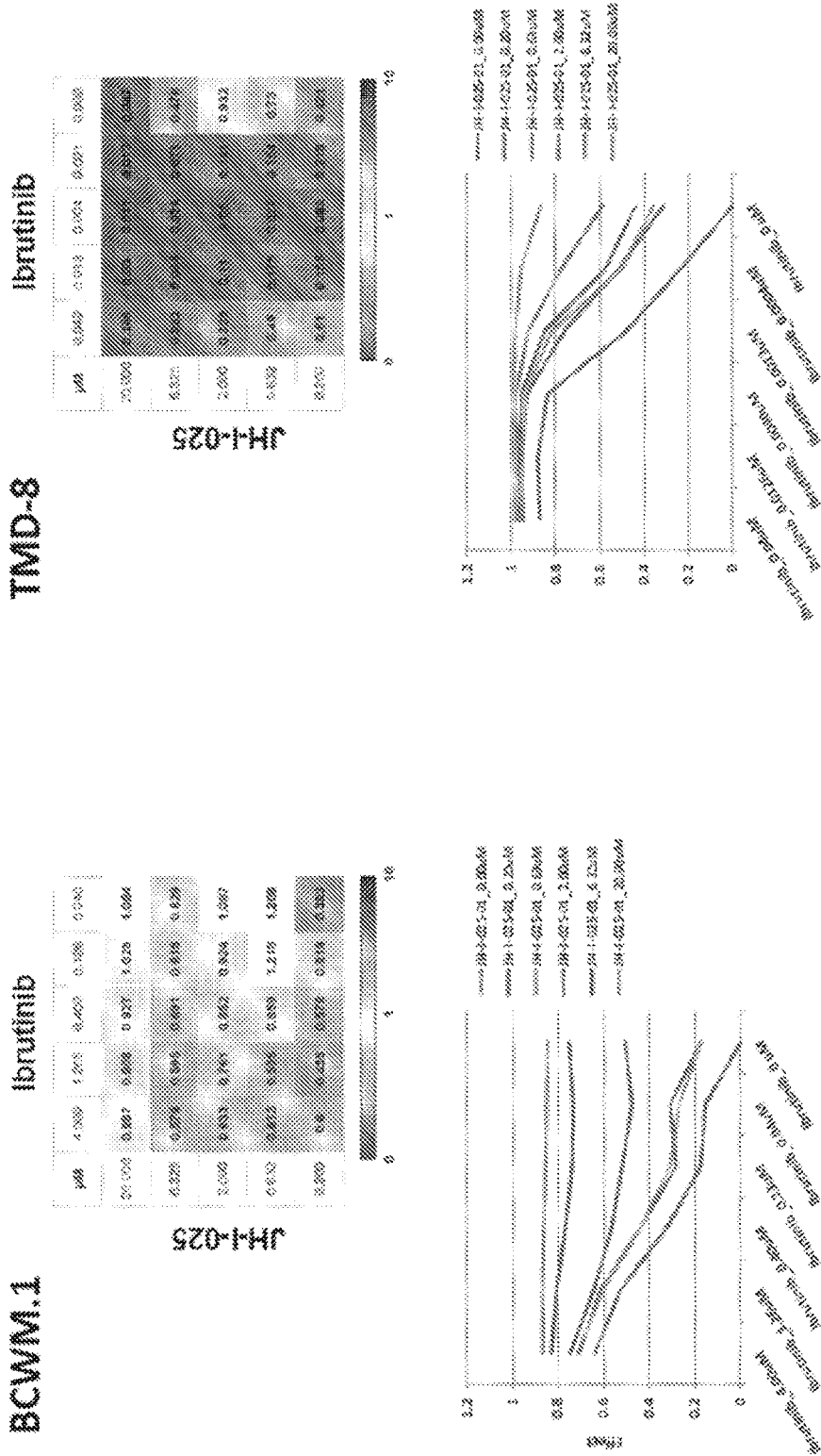
FIG. 9. Synergism evaluation for Ibrutinib and compound JH-I-025. Combination Index (CI<1.0).
Figure 10:
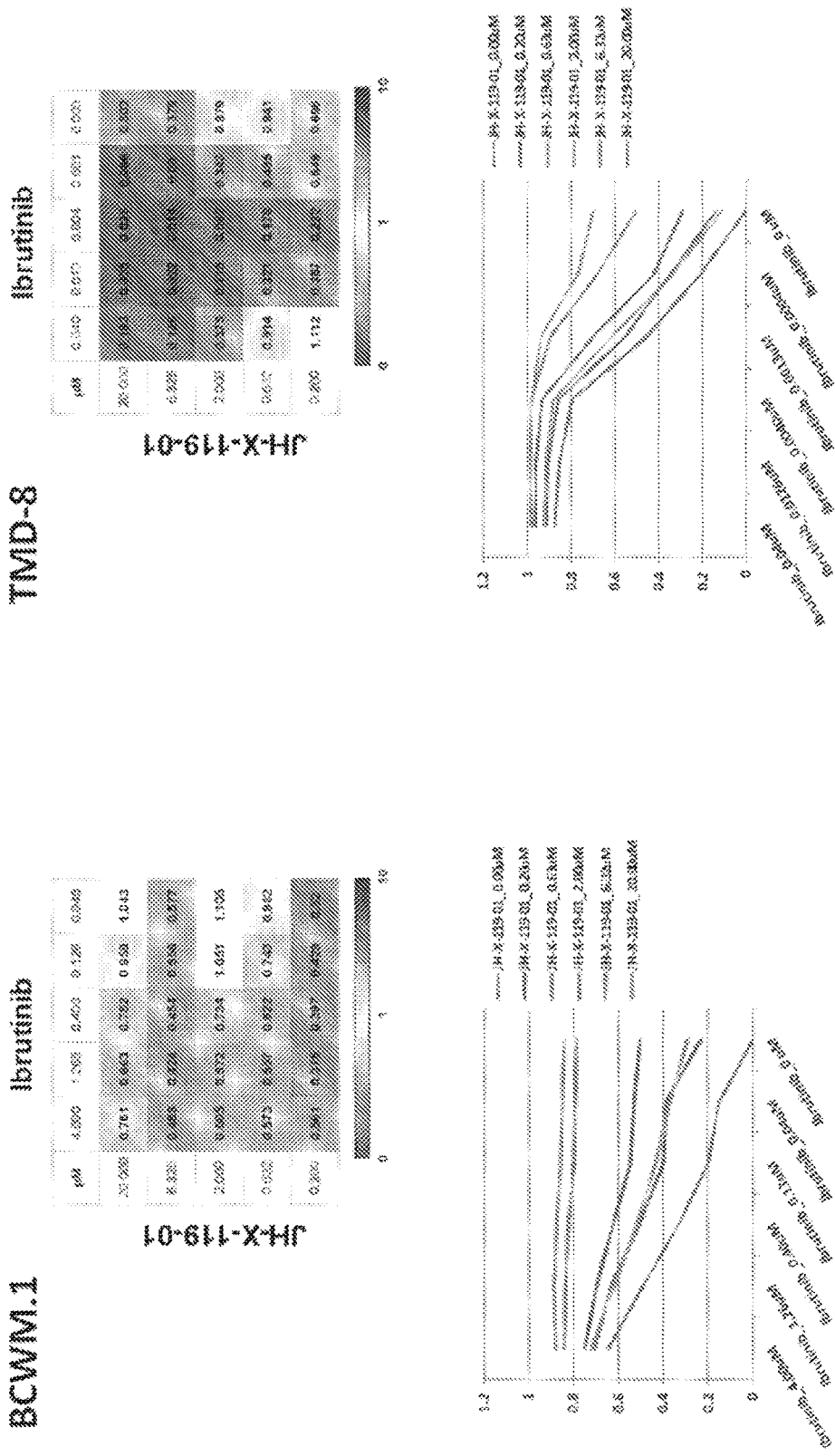
FIG. 10. Synergism evaluation for Ibrutinib and compound JH-X-119-01. Combination Index (CI<1.0).
Figure 11:
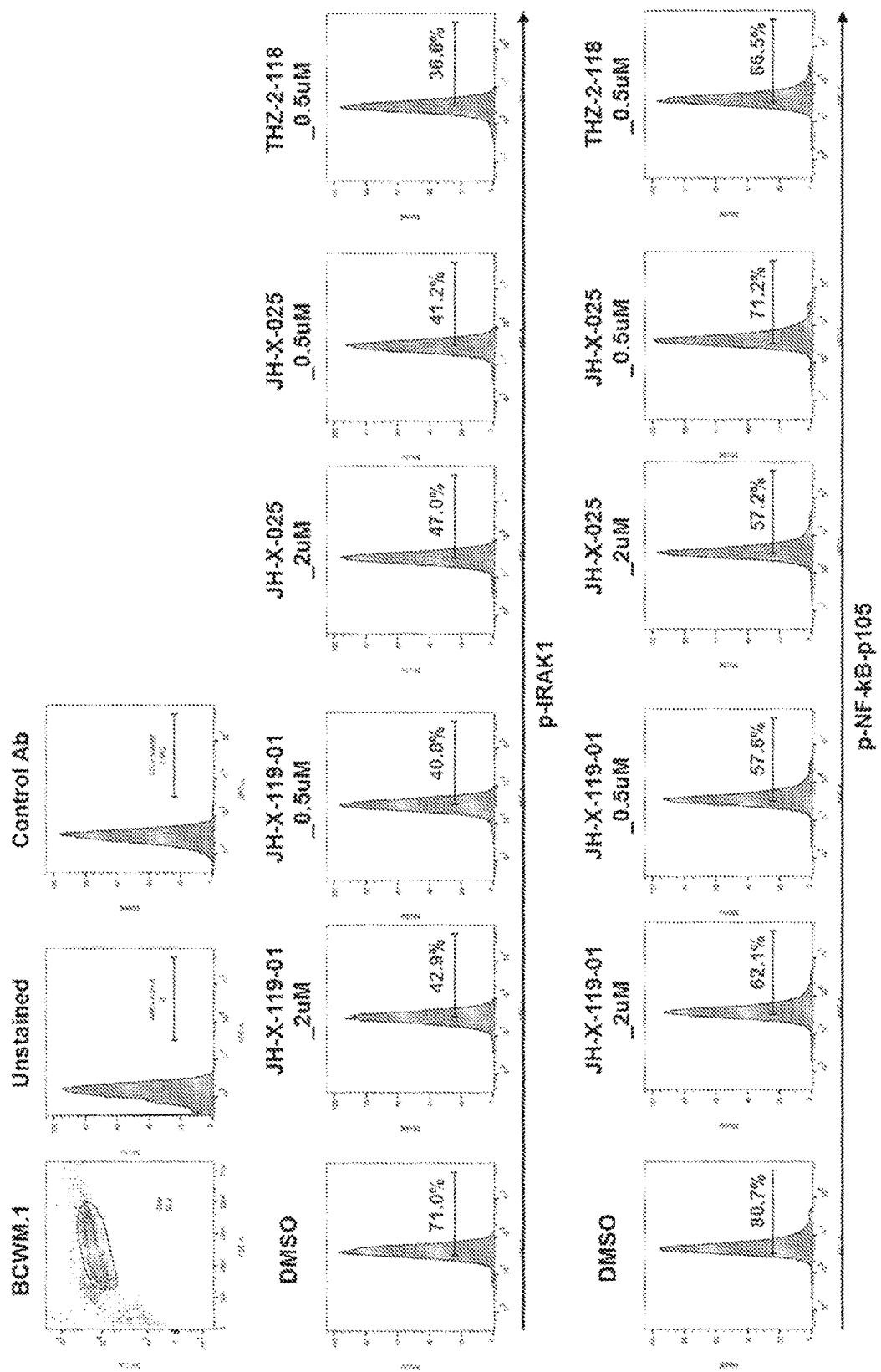
FIG. 11. IRAK1 inhibitors reduce IRAK1 and downstream NF-kB-p105 phosphorylation in MYD88 mutated WM cells. Following recruitment on the activated receptor complex, phosphorylated on Thr-209, probably by IRAK4, resulting in a conformational change of the kinase domain, allowing further phosphorylations to take place. Thr-387 phosphorylation in the activation loop is required to achieve full enzymatic activity. Kollewe C, J. Biol. Chem. 279:5227-5236 (2004).
Figure 12:
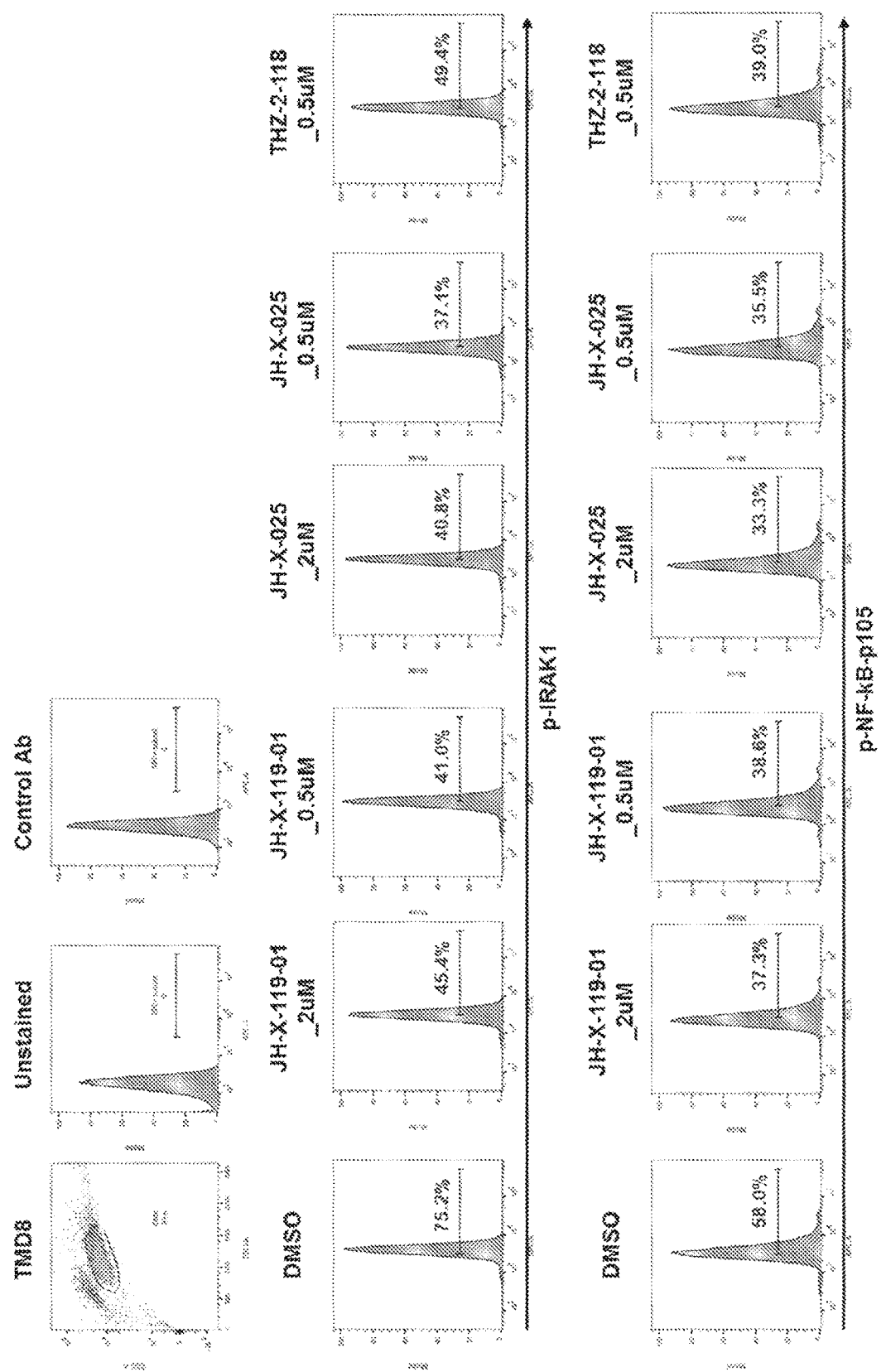
FIG. 12. IRAK1 inhibitors reduce IRAK1 and downstream NF-kB-p105 phosphorylation in MYD88 mutated ABC-DLBCL cells.
Figure 13:
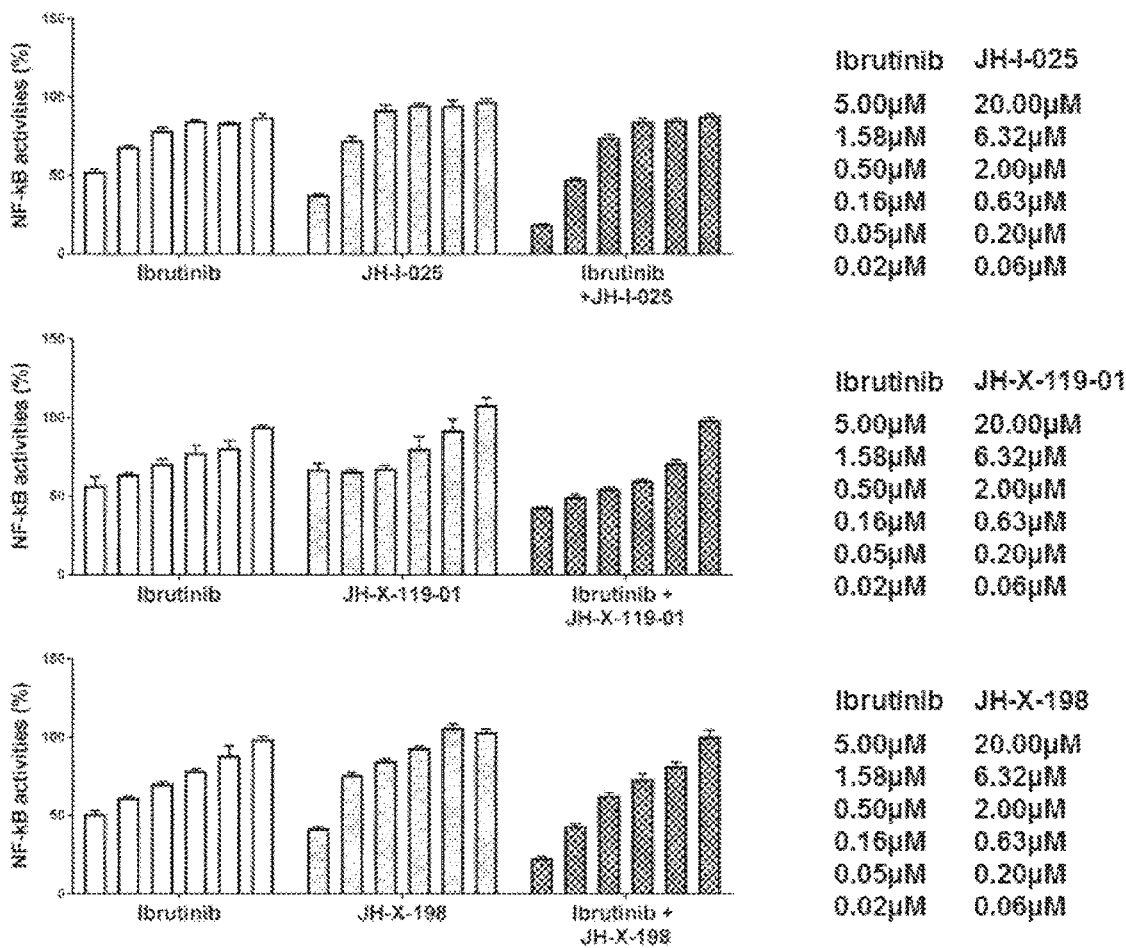
FIG. 13. The combination of IRAK1 inhibitors with BTK inhibitor, Ibrutinib shows more robust inhibition of NF-kB activity in a NF-kB promoter driven Luciferase reporter assay.
Figure 14:
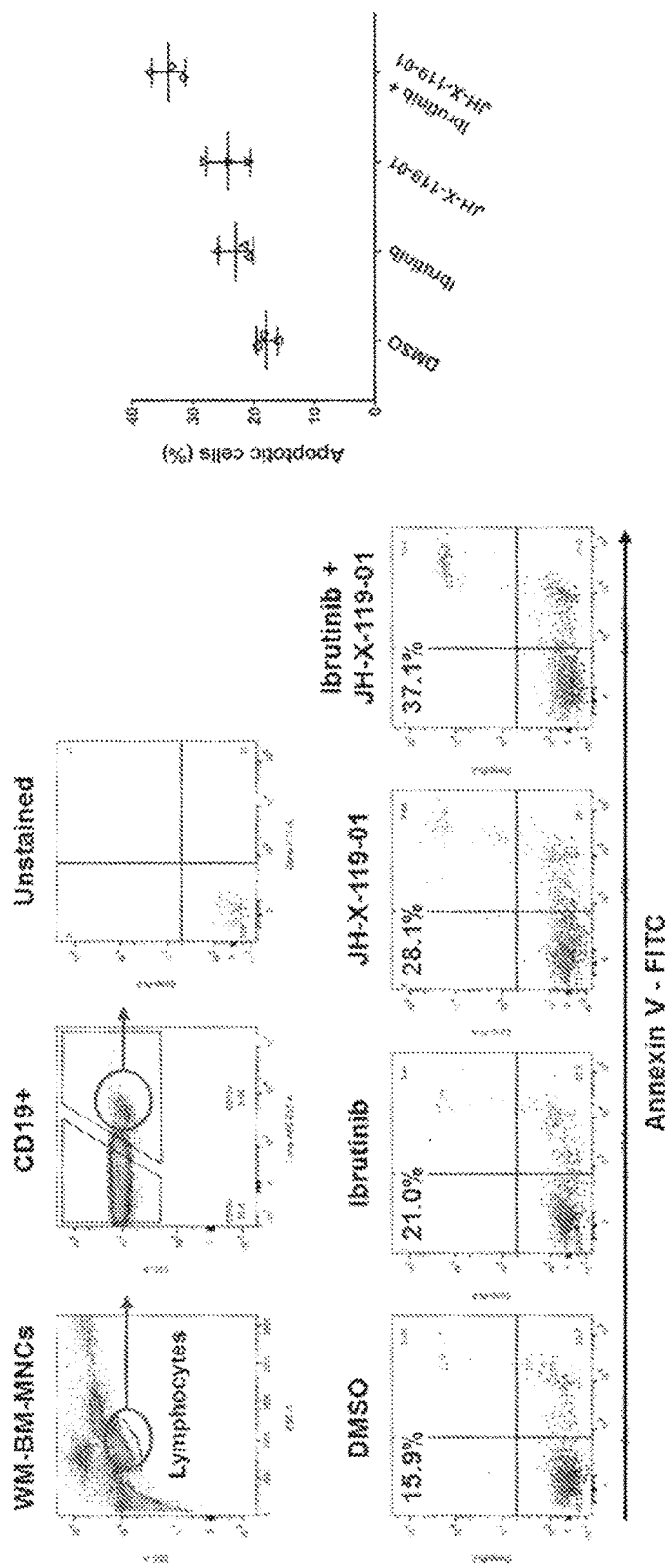
FIG. 14. The combination of IRAK1 inhibitor, JH-X-119-01 with BTK inhibitor, and Ibrutinib shows more robust tumor cells killing in WM patients' bone marrow LPCs.
Figure 15:
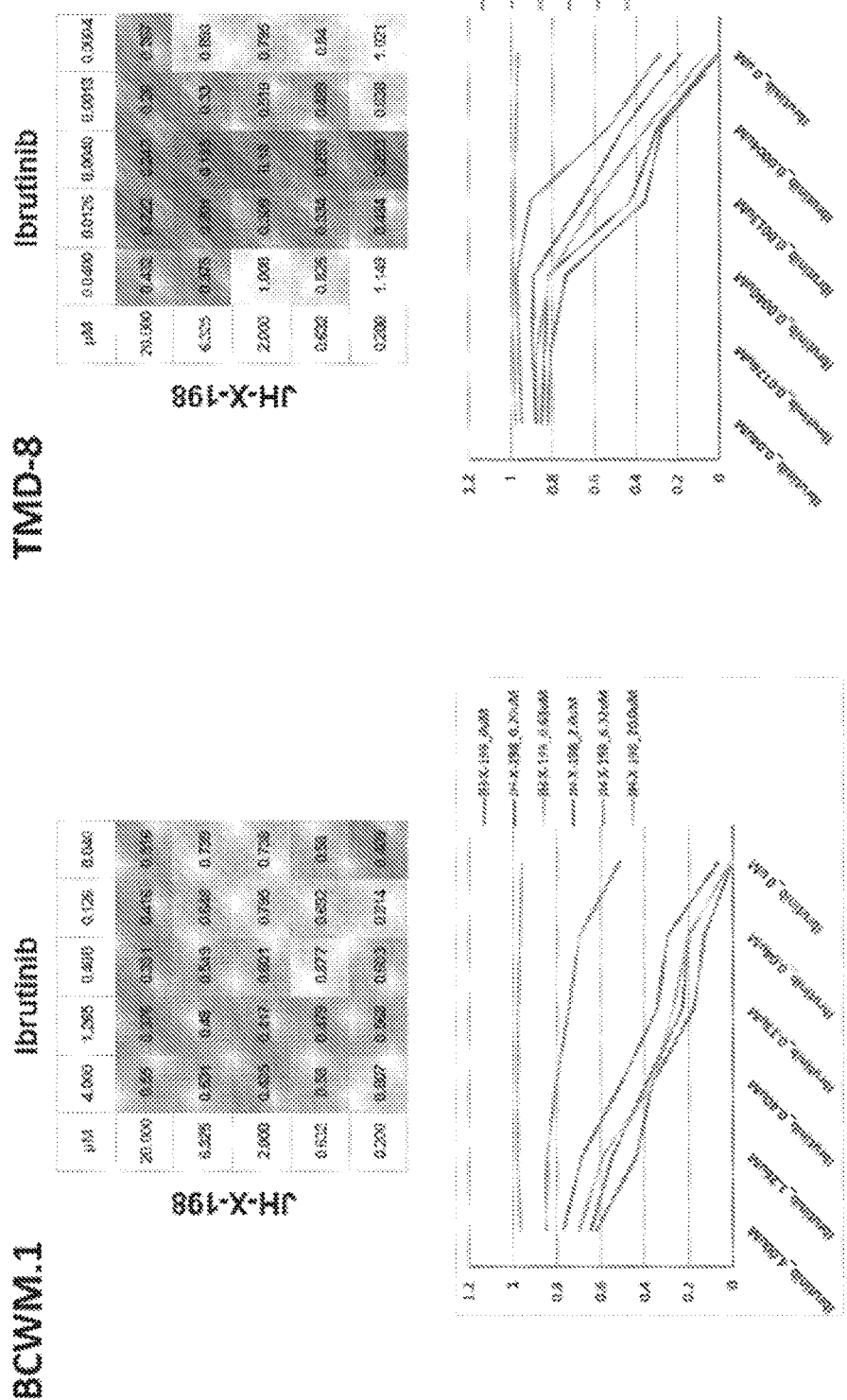
FIG. 15. Synergism evaluation for Ibrutinib and compound JH-X-198. Combination Index (CI<1.0).

A novel, highly selective IRAK1 inhibitor Jh-X-119-01 shows synergistic tumor cell killing with Ibrutinib in MYD88. Activating mutations in MYD88 are present in many B-cell lymphoproliferative disorders including WM (95%), ABC DLBCL (39%), Primary CNS Lymphoma (80-90%), Marginal Zone Lymphoma (6-10%) and Chronic Lymphocytic Leukemia (4-8%). In MYD88 mutated WM and ABC DLBCL cells, MYD88 triggers NF-kB pro-growth and survival signaling through divergent pathways driven by BTK and IRAK4/IRAK1 (Ngo et al, Nature 2011; Yang et al, Blood 2013). Ibrutinib targets BTK, and has shown high levels of activity in MYD88 mutated WM, ABC DLBCL and PCNSL. Responses however are partial, and complete remissions are lacking. It was therefore sought to be clarified if persistent IRAK4/IRAK1 signaling was responsible for survival of malignant lymphoplasmacytic cells (LPC) in WM patients on ibrutinib. It was observed by flow cytometric analysis that while BTK activation was suppressed in WM patients on ibrutinib for >6 months, both IRAK4 and IRAK1 remained hyperactivated. Treatment of LPC from patients on ibrutinib with a toolbox IRAK4/IRAK1 inhibitor resulted in marked reduction of NF-kB and induction of apoptosis. Subsequently, lentiviral transduction studies were performed in MYD88 mutated BCWM.1 cells, and it was observed in an inducible model system that knockdown of IRAK1 produced more robust apoptotic effects versus IRAK4 (FIGS. 1A and 3C). Given these findings, a medical chemistry campaign has been pursued to develop a potent and highly selective inhibitor of IRAK1 kinase activity, JH-X-119-01. JH-X-119-01 inhibited IRAK1 biochemically with an IC50 of 9.3 nM while exhibiting no inhibition of IRAK4 at concentrations up to 10 µM, and showed exceptional kinome selectivity with off-target inhibition of only two kinases, YSK4 and MEK3 (FIGS. 1B and 5). Mass spec labelling studies were used to confirm that JH-X-119-01 irreversibly labelled IRAK1 at cysteine 302. JH-X-119-01 showed antiproliferative effects on MYD88 mutated WM and ABC DLBCL cells. Importantly, the combination of JH-X-119-01 with Ibrutinib led to synergistic tumor cell killing in MYD88 mutated WM and ABC-DLBCL cells, and suppression of NF-KB activation (FIGS. 1C and 9). In vivo PK studies revealed a favorable profile for JH-X-119-01 with a moderate half-life of 1.61 hours, a Cmax of 9.95 µM, and a low clearance of 18.84 mL/min/kg when dosed IV. The present findings evidence the development of a novel, highly selective IRAK1 kinase inhibitor, JH-X-119-01, that shows specific inhibition of IRAK1 kinase activity and a reduction of tumor cell survival in MYD88 mutated WM. Importantly, JH-X-119-01 shows synergistic tumor cell killing with ibrutinib in MYD88 mutated WM and ABC-DLBCL cells. This study provides a framework for the development of highly selective IRAK1 inhibitors for use alone, and in combination with ibrutinib in MYD88 mutated B-cell lymphomas.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I'):

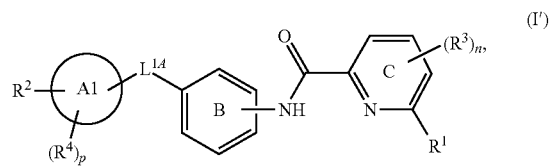

or a pharmaceutically acceptable salt, solvate, hydrate, tautomer, or stereoisomer thereof, wherein:
R[1] is an optionally substituted monocyclic heteroaryl ring;
R[2] is a warhead of formula:
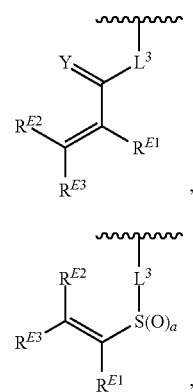 (i-1)
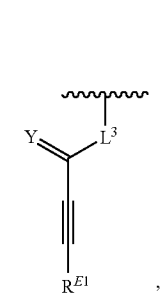 (i-2)
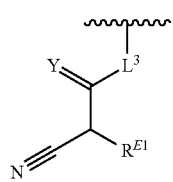 (i-3)
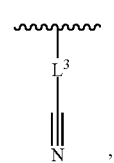 (i-4)
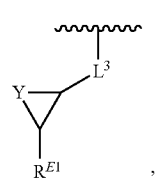 (i-5)
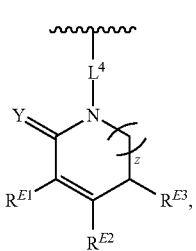 (i-6)
(i-7)
-continued
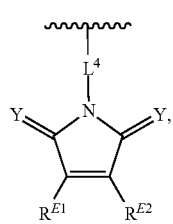 (i-8)
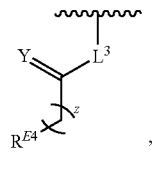 (i-9)
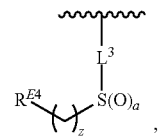 (i-10)
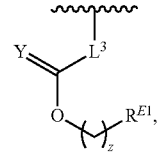 (i-11)
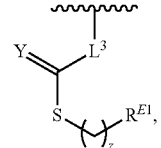 (i-12)
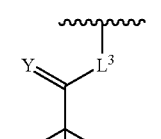 (i-13)
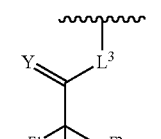 (i-14)
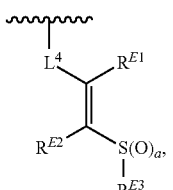 (i-15)
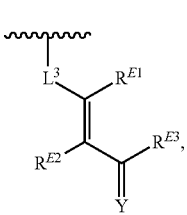 (i-16)

-continued
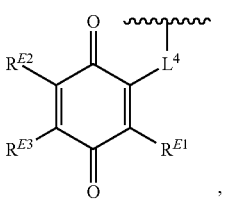
(i-17)
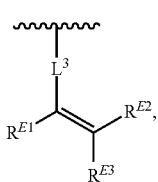
(i-18)
(i-19)
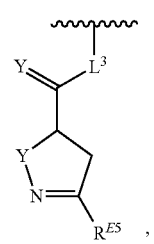
(i-20)
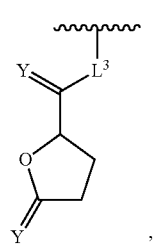
(i-21)
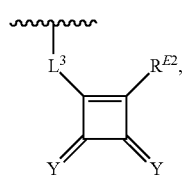
(i-22)
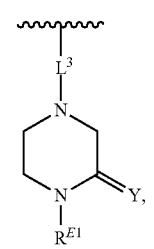
(i-23)
-continued
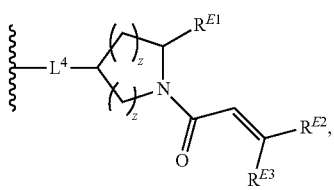
(i-24)
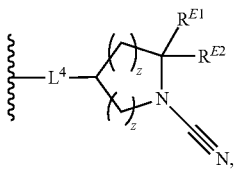
(i-25)
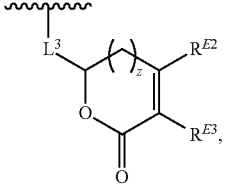
(i-26)
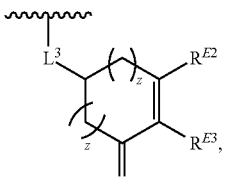
(i-27)
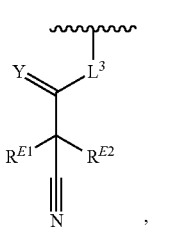
(i-28)
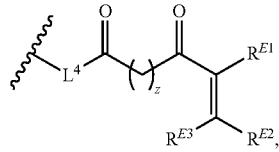
(i-29)
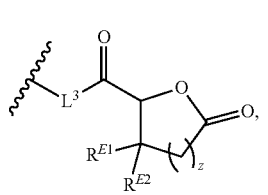
(i-30)
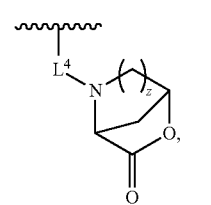
(i-31)

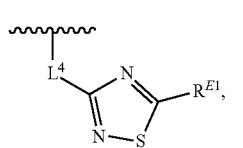 (i-32)

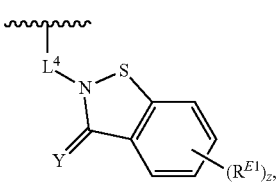 (i-33)

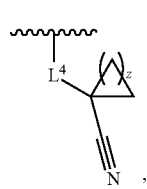 (i-34)

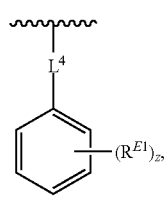 (i-35)

(i-36)
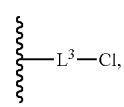 —L³—Cl, (i-37)
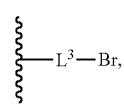 —L³—Br, (i-38)
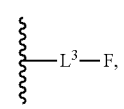 —L³—F, (i-39)
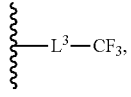 —L³—CF₃, (i-40)
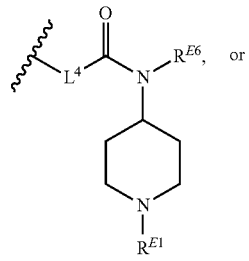 or

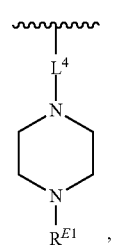 (i-41)

wherein:

L³ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)₂—, —S(=O)₂O—, —OS(=O)₂—, —S(=O)₂NR$^{L3a}$—, or —NR$^{L3a}$S(=O)₂—, wherein each occurrence of R$^{L3}$a is independently hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$_{L3b}$ groups are joined to form an optionally substituted carbocyclic or optionally substituted heterocyclic ring;

L⁴ is a bond or an optionally substituted branched or unbranched $C_{1-6}$ hydrocarbon chain;

each occurrence of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{EE}$, —CH₂N(R$^{EE}$)₂, —CH₂SR$^{EE}$, —OR$^{EE}$, —N(R$^{EE}$)₂, —Si(R$^{EE}$)₃, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits;

$L^{1A}$ is $^{1a}$—NR$^{L1}$C(=O)—$^{1b}$, $^{1a}$—C(=O)NR$^{L1}$—$^{1b}$, or an unsubstituted 5-membered heteroaryl ring; wherein $^{1a}$ indicates the point of attachment is to Ring A1; and $^{1b}$ indicates the point of attachment is to Ring B;

each instance of R$^3$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein each instance of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of R$^{D1a}$ are taken together with their intervening atoms to form a substituted or unsubstituted heterocyclic or substituted or unsubstituted heteroaryl ring;

or two R$^3$ groups are joined to form an optionally substituted carbocyclyl, optionally substituted heterocyclyl, optionally substituted aryl, or optionally substituted heteroaryl ring;

each instance of R$^4$, if present, is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$;

R$^{L1}$ is independently hydrogen, optionally substituted C$_{1-6}$ alkyl, or a nitrogen protecting group;

Ring A1 is optionally substituted carbocyclyl, optionally substituted phenyl, optionally substituted 5-membered heterocyclyl, or optionally substituted 6-membered heterocyclyl;

n is 0, 1, 2, or 3; and p is 0, 1, 2, 3, or 4.

2. The compound of claim 1, wherein the compound is of Formula (I):

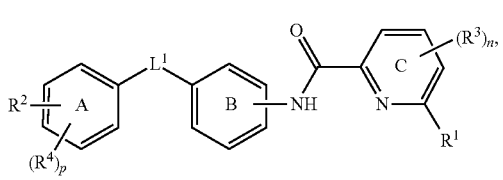

or a pharmaceutically acceptable salt, solvate, hydrate, tautomer, or stereoisomer thereof, wherein:

L$^1$ is $^{1a}$—NR$^{L1}$C(=O)—$^{1b}$ or an unsubstituted 5-membered heteroaryl ring; wherein $^{1a}$ indicates the point of attachment is to Ring A; and $^{1b}$ indicates the point of attachment is to Ring B.

3. The compound of claim 1, or a pharmaceutically acceptable salt, solvate, hydrate, tautomer, or stereoisomer thereof, wherein Ring A1 is optionally substituted cyclohexyl, optionally substituted bicyclo[1.1.1]pentane, optionally substituted phenyl, or optionally substituted piperidine.

4. The compound of claim 1, or a pharmaceutically acceptable salt, solvate, hydrate, tautomer, or stereoisomer thereof, wherein R$^1$ is an optionally substituted 5-membered heteroaryl ring.

5. The compound of claim 4, or a pharmaceutically acceptable salt, solvate, hydrate, tautomer, or stereoisomer thereof, wherein R$^1$ is optionally substituted thiazole, oxazole, imidazole, or pyrazole.

6. The compound of claim 1, or a pharmaceutically acceptable salt, solvate, hydrate, tautomer, or stereoisomer thereof, wherein R$^1$ is of formula:

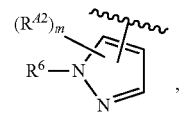

wherein:

each instance of R$^{A2a}$ is independently hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A2a}$, —N(R$^{A2b}$)$_2$, or —SR$^{A2a}$;

each occurrence of R$^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

each occurrence of R$^{A2b}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of R$^{A2b}$ are taken together with their intervening atoms to form a substituted or unsubstituted heterocyclic or substituted or unsubstituted heteroaryl ring;

R$^6$ is hydrogen, optionally substituted acyl, optionally substituted alkyl, or a nitrogen protecting group; and m is 0, 1, 2, or 3.

7. The compound of claim 1, or a pharmaceutically acceptable salt, solvate, hydrate, tautomer, or stereoisomer thereof, wherein R$^1$ is of formula:

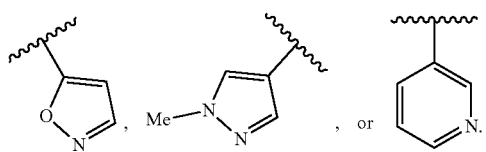
8. The compound of claim 6, or a pharmaceutically acceptable salt, solvate, hydrate, tautomer, or stereoisomer thereof, wherein $R^1$ is of formula:
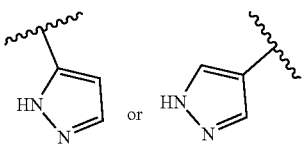
9. The compound of claim 1, wherein the compound is of formula:
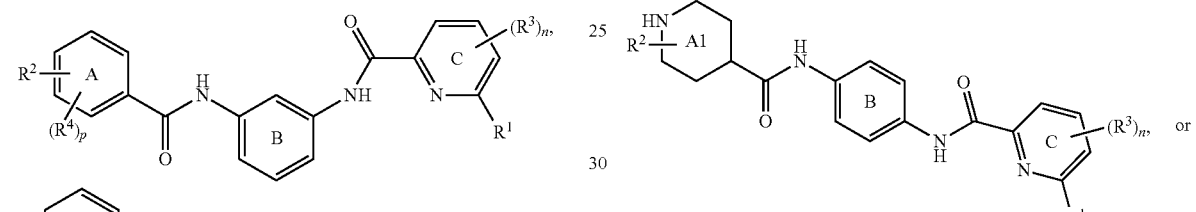
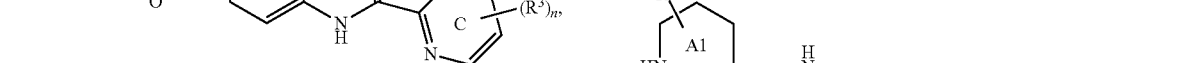
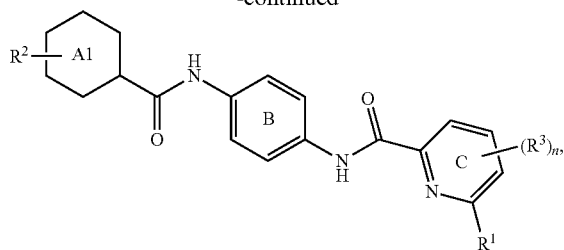
or a pharmaceutically acceptable salt, solvate, hydrate, tautomer, or stereoisomer thereof.
10. The compound of claim 1, wherein the compound is of formula:
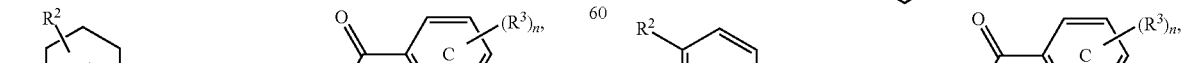

175
-continued

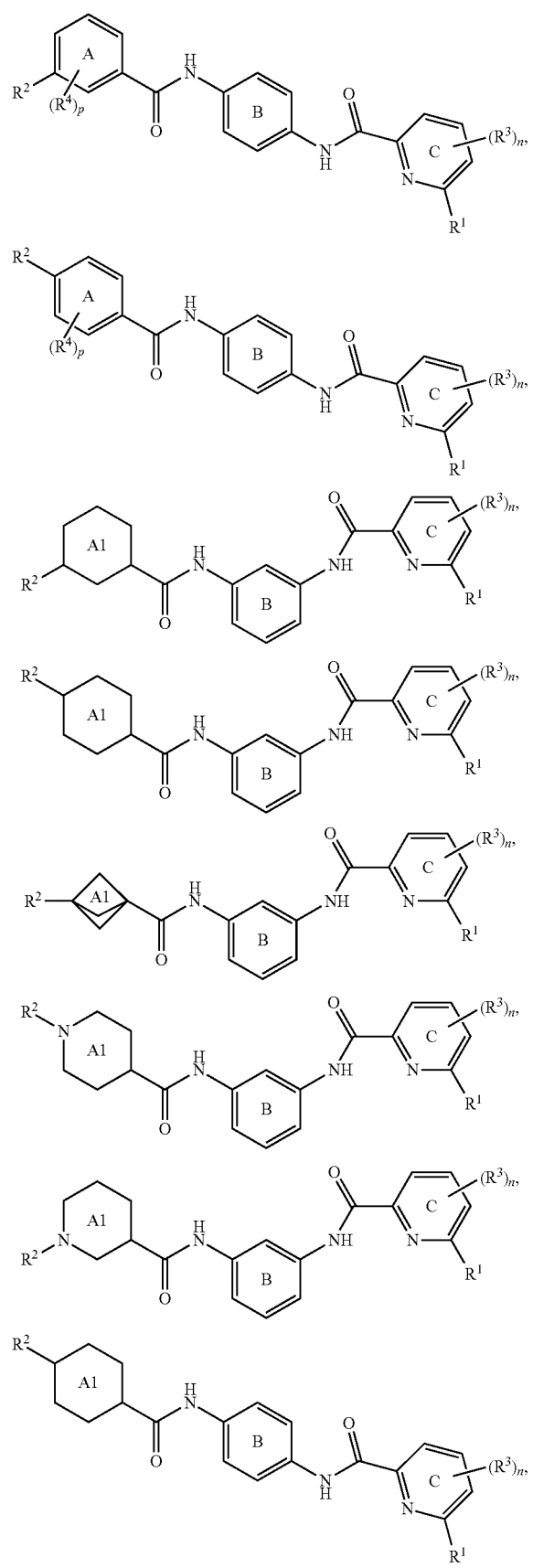

176
-continued

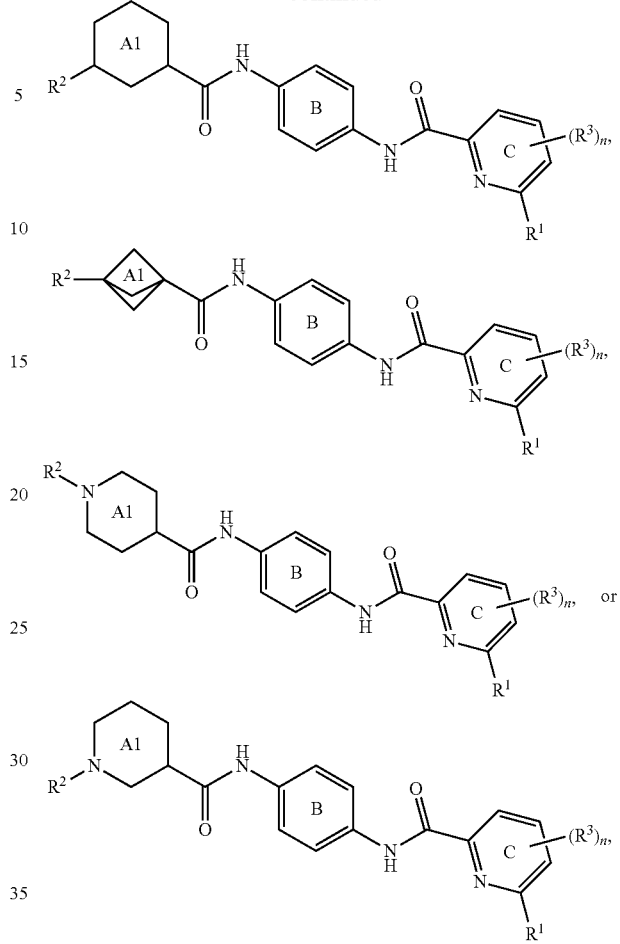

or a pharmaceutically acceptable salt, solvate, hydrate, tautomer, or stereoisomer thereof.

11. The compound of claim 1, or a pharmaceutically acceptable salt, solvate, hydrate, tautomer, or stereoisomer thereof, wherein $R^2$ is of formula:

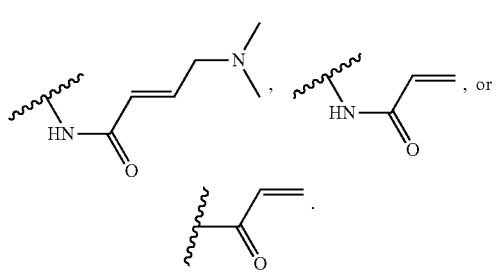

12. The compound of claim 1, or a pharmaceutically acceptable salt, solvate, hydrate, tautomer, or stereoisomer thereof, wherein n is 0.

13. The compound of claim 1, or a pharmaceutically acceptable salt, solvate, hydrate, tautomer, or stereoisomer thereof, wherein p is 0.

14. The compound of claim 2, or a pharmaceutically acceptable salt, solvate, hydrate, tautomer, or stereoisomer thereof, wherein $L^1$ is of formula

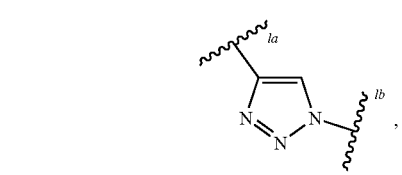 [SMILES: *c1cn(*)nn1]
or <sup>1a</sup>—NHC(=O)—<sup>1b</sup>.
15. The compound of claim 1, or a pharmaceutically acceptable salt, solvate, hydrate, tautomer, or stereoisomer thereof, wherein $L^{1A}$ is <sup>1a</sup>—NHC(=O)—<sup>1b</sup>.
16. The compound of claim 1, wherein the compound is of formula:
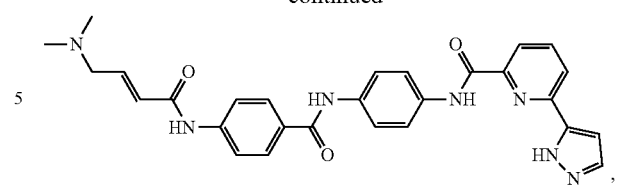
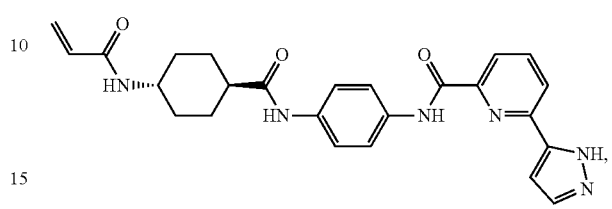
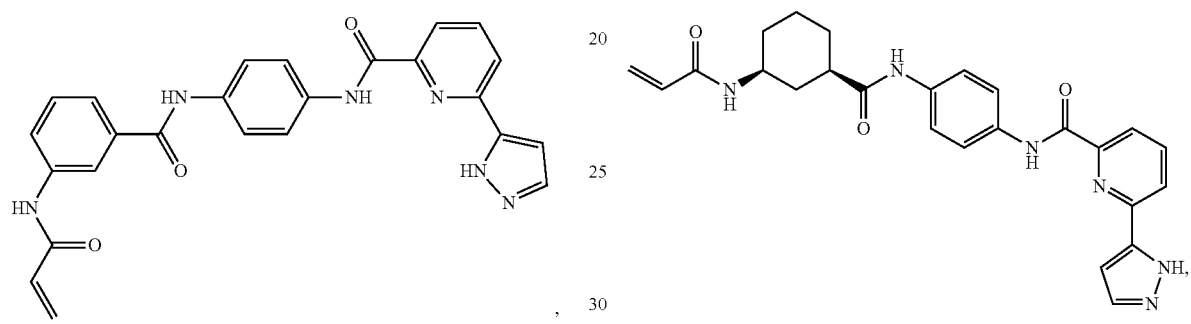
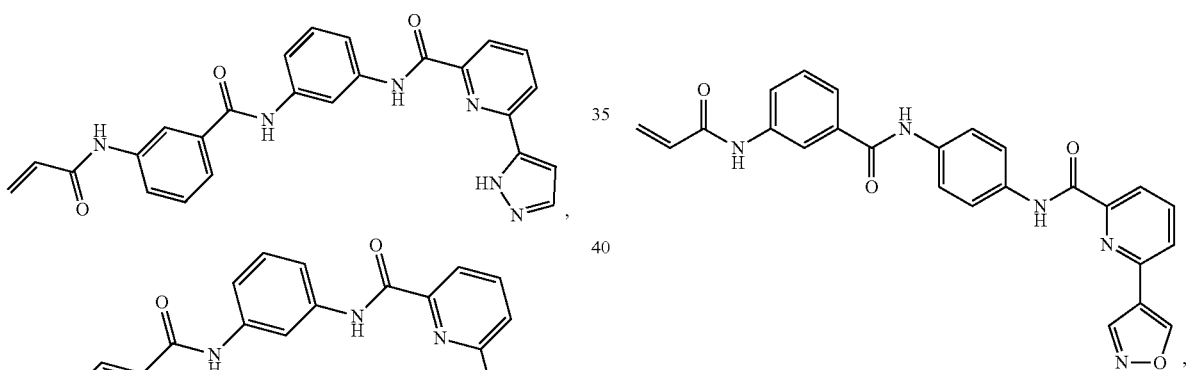
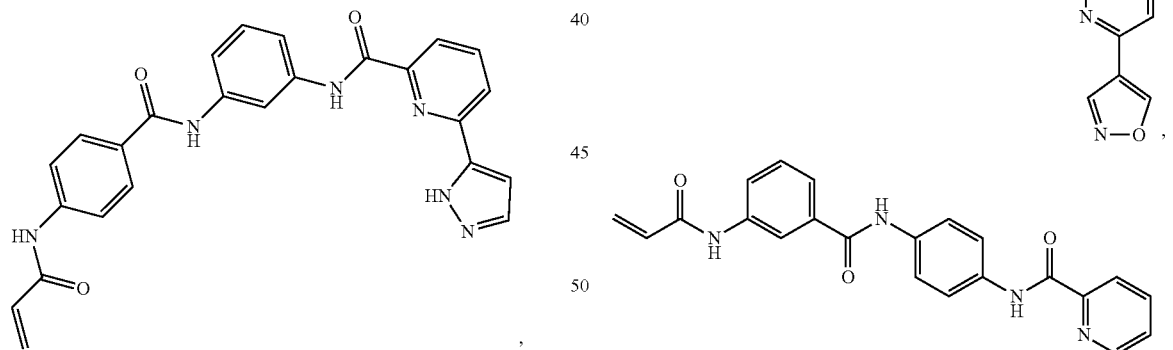
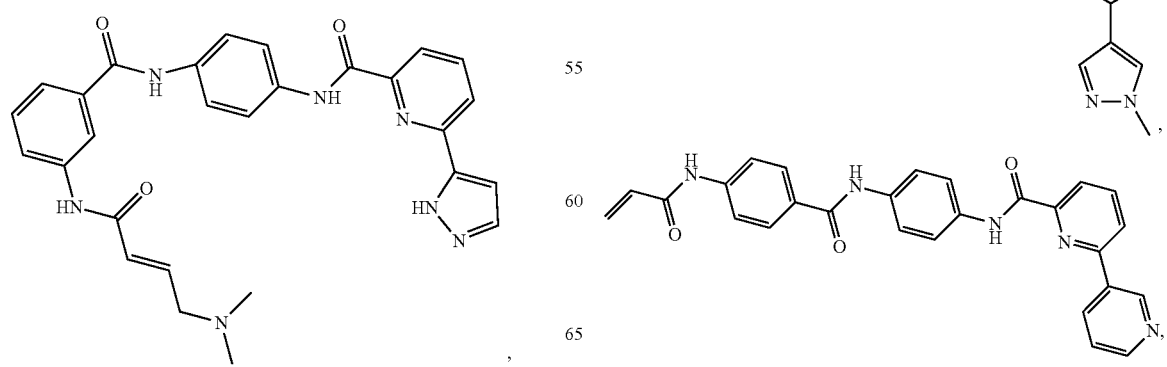

179
-continued
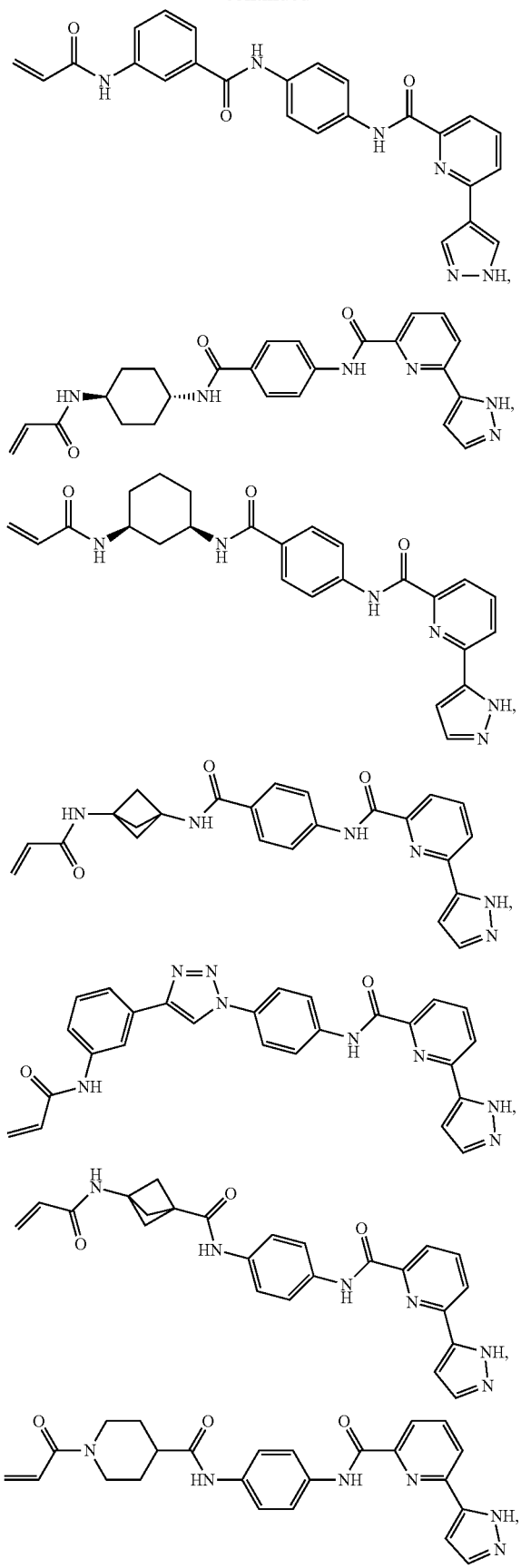
180
-continued
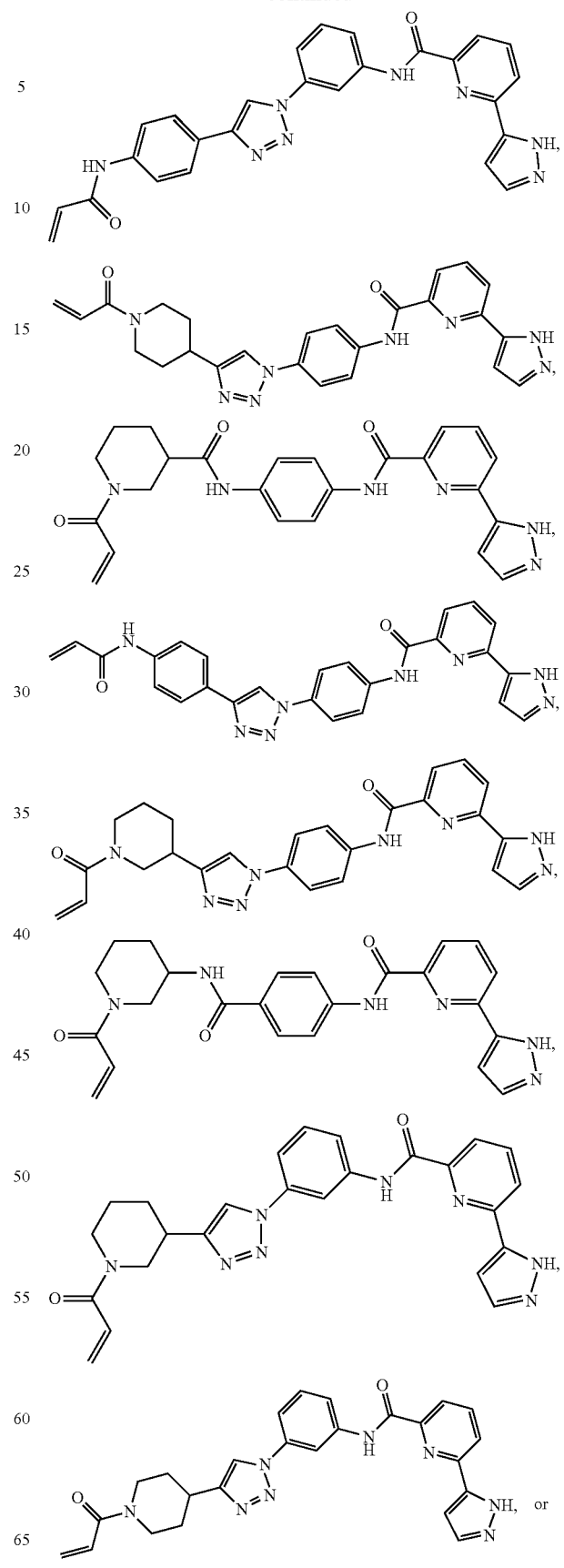

-continued

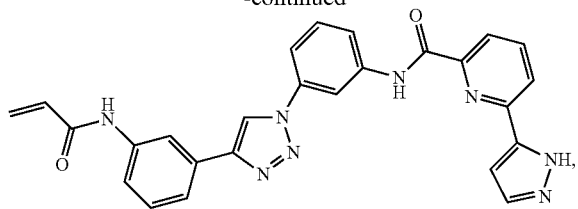

or a pharmaceutically acceptable salt, solvate, hydrate, tautomer, or stereoisomer thereof.

17. A pharmaceutical composition comprising a compound of claim 1, or a pharmaceutically acceptable salt, solvate, hydrate, tautomer, or stereoisomer thereof, and a pharmaceutically acceptable excipient.

18. A method of treating a proliferative disease in a subject in need thereof, the method comprising administering to the subject a therapeutically effective amount of a compound of claim 1, or a pharmaceutically acceptable salt, solvate, hydrate, tautomer, or stereoisomer thereof, or a pharmaceutical composition thereof, wherein the proliferative disease comprises pancreatic cancer, lung cancer, prostate cancer, breast cancer, ovarian cancer, kidney cancer, liver cancer, Ewing's sarcoma, myeloma, Waldenstrom's macroglobulinemia, myelodysplastic syndrome (MDS), osteosarcoma, brain cancer, neuroblastoma, colorectal cancer, acute myeloid leukemia (AML), diffuse large B-cell lymphoma (DLBCL), primary CNS lymphoma, marginal zone lymphoma, chronic lymphocytic leukemia, or Burkitt lymphoma.

19. A method of inhibiting the activity of an interleukin-1 receptor-associated kinase (IRAK) in a biological sample or subject, the method comprising administering to the subject or contacting the biological sample with a therapeutically effective amount of a compound of claim 1, or a pharmaceutically acceptable salt, solvate, hydrate, tautomer, or stereoisomer thereof, or a pharmaceutical composition thereof.

20. A method of inhibiting cell growth in a biological sample or subject, the method comprising:
administering to the subject or contacting the biological sample with a therapeutically effective amount of a compound of claim 1, or a pharmaceutically acceptable salt, solvate, hydrate, tautomer, or stereoisomer thereof, or a pharmaceutical composition thereof.

* * * * *